(12) United States Patent
Shishido et al.

(10) Patent No.: US 11,040,048 B2
(45) Date of Patent: Jun. 22, 2021

(54) MEDICAMENT FOR TREATING INFLUENZA CHARACTERIZED BY COMBINING A CAP-DEPENDENT ENDONUCLEASE INHIBITOR AND AN ANTI-INFLUENZA DRUG

(71) Applicant: Shionogi & Co., Ltd., Osaka (JP)

(72) Inventors: Takao Shishido, Osaka (JP); Takeshi Noshi, Osaka (JP); Atsuko Yamamoto, Osaka (JP); Mitsutaka Kitano, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 305 days.

(21) Appl. No.: 16/061,495

(22) PCT Filed: Dec. 14, 2016

(86) PCT No.: PCT/JP2016/087170
§ 371 (c)(1),
(2) Date: Jun. 12, 2018

(87) PCT Pub. No.: WO2017/104691
PCT Pub. Date: Jun. 22, 2017

(65) Prior Publication Data
US 2020/0261481 A1    Aug. 20, 2020

(30) Foreign Application Priority Data
Dec. 15, 2015   (JP) .............................. JP2015-244492

(51) Int. Cl.
A61K 31/685   (2006.01)
A61P 31/16    (2006.01)
(Continued)

(52) U.S. Cl.
CPC .......... *A61K 31/685* (2013.01); *A61K 31/196* (2013.01); *A61K 31/351* (2013.01);
(Continued)

(58) Field of Classification Search
CPC ...... A61K 31/53; A61K 31/5383; A61P 31/16
See application file for complete search history.

(56) References Cited

U.S. PATENT DOCUMENTS 5,475,109 A     12/1995  Selnick et al.
10,392,406 B2 *  8/2019  Kawai .................. A61K 31/542
(Continued)

FOREIGN PATENT DOCUMENTS

CN      108440564       8/2018
CN      108727369      11/2018
(Continued)

OTHER PUBLICATIONS

Bundgaard (ed.) Design of Prodrugs, Elsevier Science Publishers B.V., The Netherlands, 1985, Hans Bundgaard, ed., 1 page (Year: 1985).*

(Continued)

*Primary Examiner* — James D. Anderson
(74) *Attorney, Agent, or Firm* — Wenderoth, Lind & Ponack, L.L.P.

(57) ABSTRACT

A medicament characterized in that (A) a compound represented by the formula (I):

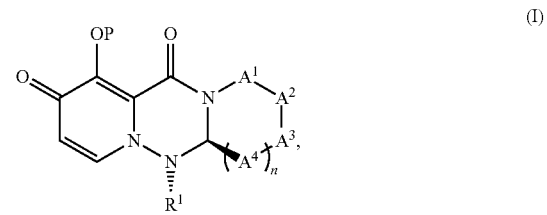

its pharmaceutically acceptable salt, or a solvate thereof, wherein
P is hydrogen or a group to form a prodrug;
$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is each independently $CR^{4A}R^{4B}$, S or O;
the number of hetero atoms among atoms constituting the ring which consists of $A^1$, $A^2$, $A^3$, $A^4$, nitrogen atom adjacent to $A^1$ and carbon atom adjacent to $A^4$ is 1 or 2;
$R^{1A}$ and $R^{1B}$ are each independently hydrogen, halogen, alkyl or the like;
$R^{2A}$ and $R^{2B}$ are each independently hydrogen, halogen, alkyl, or the like;
$R^{3A}$ and $R^{3B}$ are each independently hydrogen, halogen, alkyl, or the like;
$R^{4A}$ are each independently hydrogen, halogen, alkyl, or the like;
$R^{4B}$ are each independently hydrogen, halogen, alkyl, or the like;
$R^{3A}$ and $R^{3B}$ may be taken together with an adjacent carbon atom to form non-aromatic carbocycle or non-aromatic heterocycle;
n is any integer of 1 to 2; and
$R^1$ is

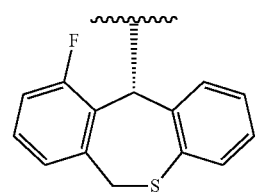

or the like, (Continued)

is combined with (B) compound(s) having an anti-influenza activity, its pharmaceutically acceptable salt or a solvate thereof and/or an antibody having anti-influenza activity, is useful for treating or preventing influenza.

15 Claims, 1 Drawing Sheet

(51) Int. Cl.
    *A61K 31/196*     (2006.01)
    *A61K 31/351*     (2006.01)
    *A61K 31/426*     (2006.01)
    *A61K 31/506*     (2006.01)
    *A61K 31/53*     (2006.01)
    *A61K 31/5383*     (2006.01)
    *A61K 31/664*     (2006.01)
    *A61K 39/395*     (2006.01)
    *A61K 45/06*     (2006.01)

(52) U.S. Cl.
    CPC .......... *A61K 31/426* (2013.01); *A61K 31/506* (2013.01); *A61K 31/53* (2013.01); *A61K 31/5383* (2013.01); *A61K 31/664* (2013.01); *A61K 39/3955* (2013.01); *A61K 45/06* (2013.01); *A61P 31/16* (2018.01)

(56) References Cited

U.S. PATENT DOCUMENTS

| | | | |
|---|---|---|---|
| 10,633,397 B2* | 4/2020 | Kawai | A61K 31/542 |
| 10,759,814 B2* | 9/2020 | Kawai | A61P 31/16 |
| 2013/0090300 A1 | 4/2013 | Bauman et al. | |
| 2013/0096109 A1 | 4/2013 | Hattori et al. | |
| 2013/0197219 A1* | 8/2013 | Takahashi | A61K 31/4738 544/112 |

FOREIGN PATENT DOCUMENTS

| | | |
|---|---|---|
| EP | 1 544 199 | 6/2005 |
| EP | 1 950 212 | 7/2008 |
| EP | 2 042 502 | 4/2009 |
| EP | 2 444 400 | 4/2012 |
| EP | 2 620 436 | 7/2013 |
| EP | 3 290 424 | 3/2018 |
| EP | 3 473 629 | 4/2019 |
| GB | 2 280 435 | 2/1995 |
| JP | 2017-137291 | 8/2017 |
| WO | 2006/066414 | 6/2006 |
| WO | 2013/057251 | 4/2013 |
| WO | 2013/057253 | 4/2013 |
| WO | 2013/174930 | 11/2013 |
| WO | 2013/174931 | 11/2013 |
| WO | 2014/023691 | 2/2014 |
| WO | 2014/043252 | 3/2014 |
| WO | 2014/074926 | 5/2014 |
| WO | 2014/108406 | 7/2014 |
| WO | 2014/108407 | 7/2014 |
| WO | 2014/108408 | 7/2014 |
| WO | 2015/038655 | 3/2015 |
| WO | 2015/038660 | 3/2015 |
| WO | 2016/005330 | 1/2016 |
| WO | 2016/005331 | 1/2016 |
| WO | 2017/046362 | 3/2017 |
| WO | 2017/072341 | 5/2017 |
| WO | 2017/109088 | 6/2017 |
| WO | 2017/153919 | 9/2017 |
| WO | 2017/158147 | 9/2017 |
| WO | 2017/158151 | 9/2017 |
| WO | 2017/223231 | 12/2017 |
| WO | 2018/030463 | 2/2018 |
| WO | 2018/042303 | 3/2018 |
| WO | 2018/108125 | 6/2018 |

OTHER PUBLICATIONS

Silverman (ed.) The Organic Chemistry of Drug Design and Drug Action, Academic Press, Inc., San Diego, CA., 1992, Richard B. Silverman, ed., Chapter 8, "Prodrugs and Drug Delivery Systems", pp. 352-400 (Year: 1992).*
Wolff (ed.) Burger's Medicinal Chemistry and Drug Discovery, John Wiley & Sons, Inc., New York, 1995, 5th Ed., vol. 1: Principles and Practice, pp. 975-977 (Year: 1995).*
Singh, S. B., "Total Synthesis of Flutimide, a Novel Endonuclease Inhibitor of Influenza Virus", Tetrahedron Letters, 1995, vol. 36, No. 12, pp. 2009-2012.
Hensens, O.D. et al., "Isolation and Structure of Flutimide, a Novel Endonuclease Inhibitor of Influenza Virus", Tetrahedron Letters, 1995, vol. 36, No. 12, pp. 2005-2008.
Muthuri, S. G. et al.,"Effectiveness of neuraminidase inhibitors in reducing mortality in patients admitted to hospital with influenza a H1N1pdm09 virus infection: a meta-analysis of individual participant data", Lancet Respir Med., May 2014, vol. 2(5), pp. 395-404.
Ju, H. et al., "Inhibitors of Influenza Virus Polymerase Acidic (PA) Endonuclease: Contemporary Developments and Perspectives", J. Med. Chem., 2017, vol. 60 (9), pp. 3533-3551.
Singh and Tomassini, "Synthesis of Natural Flutimide and Analogous Fully Substituted Pyrazine-2,6-diones, Endonuclease Inhibitors of Influenza Virus", J. Org. Chem., 2001, vol. 66, pp. 5504-5516.
Shoji, M. et al., "Anti-Influenza Activity of $C_{60}$ Fullerene Derivatives", PLoS One, Jun. 2013, vol. 8, No. 6, e66337.
Iwai, Y. et al., "Anti-Influenza Activity of Marchantins, Macrocyclic Bisbibenzyls Contained in Liverworts", PLoS One, May 2011, vol. 6, No. 5, e19825.
Iwai, Y. et al., "Green tea catechins inhibit the endonuclease activity of influenza A virus RNA polymerase", PLoS Curr. 2009, RRN1052.
Xie, Y. et al., "Caffeic acid derivatives: A new type of influenza neuraminidase inhibitors", Bioorganic & Medicinal Chemistry Letters, 2013, vol. 23, pp. 3556-3560.
Pala, N. et al., "Virtual Screening and Biological Validation of Novel Influenza Virus PA Endonuclease Inhibitors", ACS Med. Chem. Lett., 2015, vol. 6, pp. 866-871.
Sagong, H. Y. et al., "Phenyl Substituted 4-Hydroxypyridazin-3(2H)-ones and 5-Hydroxypyrimidin-4(3H)-ones: Inhibitors of Influenza A Endonuclease", J. Med. Chem., 2014, vol. 57, pp. 8086-8098.
Bauman J. D. et al., "Crystallographic Fragment Screening and Structure-Based Optimization Yields a New Class of Influenza Endonuclease Inhibitors", ACS Chem. Biol., 2013, vol. 8, pp. 2501-2508.
Iwai, Y. et al., "Anti-influenza activity of phenethylphenylphthalimide analogs derived from thalidomide", Bioorganic & Medicinal Chemistry, vol. 18, 2010, pp. 5379-5390.
Sagong H. Y. et al., "3-Hydroxyquinolin-2(1H)-ones as Inhibitors of Influenza a Endonuclease", ACS Med. Chem. Lett., 2013, vol. 4, pp. 547-550.
Yan, Z. et al., "Design of the influenza virus inhibitors targeting the PA endonuclease using 3D-QSAR modeling, side-chain hopping, and docking", Bioorganic & Medicinal Chemistry Letters, 2014, vol. 24, pp. 539-547.
Chen, E. et al., "Computation-Guided Discovery of Influenza Endonuclease Inhibitors", ACS Med. Chem. Lett., vol. 5, 2014, pp. 61-64.
Baughman, B. M. et al., "Identification of Influenza Endonuclease Inhibitors Using a Novel Fluorescence Polarization Assay", ACS Chem. Biol., vol. 7, 2012, pp. 526-534.
Parhi, a. K. et al., "Phenyl substituted 3-hydroxypyridin-2(1H)-ones: Inhibitors of influenza A endonuclease", Bioorganic & Medicinal Chemistry, 2013, vol. 21, pp. 6435-6446.
Parkes K. E. et al., "Use of a Pharmacophore Model to Discover a New Class of Influenza Endonuclease Inhibitors", J. Med. Chem., 2003, vol. 46, pp. 1153-1164.
Kojima, T., "Pursuing efficiency of crystal selection in drug development",Yakuzaigaku (Pharmaceutics), 2008, vol. 68, No. 5, pp. 344-349, with English machine translation.

(56) References Cited

OTHER PUBLICATIONS

Hastings J. C., et al., "Anti-Influenza Virus Activities of 4-Substituted 2,4-Dioxobutanoic Acid Inhibitors", Antimicrobial Agents and Chemotherapy, May 1996, vol. 40, No. 5, pp. 1304-1307.
Tomassini, J. et al., "Inhibition of Cap ($m^7$GpppXm)-Dependent Endonuclease of Influenza Virus by 4-Substituted 2,4-Dioxobutanoic Acid Compounds", Antimicrobial Agents and Chemotherapy, Dec. 1994, vol. 38, No. 12, pp. 2827-2837.
International Preliminary Report on Patentability dated Jun. 19, 2018 in International (PCT) Application No. PCT/JP2016/087170.
International Search Report dated Feb. 14, 2017 in International Application No. PCT/JP2016/087170.
Jake Dunning et al., "Antiviral combinations for severe influenza", The Lancer Infectious Diseases, 2014, vol. 14, p. 1259-1270.
Torsten Steinmetzer et al., "Strategies for the Development of Influenza Drugs: Basis for New Efficient Combination Therapies", Topics in Medicinal Chemistry, 2015.02, vol. 15, p. 143-182.
Michael P. Clark, et al., "Discovery of a Novel, First-in-Class, Orally Bioavailable Azaindole Inhibitor (VX-787) of Influenza PB2", Journal of Medicinal Chemistry, 2014, vol. 57, p. 6668-6678.
Giuseppe Belardo et al., "Synergistic Effect of Nitazoxanide with Neuraminidase Inhibitors against Influenza A Viruses In Vitro", Antimicrobial Agents and Chemotherapy, Feb. 2015 vol. 59 No. 2, p. 1061-1069.
Sehee Park et al., "Combination Effects of Peramivir and Favipiravir against Oseltamivir-Resistant 2009 Pandemic Influenza A(H1N1) Infection in Mice", PLOS ONE, 2014, vol. 9, Issue 7, p. 101325.
Shanta Banita et al., "Combination of peramivir rimantadine demonstrate synergistic antiviral effects in sub-lethal influenza A (H3N2) virus mouse model", Antiviral Research 2010, vol. 88 p. 276-280.
Randal A. Byrn et al., "Preclinical Activity of VX-787, a First-in-Class, Orally Bioavailable Inhibitor of the Influenza Virus Polymerase PB2 Subunit", Antimicrobial Agents and Chemotherapy, Mar. 2015 vol. 59 No. 3, p. 1569-1582.
E. Bart Tarbet et al., "In vitro activity of favipiravir and neuraminidase inhibitor combinations against oseltamivir-sensitive and oseltamivir-resistant pandemic influenza A (H1N1) virus", Arch Virol (2014) 159:1279-1291, DOI 10.1007/s00705-013-1922-1.

\* cited by examiner

[Figure 1]
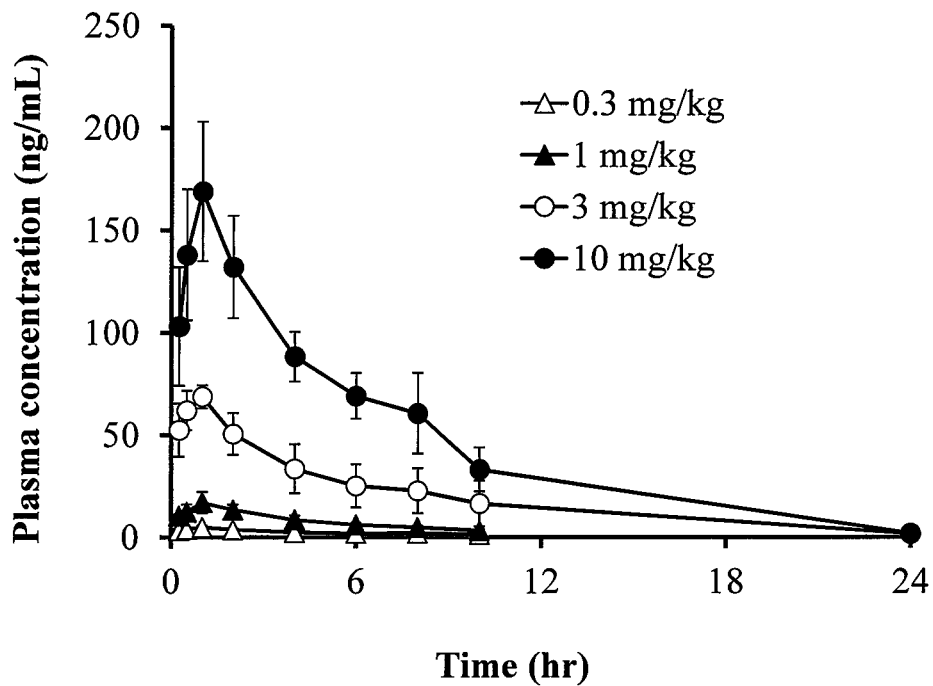
[Figure 2]
| Time | Plasma concentration (ng/mL) | | | |
|---|---|---|---|---|
| (hr) | 0.3 mg/kg | 1 mg/kg | 3 mg/kg | 10 mg/kg |
| 0.25 | BLQ | BLQ | BLQ | BLQ |
| 0.5 | BLQ | BLQ | BLQ | BLQ |
| 1 | BLQ | BLQ | BLQ | BLQ |
| 2 | BLQ | BLQ | BLQ | BLQ |
| 4 | BLQ | BLQ | BLQ | BLQ |
| 6 | BLQ | BLQ | BLQ | BLQ |
| 8 | BLQ | BLQ | BLQ | BLQ |
| 10 | BLQ | BLQ | BLQ | BLQ |
| 24 | BLQ | BLQ | BLQ | BLQ |
BLQ : below the lower limit of quantification (< 0.500 ng/mL)

MEDICAMENT FOR TREATING INFLUENZA CHARACTERIZED BY COMBINING A CAP-DEPENDENT ENDONUCLEASE INHIBITOR AND AN ANTI-INFLUENZA DRUG

TECHNICAL FIELD

The present invention relates to a medicament for treating influenza, characterized in that a compound having a cap-dependent endonuclease inhibitory activity, its pharmaceutically acceptable salt or a solvate thereof, is combined with at least one compound having an anti-influenza activity, its pharmaceutically acceptable salt and/or an antibody having an anti-influenza activity.

BACKGROUND ART

Influenza is an acute respiratory infectious disease caused by infection with an influenza virus. In Japan, millions of influenza-like patients are reported every winter, and influenza is accompanied with high morbidity and mortality. Influenza is a particularly important disease in a high risk population such as baby and elderly, a complication rate with pneumonia is high in elderly, and death with influenza is occupied with elderly in many cases.

However, Amantadine, Oseltamivir and the like which currently used have problems of emergence of resistant strains and side effects.

Currently, a method of using anti-influenza agents in combination has been studied for the purpose of reducing the tolerance of influenza virus, enhancing the therapeutic effect and/or reducing side effects, etc. However, satisfactory effects are not necessarily obtained because the number of drugs used for combination is limited.

As anti-influenza drugs, Amantadine (trade name: Symmetrel) and Rimantadine (trade name: Flumadine) which inhibit the denucleation process of a virus, Oseltamivir (trade name: Tamiflu), Zanamivir (trade name: Relenza), Peramivir (trade name: Rapiacta) and Laninamivir (trade name: Inavir) which are neuraminidase inhibitors suppressing virus budding and release from a cell, and Favipiravir (trade name: Avigan) which inhibits RNA polymerase are known.

In addition, research on compounds and antibodies acting on various mechanisms that have an effect on influenza virus as a candidate for anti-influenza drugs have also been made. Examples includes compounds having a neuraminidase inhibitory activity, compounds having a RNA-dependent RNA polymerase inhibitory activity, compounds having a M2 protein inhibitory activity, compounds having a PB2 Cap binding inhibitory activity, compounds having a HA maturation inhibitory activity, recombinant sialidases, compounds having a re-assemble inhibitory activity, compounds having a RNA interference activity, compounds having a receptor of hemagglutinin binding inhibitory activity, compounds having a membrane of HA fusion inhibitory activity, compounds having a NP nuclear translocation inhibitory activity, compounds having a cap-dependent endonuclease (CEN) inhibitory activity, compounds having a CXCR inhibitory activity, compounds having a CRM 1 inhibitory activity and an anti-HA antibody.

Patent Document 1 and 2 describe compounds represented by formula:

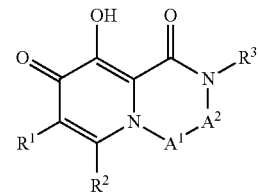

which have CEN inhibitory activity, and prodrugs thereof. But they neither disclose nor suggest any combination with other drugs.

PRIOR ART DOCUMENTS

Patent Documents

Patent Document 1: WO2010/147068
Patent Document 2: WO2012/039414

SUMMARY OF THE INVENTION

Problems to be Solved by the Invention

An object of the present invention is to provide a medicament useful for treating or preventing influenza which has strong anti-influenza virus activity and few side effects.

Means for Solving the Problems

Japanese Patent Application No. 2015-090909, which was issued as Japanese Patent No. 5971830, on Aug. 17, 2016) describes compounds represented by formula:

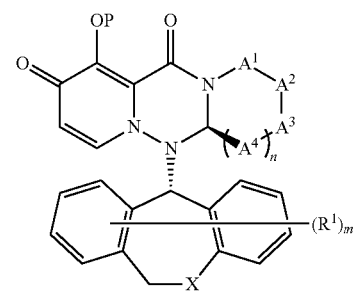

which have CEN inhibitory activity. Anti-influenza agents of six mechanisms are enumerated as drugs that can be used together with the above compounds. But no specific combinations are described, and it neither discloses nor suggests any combination effects.

The present invention provides inventions shown below.
(1) A medicament characterized in that (A) a compound represented by the formula (I):

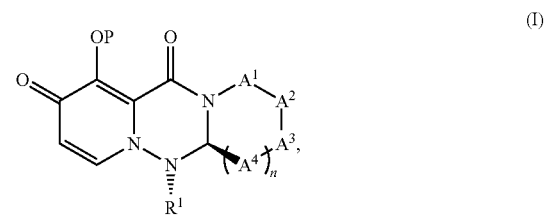

(I)

its pharmaceutically acceptable salt, or a solvate thereof, wherein
P is hydrogen or a group to form a prodrug;
$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is each independently $CR^{4A}R^{4B}$, S or O;
the number of hetero atoms among atoms constituting the ring which consists of $A^1, A^2, A^3, A^4$, nitrogen atom adjacent to $A^1$ and carbon atom adjacent to $A^4$ is 1 or 2;
$R^{1A}$ and $R^{1B}$ are each independently hydrogen, halogen, alkyl, haloalkyl, alkyloxy or phenyl;
$R^{2A}$ and $R^{2B}$ are each independently hydrogen, halogen, alkyl, haloalkyl, alkyloxy or phenyl;
$R^{3A}$ and $R^{3B}$ are each independently hydrogen, halogen, alkyl, haloalkyl, alkyloxy or phenyl;
$R^{4A}$ are each independently hydrogen, halogen, alkyl, haloalkyl, alkyloxy or phenyl;
$R^{4B}$ are each independently hydrogen, halogen, alkyl, haloalkyl, alkyloxy or phenyl;
$R^{3A}$ and $R^{3B}$ may be taken together with an adjacent carbon atom to form non-aromatic carbocycle or non-aromatic heterocycle;
n is any integer of 1 to 2; and
$R^1$ is

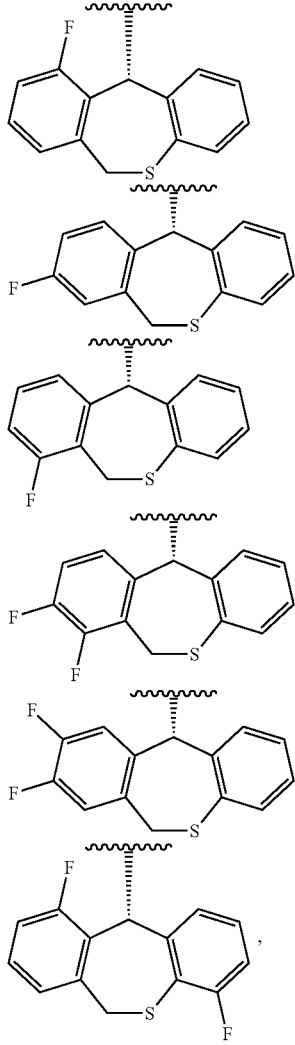

or is combined with (B) compound(s) having an anti-influenza activity, its pharmaceutically acceptable salt or a solvate thereof and/or an antibody having anti-influenza activity.

(2) The medicament according to (1), wherein the group represented by the formula:

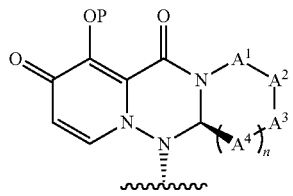

is the group represented by the formula:

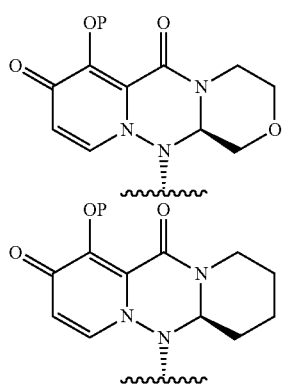

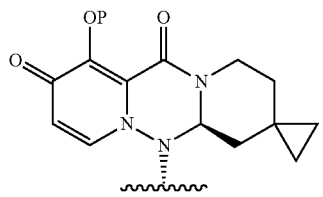

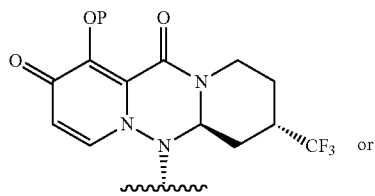 or

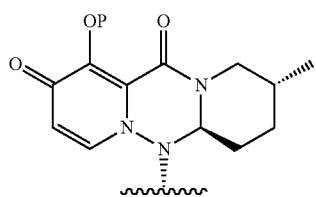

wherein each definition has the same meaning as described (1).

(3) The medicament according to (1) or (2), wherein (A) is the compound represented by the formula:

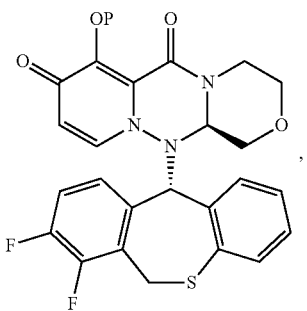

its pharmaceutically acceptable salt, or a solvate thereof.
(4) The medicament according to any one of (1) to (3), wherein P is hydrogen or a group selected from the following formula:
a) —C(=O)—P$^{R0}$,
b) —C(=O)—P$^{R1}$,
c) —C(=O)-L-P$^{R1}$,
d) —C(=O)-L-O—P$^{R1}$,
e) —C(=O)-L-O-L-O—P$^{R1}$,
f) —C(=O)-L-O—C(=O)—P$^{R1}$,
g) —C(=O)—O—P$^{R2}$,
h) —C(=O)—N(—K)(P$^{R2}$),
i) —C(=O)—O-L-O—P$^{R2}$,
i') —C(=O)—O-L-N(—K)(P$^{R2}$),
j) —C(P$^{R3}$)$_2$—O—P$^{R4}$,
k) —C(P$^{R3}$)$_2$—O-L-O—P$^{R4}$,
l) —C(P$^{R3}$)$_2$—O—C(=O)—P$^{R4}$,
m) —C(P$^{R3}$)$_2$—O—C(=O)—O—P$^{R4}$,
n) —C(P$^{R3}$)$_2$—O—C(=O)—N(—K)—P$^{R4}$,
o) —C(P$^{R3}$)$_2$—O—C(=O)—O-L-O—P$^{R4}$,
p) —C(P$^{R3}$)$_2$—O—C(=O)—O-L-N(P$^{R4}$)$_2$,
q) —C(P$^{R3}$)$_2$—O—C(=O)—N(—K)-L-O—P$^{R4}$,
r) —C(P$^{R3}$)$_2$—O—C(=O)—N(—K)-L-N(P$^{R4}$)$_2$,
s) —C(P$^{R3}$)$_2$—O—C(=O)—O-L-O-L-O—P$^{R4}$,
t) —C(P$^{R3}$)$_2$—O—C(=O)—O-L-N(—K)—C(=O)—P$^{R4}$,
u) —C(P$^{R3}$)$_2$—O—P(=O)(—P$^{R5}$)$_2$,
v) —(C(P$^{R3}$)$_2$)$_p$—P$^{R6}$,
w) —C(=N$^+$(P$^{R7}$)$_2$)(—N(P$^{R7}$)$_2$),
x) —(C(P$^{R3}$)$_2$)$_q$—C(=O)—O—P$^{R2}$,
x') —(C(P$^{R3}$)$_2$)$_q$—C(=O)—N(—K)—P$^{R4}$,
x") —(C(P$^{R3}$)$_2$)$_q$—C(=O)—P$^{R1}$,
y) —C(P$^{R3}$)$_2$—N(—K)—C(=O)—O—P$^{R2}$,
z) —P(=O)(—P$^{R8}$)(—P$^{R9}$),
aa) —S(=O)$_2$P$^{R10}$,
ab) —P$^{R11}$,
ac) —(C(P$^{R3}$)$_2$)$_r$—O—P$^{R12}$, and
ad) —(C(P$^{R3}$)$_2$)$_t$—N(—K)—P$^{R13}$,
wherein L is straight or branched alkylene optionally substituted by substituent group B, or straight or branched alkenylene optionally substituted by substituent group B;
K is hydrogen, or alkyl optionally substituted by substituent group A;
P$^{R0}$ is alkyl optionally substituted by substituent group A, or alkenyl optionally substituted by substituent group A;
P$^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
P$^{R3}$ is each independently hydrogen, alkyl or hydroxy;
two P$^{R3}$ on adjacent carbon atom may be taken together to form alkenylene or alkylene;
P$^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;
P$^{R5}$ is each independently hydroxy or OBn;
P$^{R6}$ is carbocyclyl group optionally substituted by substituent group A, or heterocyclyl group optionally substituted by substituent group A;
P$^{R7}$ is each independently alkyl optionally substituted by substituent group A;
P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or
P$^{R8}$ and P$^{R9}$ may be taken together with an adjacent phosphorus atom to form heterocycle optionally substituted by substituent group A;
P$^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;
P$^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A; P$^{R12}$ is each independently hydrogen or alkyl optionally substituted by substituent group A;
P$^{R13}$ is alkylsulfonyl optionally substituted by substituent group A;
p is any integer of 2 to 3;
q is any integer of 1 to 2;
r is any integer of 2 to 4; and
t is any integer of 2 to 4;
Substituent group A: oxo, alkyl, alkenyl, haloalkyl, hydroxyalkyl, amino, alkylamino, carbocyclyl group, heterocyclyl group, carbocyclylalkyl, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho;
Substituent group B: spiro ring and halogen.
(5) The medicament according to any one of (1) to (3), wherein P is hydrogen or a group selected from the following formula:
a) —C(=O)—P$^{R0}$,
b) —C(=O)—P$^{R1}$,
c) —C(=O)-L-P$^{R1}$,
d) —C(=O)-L-O—P$^{R1}$,
e) —C(=O)-L-O-L-O—P$^{R1}$, f) —C(=O)-L-O—C(=O)—P$^{R1}$,
g) —C(=O)—O—P$^{R2}$,
h) —C(=O)—N(—K)(P$^{R2}$),
i) —C(=O)—O-L-O—P$^{R2}$,
i') —C(=O)—O-L-N(—K)(P$^{R2}$),
j) —C(P$^{R3}$)$_2$—O—P$^{R4}$,
k) —C(P$^{R3}$)$_2$—O-L-O—P$^{R4}$,
l) —C(P$^{R3}$)$_2$—O—C(=O)—P$^{R4}$,
m) —C(P$^{R3}$)$_2$—O—C(=O)—O—P$^{R4}$,
n) —C(P$^{R3}$)$_2$—O—C(=O)—N(—K)—P$^{R4}$,
o) —C(P$^{R3}$)$_2$—O—C(=O)—O-L-O—P$^{R4}$,
p) —C(P$^{R3}$)$_2$—O—C(=O)—O-L-N(P$^{R4}$)$_2$,
q) —C(P$^{R3}$)$_2$—O—C(=O)—N(—K)-L-O—P$^{R4}$,
r) —C(P$^{R3}$)$_2$—O—C(=O)—N(—K)-L-N(P$^{R4}$)$_2$,
s) —C(P$^{R3}$)$_2$—O—C(=O)—O-L-O-L-O—P$^{R4}$,
t) —C(P$^{R3}$)$_2$—O—C(=O)—O-L-N(—K)—C(=O)—P$^{R4}$,
u) —C(P$^{R3}$)$_2$—O—P(=O)(—P$^{R5}$)$_2$,
v) —(C(P$^{R3}$)$_2$)$_p$—P$^{R6}$,
w) —C(=N$^+$(P$^{R7}$)$_2$)(—N(P$^{R7}$)$_2$),
x) —(C(P$^{R3}$)$_2$)$_q$—C(=O)—O—P$^{R2}$,
x') —(C(P$^{R3}$)$_2$)$_q$—C(=O)—N(—K)—P$^{R4}$,
x") —(C(P$^{R3}$)$_2$)$_q$—C(=O)—P$^{R1}$,
y) —C(P$^{R3}$)$_2$—N(—K)—C(=O)—O—P$^{R2}$,
z) —P(=O)(—P$^{R8}$)(—P$^{R9}$),
aa) —S(=O)$_2$P$^{R10}$,
ab) —P$^{R11}$,
ac) —(C(P$^{R3}$)$_2$)$_r$—O—P$^{R12}$, and
ad) —(C(P$^{R3}$)$_2$)$_t$—N(—K)—P$^{R13}$,
wherein L is straight or branched alkylene optionally substituted by substituent group B;
K is hydrogen, or alkyl optionally substituted by substituent group A;
P$^{R0}$ is alkyl optionally substituted by substituent group A;
P$^{R1}$ is carbocyclyl group optionally substituted by substituent group A or heterocyclyl group optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
P$^{R3}$ is each independently hydrogen, alkyl or hydroxy;
two P$^{R3}$ on adjacent carbon atom may be taken together to form alkenylene or alkylene;
P$^{R4}$ is alkyl optionally substituted by substituent group A, carbocyclyl group optionally substituted by substituent group A or heterocyclyl group optionally substituted by substituent group A;
P$^{R6}$ is carbocyclyl group optionally substituted by substituent group A or heterocyclyl group optionally substituted by substituent group A;
P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and
P$^{R8}$ and P$^{R9}$ may be taken together with an adjacent phosphorus atom to form heterocycle optionally substituted by substituent group A;

P$^{R10}$ is alkyl optionally substituted by substituent group A, carbocyclyl group optionally substituted by substituent group A or carbocyclylalkyl optionally substituted by substituent group A;
P$^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;
P$^{R12}$ is each independently hydrogen or alkyl optionally substituted by substituent group A;
P$^{R13}$ is alkylsulfonyl optionally substituted by substituent group A;
p is any integer of 2 to 3;
q is any integer of 1 to 2;
r is any integer of 2 to 4; and
t is any integer of 2 to 4;
Substituent group A: oxo, alkyl, alkenyl, haloalkyl, alkylamino, carbocyclyl group, heterocyclyl group, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkyl amino alkyl, alkyloxy, cyano, nitro, azido, alkylsulfonyl, trialkylsilyl and phospho;
Substituent group B: spiro ring.
(6) The medicament according to any one of (1) to (5), wherein (A) is the compound represented by the formula:

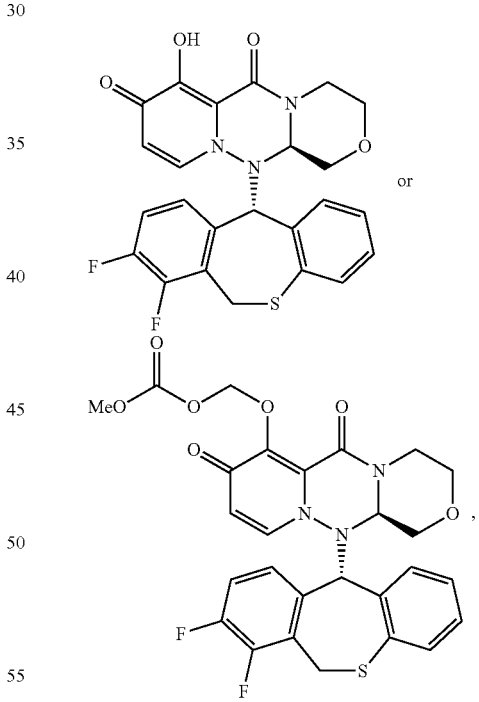

its pharmaceutically acceptable salt or a solvate thereof.
(7) The medicament according to any one of (1) to (6), wherein (B) is at least one compound selected from the group consisting of a compound having a neuraminidase inhibitory activity, a compound having a RNA-dependent RNA polymerase inhibitory activity, a compound having a M2 protein inhibitory activity, a compound having a PB2 Cap binding inhibitory activity, a compound having a HA maturation inhibitory activity, a recombinant sialidase, a compound having a re-assemble inhibitory activity, a compound having a RNA interference activity, a compound having a receptor of hemagglutinin binding inhibitory activity, a compound having a membrane of HA fusion inhibitory activity, a compound having a NP nuclear translocation inhibitory activity, a compound having a CXCR inhibitory activity and a compound having a CRM1 inhibitory activity, its pharmaceutically acceptable salt or a solvate thereof and/or an anti-HA antibody.

(8) The medicament according to (7), wherein (B) is at least one compound selected from the group consisting of Oseltamivir, Zanamivir, Peramivir, Laninamivir, Fabipiravir, Amantazine, Flumazine, VX-787, MHAA4549A, TCN-032, VIS-410, CR-8020, CR-6261, CT-P27 and MEDI-8852.

(9) The medicament according to any one of (1) to (8), wherein (A) and (B) are simultaneously or sequentially administered.

(10) The medicament according to any one of (1) to (8), wherein the medicament is combination drugs.

(11) The medicament according to any one of (1) to (10), wherein the medicament is used for the treatment or prevention of influenza.

(12) An enhancer of the anti-influenza activity of compound(s) having an anti-influenza activity, its pharmaceutically acceptable salt or a solvate thereof, and/or an antibody having an anti-influenza activity comprising a compound represented by the formula (I) in (1), its pharmaceutically acceptable salt or a solvate thereof.

(13) An enhancer of the anti-influenza activity of a compound represented by the formula (I) in (1), its pharmaceutically acceptable salt or a solvate thereof comprising a compound having an anti-influenza activity, its pharmaceutically acceptable salt or a solvate thereof, and/or an antibody having anti-influenza activity.

(14) The medicament for simultaneously or sequentially administering a compound having an anti-influenza activity, its pharmaceutically acceptable salt or a solvate thereof, and/or an antibody having an anti-influenza activity comprising a therapeutically effective amount of the compound represented by the formula (I) in (1), its pharmaceutically acceptable salt or a solvate thereof.

(15) The medicament for simultaneously or sequentially administering the compound represented by the formula (I) in (1), its pharmaceutically acceptable salt or a solvate thereof comprising a therapeutically effective amount of a compound having an anti-influenza activity, its pharmaceutically acceptable salt or a solvate thereof, and/or an antibody having an anti-influenza activity.

(16) The enhancer of the anti-influenza activity or medicament according to any one of (12) to (15), wherein a compound having an anti-influenza activity, its pharmaceutically acceptable salt or a solvate thereof, and/or an antibody having an anti-influenza activity is at least one compound selected from the group consisting of Oseltamivir, Zanamivir, Perramivir, Laninamivir, Favipiravir, Amantazine, Flumazine, VX-787 and MHAA4549A.

(17) A medicament characterized in that (A) a compound having a cap-dependent endonuclease inhibitory activity, its pharmaceutically acceptable salt or a solvate thereof, is combined with (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof.

(18) An enhancer of the anti-influenza activity of (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof comprising a compound having a cap-dependent endonuclease inhibitory activity, its pharmaceutically acceptable salt or a solvate thereof.

(19) An enhancer of the anti-influenza activity of a compound having a cap-dependent endonuclease inhibitory activity, its pharmaceutically acceptable salt or a solvate thereof comprising (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof.

(20) A medicament for simultaneously or sequentially administering (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof comprising a therapeutically effective amount of a compound having a cap-dependent endonuclease inhibitory activity, its pharmaceutically acceptable salt or a solvate thereof.

(21) A medicament for simultaneously or sequentially administering a compound having a cap-dependent endonuclease inhibitory activity, its pharmaceutically acceptable salt or a solvate thereof comprising a therapeutically effective amount of (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof.

(22) A method of treating influenza comprising the steps of administering in combination (A) a compound represented by the formula (I);

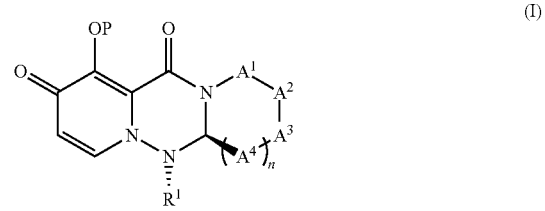

wherein
P is hydrogen or a group to form a prodrug;
$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is each independently $CR^{4A}R^{4B}$, S or O;
the number of hetero atoms among atoms constituting the ring which consists of $A^1, A^2, A^3, A^4$, nitrogen atom adjacent to $A^1$ and carbon atom adjacent to $A^4$ is 1 or 2;
$R^{1A}$ and $R^{1B}$ are each independently hydrogen, halogen, alkyl, haloalkyl, alkyloxy or phenyl;
$R^{2A}$ and $R^{2B}$ are each independently hydrogen, halogen, alkyl, haloalkyl, alkyloxy or phenyl;
$R^{3A}$ and $R^{3B}$ are each independently hydrogen, halogen, alkyl, haloalkyl, alkyloxy or phenyl;

$R^{4A}$ are each independently hydrogen, halogen, alkyl, haloalkyl, alkyloxy or phenyl;

$R^{4B}$ are each independently hydrogen, halogen, alkyl, haloalkyl, alkyloxy or phenyl;

$R^{3A}$ and $R^{3B}$ may be taken together with an adjacent carbon atom to form non-aromatic carbocycle or non-aromatic heterocycle;

n is any integer of 1 to 2; and $R^1$ is

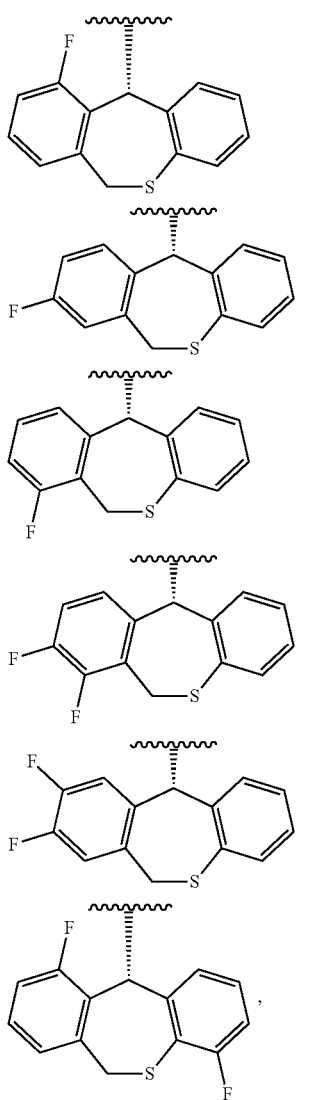

its pharmaceutically acceptable salt or a solvate thereof, and (B) compound(s) having an anti-influenza activity or its pharmaceutically acceptable salt or a solvate thereof, and/or an antibody having an anti-influenza activity, in a therapeutically effective amount thereof to an individual in need of treatment for influenza.

(23) A medicament for use in the treatment of influenza, characterized in that (A) a compound represented by the formula (I):

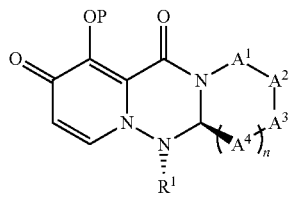

wherein P is hydrogen or a group to form a prodrug;

$A^1$ is $CR^{1A}R^{1B}$, S or O;

$A^2$ is $CR^{2A}R^{2B}$, S or O;

$A^3$ is $CR^{3A}R^{3B}$, S or O;

$A^4$ is each independently $CR^{4A}R^{4B}$, S or O;

the number of hetero atoms among atoms constituting the ring which consists of $A^1, A^2, A^3, A^4$, nitrogen atom adjacent to $A^1$ and carbon atom adjacent to $A^4$ is 1 or 2;

$R^{1A}$ and $R^{1B}$ are each independently hydrogen, halogen, alkyl, haloalkyl, alkyloxy or phenyl;

$R^{2A}$ and $R^{2B}$ are each independently hydrogen, halogen, alkyl, haloalkyl, alkyloxy or phenyl;

$R^{3A}$ and $R^{3B}$ are each independently hydrogen, halogen, alkyl, haloalkyl, alkyloxy or phenyl;

$R^{4A}$ are each independently hydrogen, halogen, alkyl, haloalkyl, alkyloxy or phenyl;

$R^{4B}$ are each independently hydrogen, halogen, alkyl, haloalkyl, alkyloxy or phenyl;

$R^{3A}$ and $R^{3B}$ may be taken together with an adjacent carbon atom to form non-aromatic carbocycle or non-aromatic heterocycle;

n is any integer of 1 to 2; and $R^1$ is

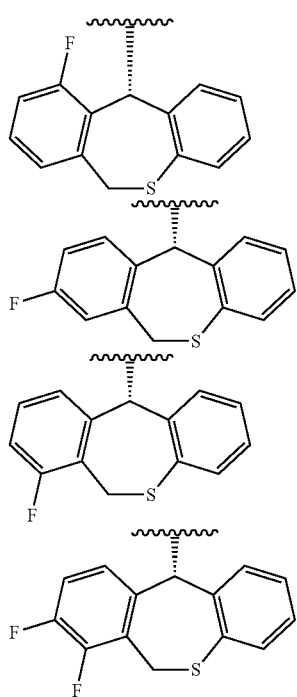

13

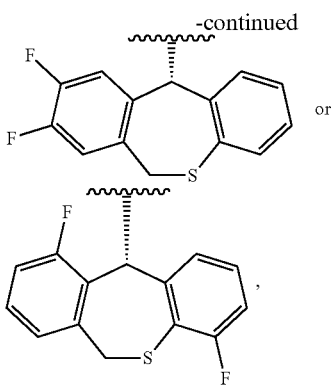

or

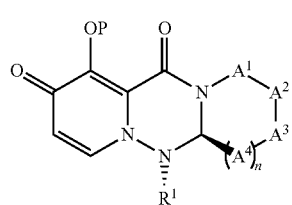

, its pharmaceutically acceptable salt or a solvate thereof, is combined with (B) compound(s) having anti-influenza activity, or its pharmaceutically acceptable salt or a solvate thereof, and/or an antibody having an anti-influenza activity.

Effect of the Invention

The medicament of the present invention is useful as a treatment and/or prevention of influenza infection.

BRIEF DESCRIPTION OF DRAWINGS

FIG. 1 is a result of measuring the plasma concentration of Compound III-1, after oral administration of prodrug Compound II-4, the parent compound of which is Compound III-1, to rat under non-fasting conditions.

FIG. 2 is a result of measuring the plasma concentration of Compound II-4, after oral administration of prodrug Compound II-4, the parent compound of which is Compound III-1, to rat under non-fasting conditions.

BEST MODE FOR CARRYING OUT THE INVENTION

The meaning of each term used in the present description is explained below. Each term is used in a unified sense, and is used in the same sense when used alone, or when used in combination of other term.

The term of "consisting of" means having only components.

The term of "comprising" means not restricting with components and not excluding undescribed factors.

The present invention is a medicament, characterized in that (A) a compound represented by the formula (I):

(I)

wherein
P is hydrogen or a group to form a prodrug;
$A^1$ is $CR^{1A}R^{1B}$, S or O;
$A^2$ is $CR^{2A}R^{2B}$, S or O;

14

$A^3$ is $CR^{3A}R^{3B}$, S or O;
$A^4$ is each independently $CR^{4A}R^{4B}$, S or O;
the number of hetero atoms among atoms constituting the ring which consists of $A^1$, $A^2$, $A^3$, $A^4$, nitrogen atom adjacent to $A^1$ and carbon atom adjacent to $A^4$ is 1 or 2;
$R^{1A}$ and $R^{1B}$ are each independently hydrogen, halogen, alkyl, haloalkyl, alkyloxy or phenyl;
$R^{2A}$ and $R^{2B}$ are each independently hydrogen, halogen, alkyl, haloalkyl, alkyloxy or phenyl;
$R^{3A}$ and $R^{3B}$ are each independently hydrogen, halogen, alkyl, haloalkyl, alkyloxy or phenyl;
$R^{4A}$ are each independently hydrogen, halogen, alkyl, haloalkyl, alkyloxy or phenyl;
$R^{4B}$ are each independently hydrogen, halogen, alkyl, haloalkyl, alkyloxy or phenyl;
$R^{3A}$ and $R^{3B}$ may be taken together with an adjacent carbon atom to form non-aromatic carbocycle or non-aromatic heterocycle;
n is any integer of 1 to 2; and
$R^1$ is

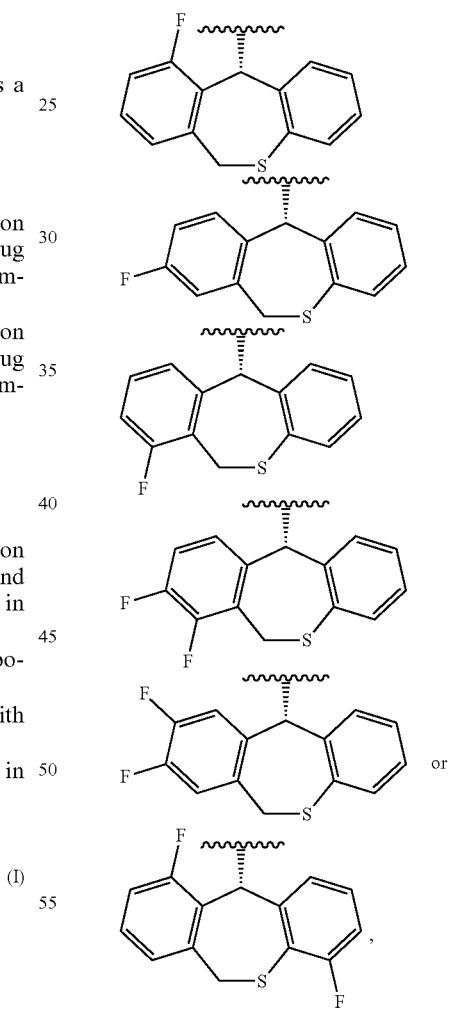

its pharmaceutically acceptable salt or a solvate thereof, is combined with (B) compound(s) having an anti-influenza activity, its pharmaceutically acceptable salt or a solvate thereof, and/or an antibody having an anti-influenza activity.

As (A), among the compound represented by the formula (I), its pharmaceutically acceptable salt or a solvate thereof, the compound wherein the group represented by formula:

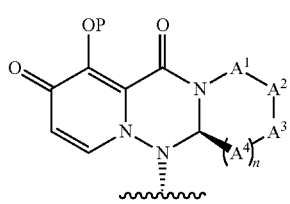

is

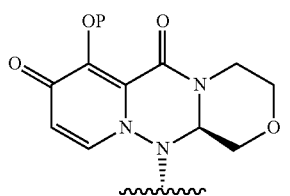

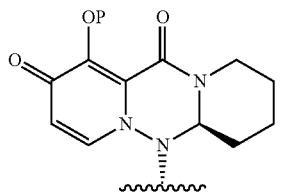

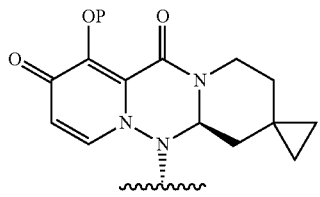

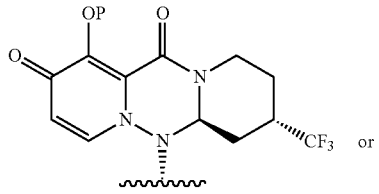

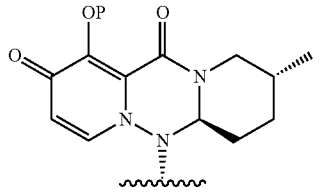

wherein each definition has the same meanings as described (1), its pharmaceutically acceptable salt or a solvate thereof is preferable.

Especially the compound wherein it is a group represented by formula:

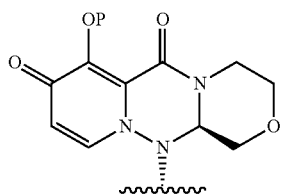

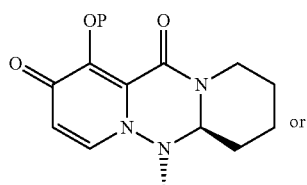

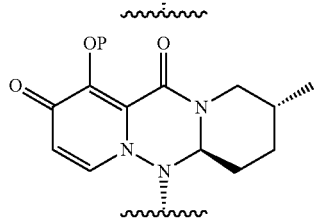

is preferable, and furthermore the compound wherein it is a group represented by formula:

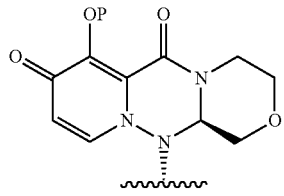

is preferable.

As (A), among the compound represented by the formula (I), its pharmaceutically acceptable salt or a solvate thereof, the compound wherein R$^1$ is

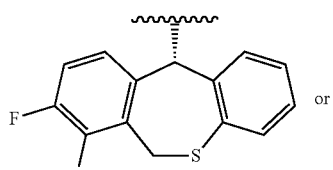

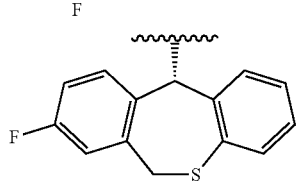

is also preferable, and furthermore the compound wherein it is

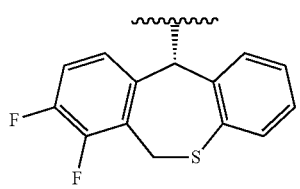 [SMILES: *[C@@H]1c2ccccc2SCc2c1ccc(F)c2F]

is preferable.

Especially the compound represented by formula:

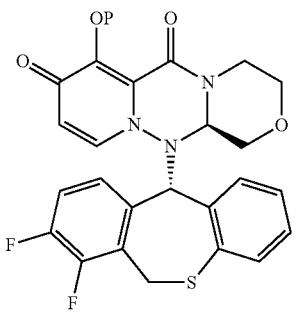

wherein P is hydrogen or a group to form a prodrug, and as a group of P to form a prodrug, it is preferably the group to form the prodrug according to the above (4), furthermore preferably the group for forming the prodrug according to the above (5); its pharmaceutically acceptable salt or a solvate thereof is preferable, and furthermore the compound represented by the formula:

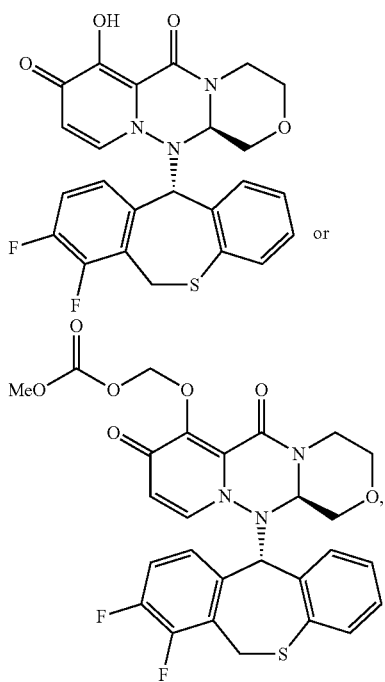

its pharmaceutically acceptable salt or a solvate thereof is preferable.

As the "compound(s) having an anti-influenza activity" and "antibody having an anti-influenza activity" of (B) to be combined with (A), the compound or antibody of which the $EC_{50}$ value which is measured according to the method described in Test Example 6 of Patent Document 1 is less than 100 μM, preferably less than 100 nM, can be used. However, the "compound having an anti-influenza activity, its pharmaceutically acceptable salt or a solvate thereof, and/or an antibody having an anti-influenza activity" used in (B) is different from a compound of formula (I), its pharmaceutically acceptable salt or a solvate thereof used as (A).

The term "compound having an anti-influenza activity" includes a compound having a neuraminidase inhibitory activity, a compound having a RNA-dependent RNA polymerase inhibitory activity, a compound having a M2 protein inhibitory activity, a compound having a PB2 Cap binding inhibitory activity, a HA maturation inhibitory activity, a recombinant sialidase, a compound having a re-assemble inhibitory activity, a compound having a RNA interference activity, a compound having a receptor of hemagglutinin binding inhibitory activity, a compound having a membrane of HA fusion inhibitory activity, a compound having a NP nuclear translocation inhibitory activity, a compound having a cap-dependent endonuclease (CEN) inhibitory activity, a compound having a CXCR inhibitory activity and a compound having a CRM1 inhibitory activity and the like. "Compound(s) having an anti-influenza activity" are not limited to ones that are commercially available or under development, but commercially available or under development include Oseltamivir, Zanamivir, Peramivir, Laninamivir, Favipiravir, Amantazine, Flumazine, VX-787, MHAA4549A, TCN-032, VIS-410, CR-8020, CR-6261, CT-P27, MEDI-8852 and the like. In particular, Oseltamivir, Zanamivir, Peramivir, Laninamivir, Fabipiravir, Amantazine, Flumadin and VX-787 are preferred. Furthermore, Oseltamivir, Zanamivir, Peramivir, Laninamivir and VX-787 are preferred.

The "compound having anti-influenza activity" includes a compound having a mechanism of action different from that of the compound of the formula (I), its pharmaceutically acceptable salt or a solvate thereof used as (A). That is a compound other than a compound having a cap-dependent endonuclease (CEN) inhibitory activity is preferred.

The "compound having anti-influenza activity" is preferably a compound having a neuraminidase inhibitory activity, a compound having a RNA-dependent RNA polymerase inhibitory activity, a compound having a M2 protein inhibitory activity, a compound having a PB2 Cap binding inhibitory activity or a compound having a re-assemble inhibitory activity, more preferably, a compound having a neuraminidase inhibitory activity or a compound having a PB2 Cap binding inhibiting activity, particularly preferably Oseltamivir, Zanamivir, Peramivir, Laninamivir or VX-787.

"An antibody having an anti-influenza activity" includes an HA antibody and the like.

The term "a compound having a neuraminidase inhibitory activity" means the compound has a neuraminidase inhibitory activity and may be any compound which as long as falls into the scope of the above "compound(s) having an anti-influenza activity". Also, it may be prodrug forms thereof.

"A compound having a neuraminidase inhibitory activity" includes, for example, the compound(s) described below, but it is not limited to them:

(−)-Ethyl(3R,4R,5S)-4-Acetamido-5-amino-3-(1-ethyl-propoxy)cyclohex-1-ene-1-carboxylate, (+)-(4S,5R,6R)-5-Acetylamino-4-guanidino-6-[(1R,2R)-1,2,3-trihydroxypropyl]-5,6-dihydro-4H-pyran-2-carboxylic acid, (1S,2S,3R,4R)-3-[(1S)-1-(Acetylamino)-2-ethylbutyl]-4-guanidino-2-hydroxycyclopentanecarboxylic acid, (2R,3R,4S)-3-Acetamido-4-guanidino-2-[(1R,2R)-2-hydroxy-1-methoxy-3-(octanoyloxy)propyl]-3,4-dihydro-2H-pyran-6-carboxylic acid, or (2R,3R,4S)-3-Acetamido-4-guanidino-2-[(1S,2R)-3-hydroxy-1-methoxy-2-(octanoyloxy)propyl]-3,4-dihydro-2H-pyran-6-carboxylic acid.

"A compound having a neuraminidase inhibitory activity, its pharmaceutically acceptable salt or a solvate thereof" includes preferably Oseltamivir, Oseltamivir phosphate (trade name: Tamiflu), Zanamivir, Zanamivir hydrate (trade name: Relenza), Peramivir (trade name: Rapiacta), Luninamivir, Laninamibyl octanoate ester hydrate (trade name: Innavir) and the like.

The term "a compound having a RNA-dependent RNA polymerase inhibitory activity" means the compound has a RNA-dependent RNA polymerase inhibitory activity and may be any compound which as long as falls into the scope of the above "compound(s) having an anti-influenza activity". Also, it may be prodrug forms thereof.

"A compound having a RNA-dependent RNA polymerase inhibitory activity" include, for example, the compound described below, but it is not limited to them:
6-Fluoro-3-hydroxypyrazine-2-carboxamide.

"A compound having a RNA-dependent RNA polymerase inhibitory activity, its pharmaceutically acceptable salt or a solvate thereof" includes preferably Fabipiravir (trade name: Abigan) and the like.

The term "a compound having a M2 protein inhibitory activity" means the compound has an activity of inhibiting the enucleation process of the virus and may be any compound which as long as falls into the scope of the above "compound(s) having an anti-influenza activity". Also, it may be prodrug forms thereof. "A compound having a M2 protein inhibitory activity" also includes a compound having a M2 ion-channel inhibitory activity.

"A compound having a M2 protein inhibitory activity" includes, for example, the compound described below, but it is not limited to them:
Tricyclo[3.3.1.1$^{3,7}$]dec-1-ylamine, or
α-methyl-1-adamantanemethylamine.

"A compound having a M2 protein inhibitory activity, its pharmaceutically acceptable salt or a solvate thereof" includes preferably Amantadine, Amantadine hydrochloride (trade name: Symmetrel) or Rimantadine (trade name: Flumazine) and the like.

The term "a compound having a PB2 Cap binding inhibitory activity" means the compound has the activity of inhibiting the cap-snatching reaction of the PB2 subunit of the influenza A polymerase complex and may be any compound which as long as falls into the scope of the above "compound(s) having an anti-influenza activity". Also, it may be prodrug forms thereof.

"A compound having a PB2 Cap binding inhibitory activity" includes, for example, the compound described below, but it is not limited thereto:
(2S,3S)-3-((5-Fluoro-2-(5-fluoro-1H-pyrrolo[2,3-b]pyridin-3-yl)pyrimidin-4-yl)amino)bicyclo[2.2.2]octane-2-carboxylic Acid.

"A compound having a PB2 Cap binding inhibitory activity, its pharmaceutically acceptable salt or a solvate thereof" includes preferably VX-787(JNJ-872) and the like, but it is not limited to them.

The term "a compound having a HA maturation inhibitory activity" means the compound has a HA maturation inhibitory activity and may be any compound which as long as falls into the scope of the above "compound(s) having an anti-influenza activity". Also, it may be prodrug forms thereof.

"A compound having a HA maturation inhibitory activity, its pharmaceutically acceptable salt or a solvate thereof" includes Tizoxanide and the like, but it is not limited to them.

The term "a recombinant sialidase" means a recombinant fusion protein consisting of a sialidase and a domain anchoring to the cell follicle and may be any compound which as long as falls into the scope of the above "compound(s) having an anti-influenza activity". Also, it may be prodrug forms thereof.

"A recombinant sialidase, its pharmaceutically acceptable salt or a solvate thereof" preferably includes DAS-181 and the like.

The term "a compound having a re-assemble inhibitory activity" means the compound has a re-assemble inhibitory activity and may be any compound which as long as falls into the scope of the above "compound(s) having an anti-influenza activity". Also, it may be prodrug forms thereof.

"A compound having a re-assemble inhibitory activity, its pharmaceutically acceptable salt or a solvate thereof" preferably includes BTL-TML-001 and the like.

The term "a compound having a RNA interference inhibitory activity" means the compound has a RNA interference inhibitory activity and may be any compound which as long as falls into the scope of the above "compound(s) having an anti-influenza activity". Also, it may be prodrug forms thereof.

"A compound having a RNA interference inhibitory activity, its pharmaceutically acceptable salt or a solvate thereof" preferably includes Radavirsen and the like.

The term "a compound having a receptor of hemagglutinin binding inhibitory activity" means the compound has a receptor of hemagglutinin binding inhibitory activity and may be any compound which as long as falls into the scope of the above "compound(s) having an anti-influenza activity".

The term "a compound having a membrane of HA fusion inhibitory activity" means the compound has a membrane of HA fusion inhibitory activity and may be any compound which as long as falls into the scope of the above "compound(s) having an anti-influenza activity". Here, HA means hemagglutinin.

The term "a compound having a NP nuclear translocation inhibitory activity" means the compound has a NP nuclear translocation inhibitory activity and may be any compound which as long as falls into the scope of the above "compound(s) having an anti-influenza activity". Here, NP means nucleoprotein.

The term "a compound having a CXCR inhibitory activity" means the compound has a CXCR inhibitory activity and may be any compound which as long as falls into the scope of the above "compound(s) having an anti-influenza activity". Also, it may be prodrug forms thereof.

"A compound having a CXCR inhibitory activity, its pharmaceutically acceptable salt or a solvate thereof" preferably includes Danirixin (GSK-1325756) and the like.

The term "a compound having a CRM1 inhibitory activity" means the compound has a CRM1 inhibitory activity and may be any compound which as long as falls into the scope of the above "compound(s) having an anti-influenza activity". Also, it may be prodrug forms thereof.

"A compound having a CRM1 inhibitory activity, its pharmaceutically acceptable salt or a solvate thereof" preferably includes Verdinexor (KPT-335) and the like, "A compound having a cap-dependent endonuclease inhibitory activity" may be any compound as long as it has a CEN inhibitory activity. For example, the compound of which the $IC_{50}$ value which is measured according to the method described in Test Example 1 of Patent Document 1 is less than 1 μM, preferably less than 10 nM, can be used.

Examples of "an anti-HA antibody" includes MHAA4549A, TCN-032, VIS-410, CR-8020, CR-6261, CT-P27 or MEDI-8852 but are not limited to them.

"Compound(s) having an anti-influenza activity, its pharmaceutically acceptable salt or a solvate thereof and/or an antibody having an anti-influenza activity" may be one or more agents, but not limited to one agent.

The compound represented by formula (I) in (A), its pharmaceutically acceptable salt or a solvate thereof is described below.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

A preferred embodiment of "alkenyl" is vinyl, allyl, propenyl, isopropenyl or butenyl.

The term "alkylene" includes a C1 to C15, preferably a C1 to C10, more preferably a C1 to C6 and further preferably a C1 to C4 liner or branched bivalent hydrocarbon group. Examples include methylene, ethylene, trimethylene, propylene, tetramethylene, pentamethylene, and hexamethylene.

The term "alkenylene" includes a C2 to C15, preferably a C2 to C10, more preferably a C2 to C6 and further preferably a C2 to C4 liner or branched bivalent hydrocarbon group having one or more double bond(s) at any position(s). Examples include vinylene, prenylene, butenylene, and pentenylene.

The term "hydroxyalkyl" means a group wherein one or more hydroxyl group(s) is replaced with hydrogen atom(s) attached to a carbon atom(s) of the above "alkyl". Examples include hydroxymethyl, 1-hydroxyethyl, 2-hydroxyethyl, 1-hydroxypropyl, 2-hydroxypropyl, and 1,2-hydroxyethyl.

A preferred embodiment of "hydroxyalkyl" is hydroxymethyl.

The term "alkyloxy" means a group wherein the above "alkyl" is bonded to an oxygen atom. Examples include methyloxy, ethyloxy, n-propyloxy, isopropyloxy, n-butyloxy, tert-butyloxy, isobutyloxy, sec-butyloxy, pentyloxy, isopentyloxy, and hexyloxy.

A preferred embodiment of "alkyloxy" is methyloxy, ethyloxy, n-propyloxy, isopropyloxy or tert-butyloxy.

The term "haloalkyl" means a group wherein one or more "halogen" described above is bonded to the above "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropan-2-yl.

A preferred embodiment of "haloalkyl" is trifluoromethyl or trichloromethyl.

The term "alkylcarbonyl" means a group wherein the above "alkyl" is bonded to a carbonyl group. Examples include methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, and hexylcarbonyl.

A preferred embodiment of "alkylcarbonyl" is methylcarbonyl, ethylcarbonyl or n-propylcarbonyl.

The term "alkylamino" means a group wherein one or two hydrogen atom(s) attached to a nitrogen atom of an amino group is replaced with the above "alkyl". Two alkyl groups may be the same or different. Examples include methylamino, ethylamino, isopropylamino, dimethylamino, diethylamino, N,N-diisopropylamino, N-methyl-N-ethylamino, and N-isopropyl-N-ethylamino.

A preferred embodiment of "alkylamino" is methylamino, ethylamino, dimethylamino or diethylamino.

The term "alkylaminoalkyl" means a group wherein the above "alkylamino" is bonded to the above "alkyl".

The term "alkylaminocarbonyl" means a group wherein the above "alkylamino" is bonded to a carbonyl group.

The term "alkylaminocarbonyloxy" means a group wherein the above "alkylaminocarbonyl" is bonded to an oxygen atom.

The term "alkylcarbonylamino" means a group wherein the above "alkylcarbonyl" is replaced with a hydrogen atom bonded to a nitrogen atom of an amino group. Examples include methylcarbonylamino, ethylcarbonylamino, propylcarbonylamino, isopropylcarbonylamino, tert-butylcarbonylamino, isobutylcarbonylamino, and sec-butylcarbonylamino.

A preferred embodiment of "alkylcarbonylamino" is methylcarbonylamino or ethylcarbonylamino.

The term "alkylcarbonyloxy" means a group wherein the above "alkylcarbonyl" is bonded to an oxygen atom. Examples include methylcarbonyloxy, ethylcarbonyloxy, propylcarbonyloxy, isopropylcarbonyloxy, tert-butylcarbonyloxy, isobutylcarbonyloxy, and sec-butylcarbonyloxy.

A preferred embodiment of "alkylcarbonyloxy" is methylcarbonyloxy or ethylcarbonyloxy.

The term "alkylcarbonylaminoalkyl" means a group wherein the above "alkylcarbonylamino" is bonded to the above "alkyl".

The term "alkyloxycarbonyl" means a group wherein the above "alkyloxy" is bonded to a carbonyl group. Examples include methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, and hexyloxycarbonyl.

A preferred embodiment of "alkyloxycarbonyl" is methyloxycarbonyl, ethyloxycarbonyl or propyloxycarbonyl.

The term "alkyloxycarbonylalkyl" means a group wherein the above "alkyloxycarbonyl" is bonded to the above "alkyl".

The term "alkyloxycarbonyloxy" means a group wherein the above "alkyloxycarbonyl" is bonded to an oxygen atom.

The term "alkylsulfanyl" means a group wherein the above "alkyl" is replaced with a hydrogen atom bonded to a sulfur atom of a sulfanyl group. Examples include methylsulfanyl, ethylsulfanyl, n-propylsulfanyl, and isopropylsulfanyl.

The term "alkylsulfonyl" means a group wherein the above "alkyl" is bonded to a sulfonyl group. Examples include methylsulfonyl, ethylsulfonyl, propylsulfonyl, isopropylsulfonyl, tert-butylsulfonyl, isobutylsulfonyl, and sec-butylsulfonyl.

A preferred embodiment of "alkylsulfonyl" is methylsulfonyl or ethylsulfonyl.

The term "trialkylsilyl" means a group wherein three of the above "alkyl" are bonded to a silicon atom. Three alkyl groups may be the same or different. Examples include trimethylsilyl, triethylsilyl, and tert-butyldimethylsilyl.

The term "carbocyclyl group" means C3 to C20 preferably C3 to C16, more preferably C4 to C12 cyclic hydrocarbon group and includes aromatic carbocyclyl and non-aromatic carbocyclyl.

The term "aromatic carbocyclyl" means a cyclic aromatic hydrocarbon group which is monocyclic or polycyclic having two or more rings. Examples include phenyl, naphthyl, anthryl, and phenanthryl.

A preferred embodiment of "aromatic carbocyclyl" is phenyl, 1-naphthyl or 2-naphthyl. Another embodiment of "aromatic carbocyclyl" is phenyl, The term "non-aromatic carbocyclyl" means a cyclic saturated hydrocarbon group or a cyclic unsaturated non-aromatic hydrocarbon group, which is monocyclic or polycyclic having two or more rings. Examples of the "non-aromatic carbocyclyl", which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

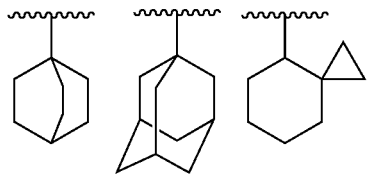

The non-aromatic carbocyclyl which is monocyclic is preferably C3 to C16, more preferably C3 to C12 and further preferably C3 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The non-aromatic carbocyclyl which is polycyclic having two or more rings is preferably C8 to C13, more preferably C9 to C10 carbocyclyl. Examples include indanyl, indenyl, acenaphthyl, tetrahydronaphthyl, and fluorenyl.

The term "carbocycle" means C3 to C20 preferably C3 to C16, more preferably C4 to C12 cyclic hydrocarbon and includes aromatic carbocycle and non-aromatic carbocycle.

The term "aromatic carbocycle" means a cyclic aromatic hydrocarbon which is monocyclic or polycyclic having two or more rings. Examples include benzene ring, naphthalene ring, anthracene ring, and phenanthrene ring.

A preferred embodiment of "aromatic carbocycle" is benzene ring and naphthalene ring are exemplified. Another embodiment of "aromatic carbocycle" is benzene ring.

The term of "non-aromatic carbocycle" means a saturated carbocycle or an unsaturated non-aromatic carbocycle which is monocyclic or polycyclic having two or more rings. Examples of the "non-aromatic carbocycle" which is polycyclic having two or more rings, include a fused ring wherein a non-aromatic carbocycle, which is monocyclic or polycyclic having two or more rings, is fused with a ring of the above "aromatic carbocycle".

In addition, examples of the "non-aromatic carbocycle" also include a cycle having a bridge or a cycle to form a spiro ring as follows:

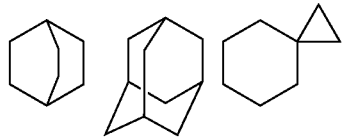

The non-aromatic carbocycle which is monocyclic is preferably C3 to C16, more preferably C3 to C12 and further preferably C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, and cyclohexadiene.

The non-aromatic carbocycle which is polycyclic having two or more rings is preferably C8 to C13, more preferably C9 to C10 carbocycle. Examples include indane, indene, acenaphthalene, tetrahydronaphthalene, and fluorine.

The term "heterocyclyl group" includes an aromatic cyclyl and a non-aromatic heterocyclyl, which is containing one or more of heteroatom(s) selected independently from O, S and N.

The term "aromatic heterocyclyl" means an aromatic cyclyl, which is monocyclic or polycyclic having two or more rings, containing one or more of heteroatom(s) selected independently from O, S and N.

The term "aromatic heterocyclyl", which is polycyclic having two or more rings, include a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

The aromatic heterocyclyl, which is bicyclic, is preferably a 8- to 18-membered and more preferably 9- or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

The aromatic heterocyclyl, which is polycyclic having three or more rings, is preferably a 11- to 26-membered and more preferably 13- or 14-membered ring. Examples include carbazolyl, acridinyl, xanthenyl, phenothiazinyl, phenoxathiinyl, phenoxazinyl, and dibenzofuryl.

The term "non-aromatic heterocyclyl" means a non-aromatic cyclyl, which is monocyclic or polycyclic having two or more rings, containing one or more heteroatom(s) selected independently from O, S and N.

Examples of "non-aromatic heterocyclyl", which is polycyclic having two or more rings, include a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl".

In addition, examples of the "non-aromatic heterocyclyl" also include a group having a bridge or a group to form a spiro ring as follows:

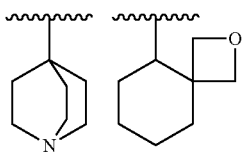

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, tetrahydrothiazolinyl, tetrahydroisothiazolinyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, and thiazinyl.

The non-aromatic heterocyclyl, which is polycyclic having two or more rings, is preferably a 8- to 20-membered and more preferably 8- to 16-membered ring. Examples include indolinyl, isoindolinyl, chromanyl, and isochromanyl.

The term "heterocycle" includes an aromatic cycle and a non-aromatic heterocycle, which is containing one or more of heteroatom(s) selected independently from O, S and N.

The term of "aromatic heterocycle" means an aromatic cycle which is monocyclic or polycyclic having two or more rings, containing one or more of heteroatom(s) selected independently from O, S and N.

Examples of "aromatic heterocycle", which is polycyclic having two or more rings, include a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered and more preferably 5- to 6-membered ring. Examples include pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, and thiadiazole.

The aromatic heterocycle, which is bicyclic, is preferably a 8- to 18-membered and more preferably 9- to 10-membered ring. Examples include indoline, isoindoline, indazorin, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, and thiazolopyridine.

The aromatic heterocycle, which is polycyclic having three or more rings, is preferably a 11- to 26-membered and more preferably 13- to 14-membered ring. Examples include carbazole, acridine, xanthene, phenothiazine, phenoxathiin, phenoxazine, and dibenzofuran.

The term "non-aromatic heterocycle" means a non-aromatic cycle, which is monocyclic or polycyclic having two or more rings, containing one or more of heteroatom(s) selected independently from O, S and N.

Examples of "non-aromatic heterocycle", which is polycyclic having two or more rings, include a fused ling wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, examples of "non-aromatic heterocycle" also include a cycle having a bridge or a cycle to form a spiro ring as follows:

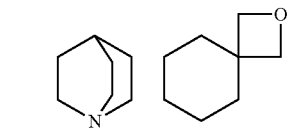

The non-aromatic heterocycle, which is monocyclic, is preferably a 3- to 8-membered and more preferably 5- to 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazoline, tetrahydrothiazoline, tetrahydroisothiazoline, dihydrooxazine, hexahydroazepine, tetrahydrodiazepine, tetrahydropyridazine, hexahydropyrimidine, dioxolane, dioxazine, aziridine, dioxoline, oxepane, thiolane, and thiazine.

Examples of non-aromatic heterocycle, which is polycyclic having two or more rings, include indoline, isoindoline, chroman, and isochroman.

The term "spiro ring" includes the above non-aromatic carbocyclic ring and the above non-aromatic heterocyclic ring bonded to one atom.

The "carbocycle" part of "carbocyclylalkyl", "carbocyclyloxy" or "carbocyclylamino" is same as the above "carbocycle".

The "heterocycle" part of "heterocyclylalkyl", "heterocyclyloxy" or "heterocyclylamino" is same as the above "heterocycle".

"Optionally substituted by substituent group A" means that an arbitrary position may be substituted by one, two or more same or different substituents selected from substituent group A.

"Optionally substituted by substituent group B" means that an arbitrary position may be substituted by one, two or more same or different substituents selected from substituent group B.

"Prodrug" in the present description refers to a compound represented by formula (II) in the following reaction formula:

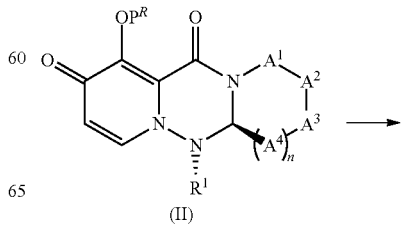

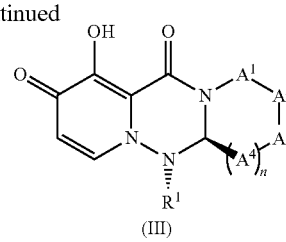

(III)

wherein $P^R$ is a group to form a prodrug; each symbol is same as the above, or its pharmaceutically acceptable salt, and means a compound showing cap-dependant endonuclease (CEN) inhibitory activity and/or CPE inhibitory effect by being converted into a compound represented by formula (III) by a decomposition reaction caused by drug-metabolizing enzymes, hydrolases, gastric acids, enterobacteria, etc. under physiological conditions in vivo.

The prodrug more preferably means a compound in which bioavailability and/or AUC (area under the blood concentration curve) in in vivo administration is improved more than those of the compound represented by formula (III).

Therefore, the prodrug is efficiently absorbed into the body in the stomach and/or intestines after in vivo administration (for example, oral administration), then converted into the compound represented by formula (III). Thus, the prodrug preferably shows an effect of treating and/or preventing influenza higher than the compound represented by formula (III).

"Group to form a prodrug" in the present description refers to a "PR" group in the formula (II), in the following reaction formula:

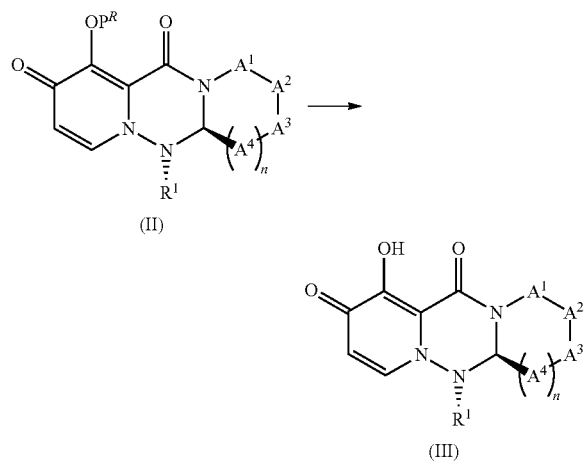

wherein each symbol is same as the above,
and —$OP^R$ group is converted into —OH group in the formula (III) by a decomposition reaction caused by drug-metabolizing enzymes, hydrolases, gastric acids, enterobacteria, etc. under physiological conditions in vivo.

The "group to form a prodrug" more preferably means a group that improves bioavailability and/or AUC (area under the blood concentration curve) of the compound represented by formula (III) by being added to the compound represented by formula (III).

The group to form a prodrug includes the groups described in Prog. Med. 5: 2157-2161 (1985) and Supplied by The British Library—"The world's Knowledge", and the groups to form a prodrug as described below.

The "$P^R$" in —$OP^R$ group in the formula (I) or (II) may be a group converted into —OH group in vivo, and examples preferably include a group selected from the following formulas.

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —(C($P^{R3}$)$_2$)$_p$—$P^{R6}$,
w) —C(=N$^+$($P^{R7}$)$_2$)(—N($P^{R7}$)$_2$),
x) —(C($P^{R3}$)$_2$)$_q$—C(=O)—O—$P^{R2}$,
x') —(C($P^{R3}$)$_2$)$_q$—C(=O)—N(—K)—$P^{R4}$,
x") —(C($P^{R3}$)$_2$)$_q$—C(=O)—$P^{R1}$,
y) —C($P^{R3}$)$_2$—N(—K)—C(=O)—O—$P^{R2}$,
z) —P(=O)(—$P^{R8}$)(—$P^{R9}$),
aa) —S(=O)$_2$$P^{R10}$,
ab) —$P^{R11}$,
ac) —(C($P^{R3}$)$_2$)$_r$—O—$P^{R12}$, and
ad) —(C($P^{R3}$)$_2$)$_t$—N(—K)—$P^{R13}$,
wherein L is straight or branched alkylene optionally substituted by substituent group B, or straight or branched alkenylene optionally substituted by substituent group B;
K is hydrogen, or alkyl optionally substituted by substituent group A;
$P^{R0}$ is alkyl optionally substituted by substituent group A, or alkenyl optionally substituted by substituent group A;
$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
$P^{R3}$ is each independently hydrogen, alkyl or hydroxy;
two $P^{R3}$ on adjacent carbon atom may be taken together to form alkenylene or alkylene;
$P^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;

$P^{R5}$ is each independently hydroxy or OBn;
$P^{R6}$ is carbocyclyl group optionally substituted by substituent group A, or heterocyclyl group optionally substituted by substituent group A;
$P^{R7}$ is each independently alkyl optionally substituted by substituent group A;
$P^{R8}$ is alkyloxy optionally substituted by substituent group A;
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or
$P^{R8}$ and $P^{R9}$ may be taken together with an adjacent phosphorus atom to form heterocycle optionally substituted by substituent group A;
$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;
$P^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;
$P^{R12}$ is each independently hydrogen or alkyl optionally substituted by substituent group A;
$P^{R13}$ is alkylsulfonyl optionally substituted by substituent group A;
p is any integer of 2 to 3;
q is any integer of 1 to 2;
r is any integer of 2 to 4; and
t is any integer of 2 to 4;
Substituent group A: oxo, alkyl, alkenyl, haloalkyl, hydroxyalkyl, amino, alkylamino, carbocyclyl group, heterocyclyl group, carbocyclylalkyl, Spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho; Substituent group B: Spiro ring and halogen.

In another embodiment, examples preferably include a group selected from the following formulas.
a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —(C($P^{R3}$)$_2$)$_p$—$P^{R6}$,
w) —C(=N$^+$($P^{R7}$)$_2$)(—N($P^{R7}$)$_2$),
x) —(C($P^{R3}$)$_2$)$_q$—C(=O)—O—$P^{R2}$,
x') —(C($P^{R3}$)$_2$)$_q$—C(=O)—N(—K)—$P^{R4}$,
x") —(C($P^{R3}$)$_2$)$_q$—C(=O)—$P^{R1}$,
y) —C($P^{R3}$)$_2$—N(—K)—C(=O)—O—$P^{R2}$,
z) —P(=O)(—$P^{R8}$)(—$P^{R9}$),
aa) —S(=O)$_2$$P^{R10}$,
ab) —$P^{R11}$,
ac) —(C($P^{R3}$)$_2$)$_r$—O—$P^{R12}$, and
ad) —(C($P^{R3}$)$_2$)$_t$—N(—K)—$P^{R13}$,
wherein L is straight or branched alkylene, or straight or branched alkenylene;
K is hydrogen, or alkyl optionally substituted by substituent group A;
$P^{R0}$ is alkyl optionally substituted by substituent group A, or alkenyl optionally substituted by substituent group A;
$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
$P^{R3}$ is each independently hydrogen or alkyl;
$P^{R4}$ is each independently alkyl optionally substituted by substituent group A, carbocyclyl group optionally substituted by substituent group A, heterocyclyl group optionally substituted by substituent group A, alkyl amino optionally substituted by substituent group A, carbocyclylalkyl optionally substituted by substituent group A, heterocyclylalkyl optionally substituted by substituent group A, or trialkylsilyl;
$P^{R5}$ is each independently hydroxy or OBn;
$P^{R6}$ is carbocyclyl group optionally substituted by substituent group A, or heterocyclyl group optionally substituted by substituent group A;
$P^{R7}$ is each independently alkyl optionally substituted by substituent group A;
$P^{R8}$ is alkyloxy optionally substituted by substituent group A;
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or
$P^{R8}$ and $P^{R9}$ may be taken together with an adjacent phosphorus atom to form heterocycle optionally substituted by substituent group A;
$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A; and
$P^{R11}$ is alkyl optionally substituted by substituent group A, alkenyl optionally substituted by substituent group A, carbocyclyl group optionally substituted by substituent group A, or heterocyclyl group optionally substituted by substituent group A;

Substituent group A; oxo, alkyl, hydroxyalkyl, amino, alkylamino, carbocyclyl group, heterocyclyl group, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkyl amino alkyl, alkyloxy, cyano, nitro, azido, alkylsulfonyl, trialkylsilyl and phospho.

The group to form a prodrug is preferably a group selected from the following formulas.

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —(C($P^{R3}$)$_2$)$_p$—$P^{R6}$,
w) —C(=N$^+$($P^{R7}$)$_2$)(—N($P^{R7}$)$_2$),
x) —(C($P^{R3}$)$_2$)$_q$—C(=O)—O—$P^{R2}$,
x') —(C($P^{R3}$)$_2$)$_q$—C(=O)—N(—K)—$P^{R4}$,
x") —(C($P^{R3}$)$_2$)$_q$—C(=O)—$P^{R1}$,
y) —C($P^{R3}$)$_2$—N(—K)—C(=O)—O—$P^{R2}$,
z) —P(=O)(—$P^{R8}$)(—$P^{R9}$),
aa) —S(=O)$_2$$P^{R10}$,
ab) —$P^{R11}$,
ac) —(C($P^{R3}$)$_2$)$_r$—O—$P^{R12}$, and
ad) —(C($P^{R3}$)$_2$)$_r$—N(—K)—$P^{R13}$, wherein L is straight or branched alkylene optionally substituted by substituent group B;

K is hydrogen, or alkyl optionally substituted by substituent group A;

$P^{R0}$ is alkyl optionally substituted by substituent group A;

$P^{R1}$ is carbocyclyl group optionally substituted by substituent group A, or heterocyclyl group optionally substituted by substituent group A;

$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;

$P^{R3}$ is each independently hydrogen, alkyl or hydroxy;

two $P^{R3}$ on adjacent carbon atom may be taken together to form alkenylene or alkylene;

$P^{R4}$ is alkyl optionally substituted by substituent group A, carbocyclyl group optionally substituted by substituent group A, or heterocyclyl group optionally substituted by substituent group A;

$P^{R5}$ is each independently hydroxy or OBn;

$P^{R6}$ is carbocyclyl group optionally substituted by substituent group A, or heterocyclyl group optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or $P^{R8}$ and $P^{R9}$ may be taken together with an adjacent phosphorus atom to form heterocycle optionally substituted by substituent group A;

$P^{R19}$ is alkyl optionally substituted by substituent group A, carbocyclyl group optionally substituted by substituent group A, or carbocyclylalkyl optionally substituted by substituent group A;

$P^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;

$P^{R12}$ is each independently hydrogen or alkyl optionally substituted by substituent group A;

$P^{R13}$ is alkylsulfonyl optionally substituted by substituent group A;

p is any integer of 2 to 3;
q is any integer of 1 to 2;
r is any integer of 2 to 4; and
t is any integer of 2 to 4;

Substituent group A: oxo, alkyl, alkenyl, alkylamino, carbocyclyl group, heterocyclyl group, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkyl aminocarbonyloxy, alkylamino alkyl, alkyloxy, cyano, nitro, azido, alkylsulfonyl, trialkylsilyl and phospho;

Substituent group B: spiro ring.

The group to form a prodrug is more preferably a group selected from the following formulas.

a) —C(=O)—$P^{R0}$,
b) —C(=O)—$P^{R1}$,
g) —C(=O)—O—$P^{R2}$,
h) —C(=O)—N(—K)($P^{R2}$),
i) —C(=O)—O-L-O—$P^{R2}$,
l) —C($P^{R3}$)$_2$—O—C(=O)—$P^{R4}$,
m) —C($P^{R3}$)$_2$—O—C(=O)—O—$P^{R4}$,
o) —C($P^{R3}$)$_2$—O—C(=O)—O-L-O—$P^{R4}$,
v) —(C($P^{R3}$)$_2$)$_p$—$P^{R6}$,
x) —(C($P^{R3}$)$_2$)$_q$—C(=O)—O—$P^{R2}$,
y) —C($P^{R3}$)$_2$—N(—K)—C(=O)—O—$P^{R2}$,
z) —P(=O)(—$P^{R8}$)(—$P^{R9}$), wherein L is straight or branched alkylene;

K is hydrogen, or alkyl optionally substituted by substituent group A;

$P^{R0}$ is alkyl optionally substituted by substituent group A;

$P^{R1}$ is carbocyclyl group optionally substituted by substituent group A, or heterocyclyl group optionally substituted by substituent group A;

$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
$P^{R3}$ is each independently hydrogen or alkyl;
$P^{R4}$ is alkyl optionally substituted by substituent group A, carbocyclyl group optionally substituted by substituent group A, or heterocyclyl group optionally substituted by substituent group A;
$P^{R6}$ is carbocyclyl group optionally substituted by substituent group A, or heterocyclyl group optionally substituted by substituent group A;
$P^{R8}$ is alkyloxy optionally substituted by substituent group A; and
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or
$P^{R8}$ and $P^{R9}$ may be taken together with an adjacent phosphorus atom to form heterocycle optionally substituted by substituent group A; Substituent group A: oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl, and trialkylsilyl.

"Converted into a prodrug" in the present description means that, as shown in the following reaction formula:

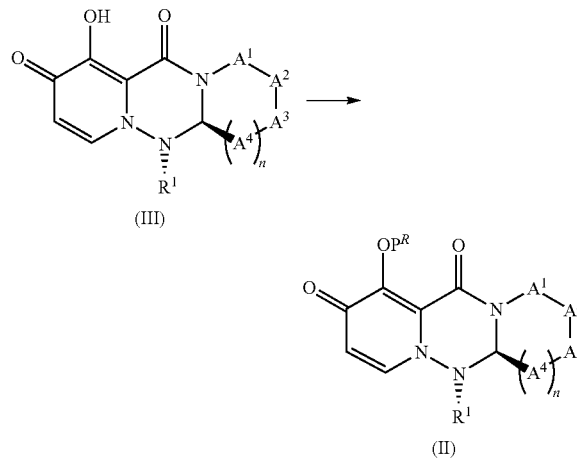

wherein each symbol is same as the above,
a hydroxy group in the formula (III), its pharmaceutically acceptable salt or solvate thereof is converted into —$OP^R$ group.

"Parent compound" in the present description means a compound to be a source before synthesizing the "prodrug" and/or a compound released from the "prodrug" by the reaction by enzymes, a gastric acid, and the like under physiological conditions in vivo, and specifically means a compound shown by the formula (III) or its pharmaceutically acceptable salt, or a solvate thereof.

The pharmaceutically acceptable salts of the compounds of the present invention include, for example, salts with alkaline metal (e.g., lithium, sodium or potassium), alkaline earth metal (e.g., calcium or barium), magnesium, transition metal (e.g., zinc or iron), ammonia, organic bases (e.g., trimethylamine, triethylamine, dicyclohexylamine, ethanolamine, diethanolamine, triethanolamine, meglumine, ethylenediamine, pyridine, picoline or quinoline) or amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid or ethanesulfonic acid). Especially, salts with hydrochloric acid, sulfuric acid, phosphoric acid, tartaric acid, methanesulfonic acid and the like are included. These salts can be formed by the usual methods.

The solvate of the compound according to the present invention may be coordinated with an arbitrary number of solvent molecules (for example, water molecules) to the compound of the present invention or its salt. Examples of the solvate include a hydrate and a alcoholic compound.

In addition, the compound according to the present invention contains the following isomers:

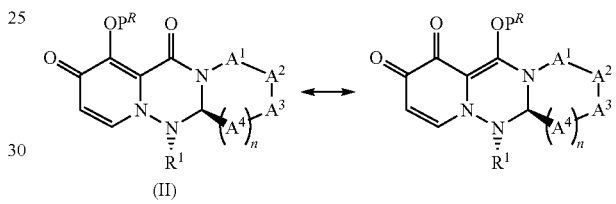

wherein each symbol is same as the above.
$P^R$ is preferably a group converted into OH group by action of drug-metabolizing enzymes, hydrolases, gastric acids, and/or enterobacteria, after in vivo administration (for example, oral administration).

Examples of more preferred embodiment of PR include a group selected from the following formulae a) to ac).

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —(C($P^{R3}$)$_2$)$_p$—$P^{R6}$,
w) —C(=$N^+$($P^{R7}$)$_2$)(—N($P^{R7}$)$_2$),
x) —(C($P^{R3}$)$_2$)$_q$—C(=O)—O—$P^{R2}$,
x') —(C($P^{R3}$)$_2$)$_q$—C(=O)—N(—K)—$P^{R4}$,
x'') —(C($P^{R3}$)$_2$)$_q$—C(=O)—$P^{R1}$, y) —C(P$^{R3}$)$_2$—N(—K)—C(=O)—O—P$^{R2}$,
z) —P(=O)(—P$^{R8}$)(—P$^{R9}$),
aa) —S(=O)$_2$P$^{R10}$,
ab) —P$^{R11}$,
ac) —(C(P$^{R3}$)$_2$)$_r$—O—P$^{R12}$, and
ad) —(C(P$^{R3}$)$_2$)$_t$—N(—K)—P$^{R13}$,
wherein L is straight or branched alkylene, or straight or branched alkenylene;
K is hydrogen, or alkyl optionally substituted by substituent group A;
P$^{R0}$ is alkyl optionally substituted by substituent group A, or alkenyl optionally substituted by substituent group A;
P$^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
P$^{R3}$ is each independently hydrogen or alkyl;
P$^{R4}$ is each independently alkyl optionally substituted by substituent group A, carbocyclyl group optionally substituted by substituent group A, heterocyclyl group optionally substituted by substituent group A, alkyl amino optionally substituted by substituent group A, carbocyclylalkyl optionally substituted by substituent group A, heterocyclylalkyl optionally substituted by substituent group A, or trialkylsilyl;
P$^{R5}$ is each independently hydroxy or OBn;
P$^{R6}$ is carbocyclyl group optionally substituted by substituent group A, or heterocyclyl group optionally substituted by substituent group A;
P$^{R7}$ is each independently alkyl optionally substituted by substituent group A;
P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A;
P$^{R8}$ and P$^{R9}$ may be taken together with an adjacent phosphorus atom to form heterocycle optionally substituted by substituent group A;
P$^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A; and
P$^{R11}$ is alkyl optionally substituted by substituent group A, alkenyl optionally substituted by substituent group A, carbocyclyl group optionally substituted by substituent group A, or heterocyclyl group optionally substituted by substituent group A;
Substituent group A; oxo, alkyl, haloalkyl, hydroxyalkyl, amino, alkylamino, carbocyclyl group, heterocyclyl group, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

Examples of further preferred embodiment of PR include following groups.
a) —C(=O)—P$^{R0}$,
b) —C(=O)—P$^{R1}$,
g) —C(=O)—O—P$^{R2}$,
h) —C(=O)—N(—K)(P$^{R2}$),
i) —C(=O)—O-L-O—P$^{R2}$,
l) —C(P$^{R3}$)$_2$—O—C(=O)—P$^{R4}$,
m) —C(P$^{R3}$)$_2$—O—C(=O)—O—P$^{R4}$,
o) —C(P$^{R3}$)$_2$—O—C(=O)—O-L-O—P$^{R4}$,
v) —(C(P$^{R3}$)$_2$)$_p$—P$^{R6}$,
x) —(C(P$^{R3}$)$_2$)$_q$—C(=O)—O—P$^{R2}$,
y) —C(P$^{R3}$)$_2$—N(—K)—C(=O)—O—P$^{R2}$,
z) —P(=O)(—P$^{R8}$)(—P$^{R9}$),
wherein L is straight or branched alkylene;
K is hydrogen, or alkyl optionally substituted by substituent group A;
P$^{R0}$ is alkyl optionally substituted by substituent group A;
P$^{R1}$ is carbocyclyl group optionally substituted by substituent group A, or heterocyclyl group optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
P$^{R3}$ is each independently hydrogen or alkyl;
P$^{R4}$ is alkyl optionally substituted by substituent group A, carbocyclyl group optionally substituted by substituent group A, or heterocyclyl group optionally substituted by substituent group A;
P$^{R6}$ is carbocyclyl group optionally substituted by substituent group A, or heterocyclyl group optionally substituted by substituent group A;
P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and
P$^{R8}$ and P$^{R9}$ may be taken together with an adjacent phosphorus atom to form heterocycle optionally substituted by substituent group A;
Substituent group A; oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

In particular, a more preferable embodiment of PR is the following group.
m) —C(P$^{R3}$)$_2$—O—C(=O)—O—P$^{R4}$,
wherein P$^{R3}$ is each independently hydrogen or alkyl; and
P$^{R4}$ is alkyl optionally substituted by substituent group A, carbocyclyl group optionally substituted by substituent group A, or heterocyclyl group optionally substituted by substituent group A;
Substituent group A; oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

Examples of another embodiment of a preferable substituent of PR include following groups.

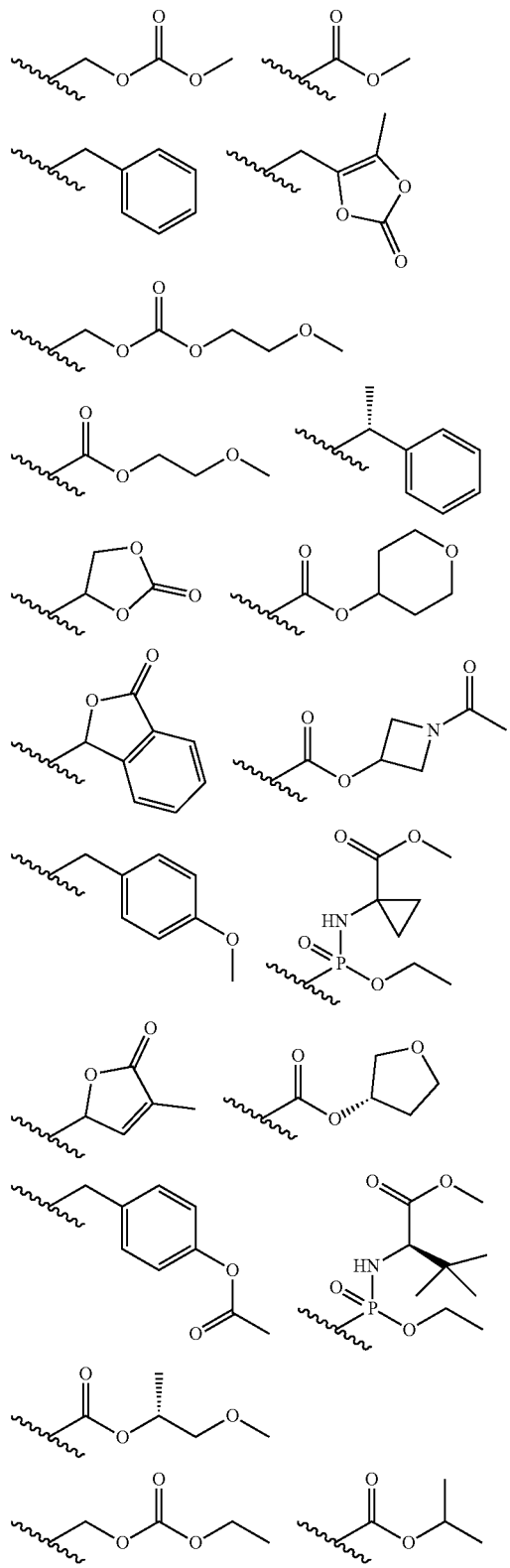

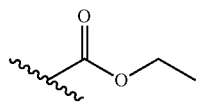

The compound represented by formula (I) used in the present invention (A) can be prepared, for example, by the method described below.

The meaning of each abbreviation is as follows.

Boc: tert-butoxycarbonyl
DBU: diazabicycloundecene
DIAD: diisopropyl azodicarboxylate
DMA: N,N-dimethylacetamide
DMF: N,N-dimethylformamide
HATU: O-(7-azabenzotriazol-1-yl)-N,N,N',N'-tetramethyluronium hexafluorophosphate
NMP: N-methylpyrrolidone
OBn: benzyloxy
THF: tetrahydrofuran
T3P: propyl phosphonic anhydride
WSC.HCl: N-ethyl-M-(3-dimethylaminopropyl)carbodiimide hydrochloride The up and down of the "wedge" and "broken line wedge" indicates the absolute configuration.

(Preparation 1)

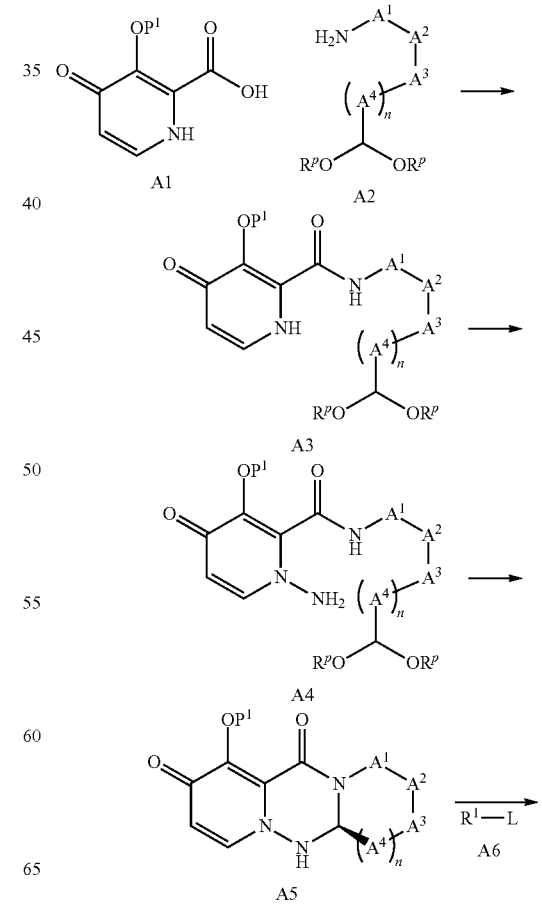

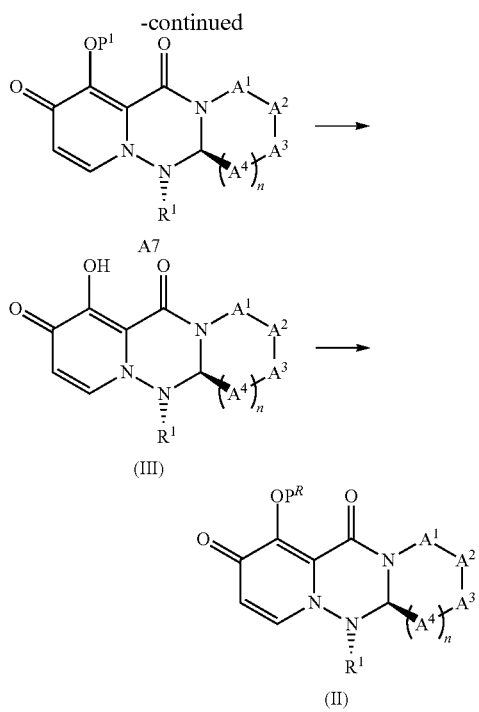

wherein P¹ is hydroxyl protective group; R$^P$ is acetal protective group; L is leaving group; Other each symbol is same as above.

First Step

Compound A3 can be obtained by adding Compound A2 to Compound A1 in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile etc. or in a mixed solvent thereof, and performing a reaction at −20° C. to 60° C., preferably −10° C. to 40° C. for 0.1 hours to 24 hours, preferably 1 hour to 12 hours.

Alternatively, Compound A3 can be obtained by adding an acylating reagent such as diphenylchlorophosphate, thionyl chloride, oxalyl chloride etc. to Compound A1 in the presence or absence of a base such as pyridine, triethylamine, diisopropylethylamine, 1-methylimidazole, etc. in the presence of a solvent such as THF, dioxane, dichloromethane, DMF etc., thereby, generating acid chloride, and adding Compound A2 having a substituent corresponding to an objective compound, and performing a reaction at −20° C. to 60° C., preferably −10° C. to 40° C. for 0.1 hours to 24 hours, preferably 0.5 hours to 12 hours.

Second Step

Compound A4 can be obtained by adding potassium carbonate, sodium carbonate, and O-(2,4-dinitrophenyl)hydroxylamine to Compound A3 in the presence of a solvent such as DMF, DMA, NMP, THF, etc., and performing a reaction at 10° C. to 60° C., preferably 20° C. to 40° C. for 0.1 hours to 48 hours, preferably 1 hour to 24 hours. Third step A deprotecting reaction of an acetal protective group of Compound A4 can be performed by the general method described in Protective Groups in Organic Synthesis, Theodora W Green (John Wiley & Sons) etc. Thereafter, a generated aldehyde group is subjected to an intramolecular reaction, thereby, Compound A5 can be obtained.

For example, racemate of Compound A5 can be obtained by adding acetic acid and/or paratoluenesulfonic acid, metanesulfonic acid etc., to Compound A4 in the presence of a solvent such as DMF, toluene, THF, etc., and performing a reaction at 10° C. to 80° C., preferably 30° C. to 60° C. for 0.5 hours to 12 hours, preferably 1 hour to 6 hours. Compound A5 can be obtained by optical resolution of the racemate of Compound A5 by SFC or HPLC (chiral column).

Fourth Step

Compound A7 can be obtained by adding Compound A6, and a base such as sodium carbonate, potassium carbonate, cesium carbonate, etc. to Compound A5 in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Alternatively, Compound A7 can be obtained by adding Compound A6, and T3P, methane sulfonic acid or paratoluene sulfonic acid to Compound A5 in the presence of a solvent such as DMF, ethyl acetate, butyl acetate, 1,4-dioxane etc. or in a mixed solvent thereof, and performing a reaction at 40° C. to 150° C., preferably 60° C. to 120° C. for 0.1 hours to 48 hours, preferably 1 hour to 24 hours.

Fifth Step

A deprotecting reaction of hydroxyl protective group of Compound A7 can be performed by the general method described in Protective Groups in Organic Synthesis, Theodora W Green (John Wiley & Sons) etc.

Sixth Step

Compound (II) can be obtained by the general method including converting a hydroxyl group of Compound (III) into an ester group or ether group.

For example, the method described in Protective Groups in Organic Synthesis, Theodora W Green (John Wiley & Sons), Prog. Med. 5: 2157-2161 (1985), and Supplied by The British Library—"The world's Knowledge" can be utilized.

(Preparation 2)

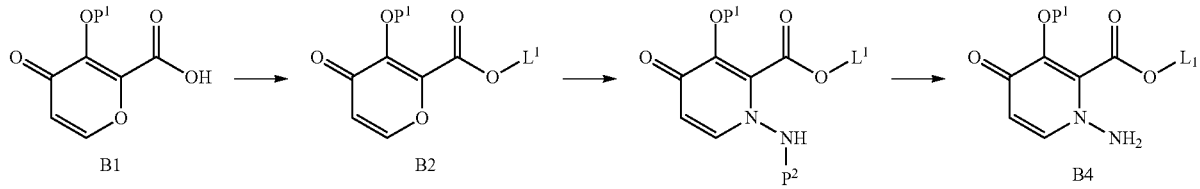

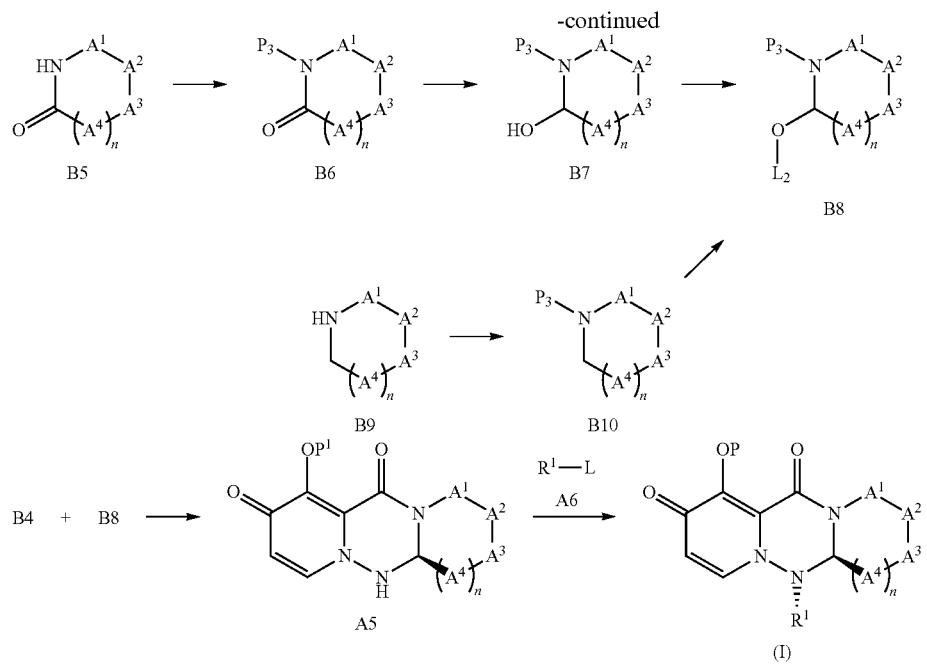

wherein $P^2$ is NH protective group; $L^1$ and $L^2$ is leaving group; Other each symbol is same as above.

First Step

Compound B2 can be obtained by adding Compound A2 and halogenated alkyl such as methyl iodide to Compound B1 in the presence of a base such as diazabicycloundecene in a solvent such as DMF, THF, dichloromethane, acetonitrile, etc. or in a mixed solvent thereof, and performing a reaction at −20° C. to 60° C., preferably −10° C. to 40° C. for 0.1 hours to 24 hours, preferably 1 hour to 24 hours.

Alternatively, Compound B2 can be obtained by adding acylating reagent such as diphenylchlorophosphate, thionyl chloride, oxalyl chloride, etc. to Compound B1 in a solvent such as THF, dioxane, dichloromethane, DMF, etc. or in a mixed solvent thereof, and adding alcohol in the presence of a base such as pyridine, triethylamine, diisopropylethylamine, 1-methylimidazole, etc., and performing a reaction at −20° C. to 60° C., preferably −10° C. to 40° C. for 0.1 hours to 24 hours, preferably 0.5 hours to 12 hours.

Second Step

Compound B3 can be obtained by adding para-toluene sulfonic acid pyridinium and hydrazine protected by Boc etc. to Compound B2 in a solvent such as THF, dioxane, dichloromethane, DMF etc., or in a mixed solvent thereof, and performing a reaction at 10° C. to 150° C., preferably 40° C. to 100° C. for 1 hour to 48 hours, preferably 1 hour to 24 hours.

Third Step

A deprotecting reaction of amino protective group Compound B3 can be performed by the general method described in Protective Groups in Organic Synthesis, Theodora W Green (John Wiley & Sons) etc.

Fourth Step

Compound B6 can be obtained by adding a base such as n-butyl lithium, etc. to Compound B5 in a solvent such as THF, dioxane, dichloromethane, DMF etc., or in a mixed solvent thereof, and then adding haloformic acid alkyl and performing a reaction for 0.1 hours to 48 hours, preferably 1 hour to 24 hours.

Fifth Step

Compound B7 can be obtained by adding reducing agent such as Lithium diisobutylaluminum hydride, etc. to Compound B6 in a solvent such as THF, dioxane, dichloromethane, DMF etc., or in a mixed solvent thereof, and performing a reaction for 0.1 hours to 48 hours, preferably 1 hour to 24 hours.

Sixth Step

Compound B8 can be obtained by adding para-toluene sulfonic acid or methane sulfonic acid to Compound B7 in alcohol, and performing a reaction at 0° C. to 100° C. for 0.1 hours to 48 hours, preferably 1 hour to 24 hours.

Seventh Step

Compound B10 can be obtained by adding haloformic acid alkyl to Compound B9 in the presence or absence of a base such as pyridine, triethylamine, diisopropylethylamine, 1-methylimidazole, etc., in a solvent such as THF, dioxane, dichloromethane, DMF etc., or in a mixed solvent thereof, and performing a reaction at −40° C. to 40° C. for 0.1 hours to 48 hours, preferably 1 hour to 24 hours.

Eighth Step

Compound B8 can be obtained by immersing carbon electrode (anode) and platinum electrode (cathode) to Compound B10 in a solvent such as alcohol in the presence of a base such as potassium carbonate and tetraethylaminium perchlorate, and flushing with a constant current of 0.1~1.0 A with stirring for 0.1 hours to 48 hours, preferably 1 hour to 24 hours.

Ninth to Tenth Step

Compound (I) can be obtained from Compound B4 and B8 in the same manner as in the third to sixth steps in preparation 1.

The present invention is a medicament, characterized in that (A) a compound represented by the formula (I):

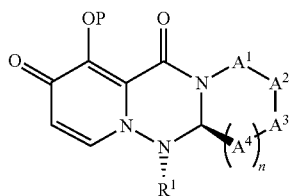

(I)

wherein P is hydrogen or a group to form a prodrug, its pharmaceutically acceptable salt or a solvate thereof, is combined with (B) compound(s) having an anti-influenza activity, its pharmaceutically acceptable salt or a solvate thereof, and/or an antibody having an anti-influenza activity.

The term "medicament characterized by combination" includes an embodiment in which each compound is used as a compounding agent, an embodiment in which each compound is used as a kit, an embodiment in which it is administered simultaneously, an embodiment in which it is administered at intervals and an embodiment in which they are used in combination with other drugs.

The compound represented by the formula (I), its pharmaceutically acceptable salt or a solvate thereof can be used in combination with a compound having an anti-influenza activity, its pharmaceutically acceptable salt or a solvate thereof, and/or an antibody having an anti-influenza activity, and it can enhance anti-influenza effect of a compound having an anti-influenza activity, its pharmaceutically acceptable salt or a solvate thereof, and/or an antibody having an anti-influenza.

Also, a compound having an anti-influenza activity, its pharmaceutically acceptable salt or a solvate thereof, and/or an antibody having an anti-influenza activity can be used in combination with the compound represented by the formula (I), its pharmaceutically acceptable salt or a solvate thereof, and it can enhance anti-influenza effect of the compound represented by the formula (I), its pharmaceutically acceptable salt or a solvate thereof.

Also, it is found in the present invention that a combination of (B-1) a compound having a neuraminidase inhibitory activity, its pharmaceutically acceptable salt or a solvate thereof, or (B-2) a compound having a PB 2 Cap binding inhibitory activity, its pharmaceutically acceptable salt or a solvate thereof and (A) a compound having a cap-dependent endonuclease inhibitory activity, its pharmaceutically acceptable salt or a solvate thereof is particularly desirable, among the combination of (A) a compound having a cap-dependent endonuclease inhibitory activity, its pharmaceutically acceptable salt or a solvate thereof, and "a compound having an anti-influenza activity, its pharmaceutically acceptable salt or a solvate thereof and/or an antibody having an anti-influenza activity" described in (7).

The present invention includes the following invention: A medicament, characterized in that (A) a compound having a cap-dependent endonuclease inhibitory activity, its pharmaceutically acceptable salt or a solvate thereof, is combined with (B-1) a compound having a neuraminidase inhibitory activity, its pharmaceutically acceptable salt or a solvate thereof, or (B-2) a compound having a PB 2 Cap binding inhibitory activity, its pharmaceutically acceptable salt or a solvate thereof.

(A) A compound having a cap-dependent endonuclease inhibitory activity, its pharmaceutically acceptable salt or a solvate thereof can be used in combination with "a compound having an anti-influenza activity, its pharmaceutically acceptable salt or a solvate thereof and/or an antibody having an anti-influenza activity" described in (7), preferably (B-1) a compound having a neuraminidase inhibitory activity, its pharmaceutically acceptable salt or a solvate thereof, or (B-2) a compound having PB2 Cap binding inhibitory activity, its pharmaceutically acceptable salt or a solvate thereof, and it can enhance anti-influenza effect of "a compound having an anti-influenza activity, its pharmaceutically acceptable salt or a solvate thereof, and/or an antibody having an anti-influenza activity" described in (7).

Also, "a compound having an anti-influenza activity, its pharmaceutically acceptable salt or a solvate thereof and/or an antibody having an anti-influenza activity" described in (7), preferably (B-1) a compound having a neuraminidase inhibitory activity, its pharmaceutically acceptable salt or a solvate thereof, or (B-2) a compound having PB2 Cap binding inhibitory activity, its pharmaceutically acceptable salt or a solvate thereof can be used in combination with a compound having a cap-dependent endonuclease inhibitory activity, its pharmaceutically acceptable salt or a solvate thereof, and it can enhance anti-influenza effect of a compound having a cap-dependent endonuclease inhibitory activity, its pharmaceutically acceptable salt or a solvate thereof.

The route of administration of the medicament of the present invention can be administered by either oral or parenteral methods and is not particularly limited to them.

In the case of oral administration, it can be administered by the usual manner in the form of solid preparations for internal use (e.g., tablets, powders, granules, capsules, pills, films), internal solutions (e.g., suspensions, emulsions, elixirs, syrups, limonade agents, alcoholic agents, fragrance solutions, extracts, decoctions, tinctures), and the like. The tablet may be sugar-coated tablets, film-coated tablets, enteric coated tablets, extended release tablets, troches, sublingual tablets, buccal tablets, chewable tablets or orally disintegrating tablets. The powders and granules may be dry syrups. The capsule may be soft capsule, microcapsules or sustained release capsules.

In the case of parenteral administration, any forms of injections, drops, external preparations (e.g., eye drops, nasal drops, ear drops, aerosols, inhalants, lotions, infusions, coating agents, gargles, enemas, ointments, plasters, jellies, creams, patches, cataplasms, external powders, suppositories) which are usually used can be suitably administered. The injection may be emulsions such as O/W, W/O, O/W/O or W/O/W type.

The effective amount of the compound used in the medicament of the present invention are mixed as necessary with various pharmaceutical additives such as excipients, binders, disintegrants, and/or lubricants suitable for the dosage form to give the pharmaceutical composition. Furthermore, the pharmaceutical composition can be used for children, the elderly, serious patients or surgery, by appropriately changing the effective amount of the compound used in the medicament of the present invention, the dosage form and/or various pharmaceutical additives. The pediatric pharmaceutical composition is preferably administered to patients aged under 12 years old or 15 years old. The pediatric pharmaceutical composition can also be administered to patients less than 27 days after birth, 28 days to 23 months after birth, 2 years old to 11 years old, 12 years old to 16 or 18 years old. The pharmaceutical composition for the elderly is preferably administered to patients over 65 years old.

The dose of the medicament of the present invention can be appropriately selected on the basis of the clinically used dosage. The mixing ratio of (A) the compound represented by the formula (I) and (B) the combination drug can be appropriately selected depending on the administration subject, administration route, target disease, symptom, combination, and the like. For example, when the subject to be administered is a human, 0.01 to 400 parts by weight of (B) the combination drug may be used per 1 part by weight of (A) the compound represented by the formula (I).

The medicament of the present invention is useful for symptoms and/or diseases induced by influenza virus. It is effective for the treatment, prevention and/or improvement of symptoms such as cold-like symptoms accompanied by fever, chills, headache, muscle pain, and/or general malaise, airway inflammation symptoms such as sore throat, nasal discharge, nasal congestion, cough, and/or sputum, gastrointestinal symptoms such as abdominal pain, vomiting, and/or diarrhea, and secondary infection such as acute encephalopathy and/or pneumonia.

The present invention is explained in more detail below by Examples, but the present invention is not limited to them.

Synthesis examples of compounds represented by formula (I) in (A) and synthesis examples of intermediates are listed below.

The NMR analysis obtained compounds was carried out in 300 MHz, and was measured using DMSO-$d_6$, CDCl$_3$.

The term RT represents a retention time at LC/MS: liquid chromatography/mass spectrometry, and was measured under the following conditions.
(Measurement Conditions)
(1) Column: ACQUITY UPLC (Registered trademark) BEH C18 (1.7 μm i.d.2.1×50 mm) (Waters)
  Flow rate: 0.8 mL/min
  UV detection wavelength: 254 nm
  Mobile phase: [A]: a 0.1% formic acid-containing aqueous solution, [B]: a 0.1% formic acid-containing acetonitrile solution
  Gradient: a linear gradient of 5% to 100% solvent [B] was carried out in 3.5 minutes, and 100% solvent [B] was kept for 0.5 minutes.
(2) Column: Shim-pack XR-ODS (2.2 μm, i.d.50×3.0 mm) (Shimadzu)
  Flow rate: 1.6 mL/min
  UV detection wavelength: 254 nm
  Mobile phase: [A]: a 0.1% formic acid-containing aqueous solution, [B]: a 0.1% formic acid-containing acetonitrile solution
  Gradient: a linear gradient of 10% to 100% solvent [B] was carried out in 3 minutes, and 100% solvent [B] was kept for 0.5 minutes.
(3) Column: ACQUITY UPLC (Registered trademark) BEH C18 (1.7 μm i.d.2.1×50 mm) (Waters)
  Flow rate: 0.8 mL/min
  UV detection wavelength: 254 nm
  Mobile phase: [A]: a 10 mM ammonium carbonate-containing aqueous solution, [B]: a acetonitrile solution
  Gradient: a linear gradient of 5% to 100% solvent [B] was carried out in 3.5 minutes, and 100% solvent [B] was kept for 0.5 minutes.

Reference Example 1

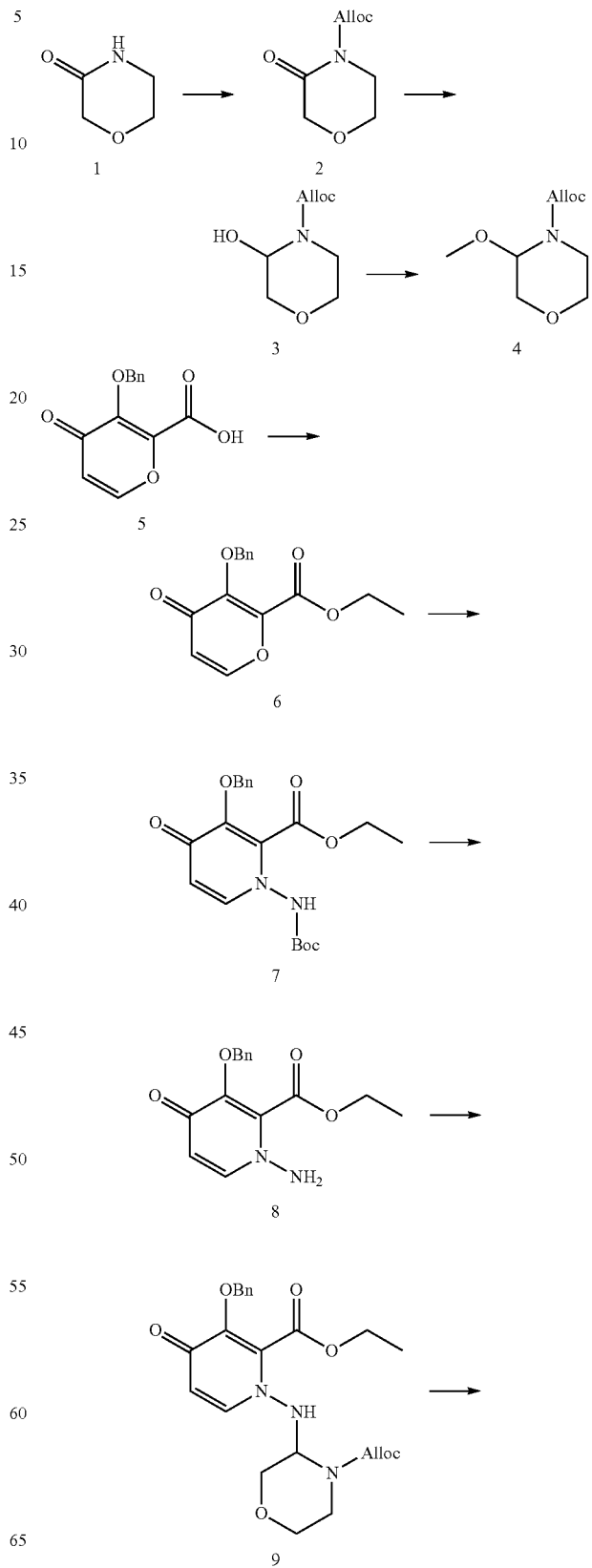

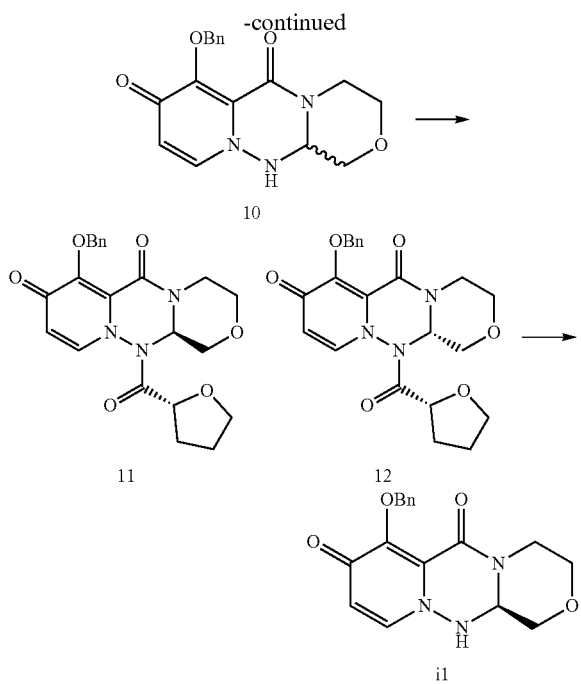

First Step

To a solution of Compound 1 (5.0 g, 49.5 mmol) in THF (100 mL) was added dropwise 1.62 mol/L n-butyllithium in hexane (30.5 mL, 49.5 mmol) at −78° C. under a nitrogen atmosphere, and the mixture was stirred at −78° C. for 2 hours. A solution of chloroformate allyl (5.96 g, 49.5 mmol) in THF (20 mL) was added dropwise thereto, and the mixture was stirred at −78° C. for 2 hours. The mixture was quenched with a saturated aqueous solution of ammonium chloride, warmed up to room temperature, and extracted with ethyl acetate. The obtained organic layer was washed with brine, dried over anhydrous magnesium sulfate, and concentrated under reduced pressure to obtain Compound 2 (5.66 g, 62%).

1H-NMR (CDCl3) δ:3.83 (t, J=8.0 Hz, 2H), 3.92 (t, J=8.0 Hz, 2H), 4.26 (s, 2H), 4.78 (d, J=8.0 Hz, 2H), 5.30 (d, J=12.0 Hz, 1H), 5.44 (d, J=16.0 Hz, 1H), 5.93-6.03 (m, 1H),

Second Step

To a solution of Compound 2 (6.6 g, 35.6 mmol) in THF (66 mL) was added dropwise 1.03 mol/L DIBAL-H in hexane (45.0 mL, 46.3 mmol), and the mixture was stirred at −78° C. for 1 hour. The mixture was quenched with acetone, an aqueous solution of Rochelle salt was added thereto. The mixture was stirred, and extracted with ethyl acetate. The obtained organic layer was washed with brine, dried over anhydrous magnesium sulfate, and concentrated under reduced pressure to obtain Compound 3 (6.21 g, 93%).

1H-NMR (CDCl3) δ:3.44 (br, 1H), 3.50-3.64 (m, 2H), 3.71 (br, 1H), 3.95 (d, J=8.0 Hz, 2H), 4.64 (d, J=8.0 Hz, 2H), 5.24 (d, J=12.0 Hz, 1H), 5.40 (d, J=16.0 Hz, 1H), 5.47 (d, J=4 Hz, 1H), 5.87-6.00 (m, 1H)

Third Step

To a solution of Compound 3 (6.2 g, 33.1 mmol) in methanol (65 mL) was added p-Toluenesulfonic acid monohydrate (0.63 g, 3.31 mmol), and the mixture was stirred at room temperature over night. The mixture was quenched with an aqueous solution of sodium hydrogen carbonate, concentrated, and extracted with ethyl acetate. The obtained organic layer was washed with brine, dried over anhydrous magnesium sulfate, and concentrated under reduced pressure to obtain Compound 4 (5.77 g, 87%).

1H-NMR (CDCl3) δ:3.34 (s, 3H), 3.55 (br, 2H), 3.73-3.99 (m, 3H), 4.64 (d, J=8.0 Hz, 2H), 5.10-5.20 (m, 1H), 5.25 (d, J=8.0 Hz, 1H), 5.33 (d, J=16 Hz, 1H), 5.88-6.05 (m, 1H)

Fourth Step

To a solution of Compound 5 (20.0 g, 81 mmol) in DMF (100 mL) were added ethyl iodide (22.8 g, 146 mmol) and diazabicycloundecene (18.4 mL, 122 mmol), and the mixture was stirred at room temperature over night. The mixture was poured into 10% aqueous solution of ammonium chloride, and extracted with ethyl acetate. The obtained organic layer was washed with brine, dried over anhydrous magnesium sulfate, and concentrated under reduced pressure to obtain Compound 6 (22.3 g, 100%).

1H-NMR (CDCl3) δ:1.23 (t, J=8.0 Hz, 3H), 4.28 (q, J=8.0 Hz, 2H), 5.16 (s, 2H), 6.57 (d, J=4.0 Hz, 1H), 7.28-7.48 (m, 5H), 8.21 (d, J=4.0 Hz, 1H).

Fifth Step

To a solution of Compound 6 (500 mg, 1.82 mmol) in DMA (5.0 mL) were added pyridinium p-toluenesulfonate (1.37 g, 5.47 mmol) and Boc-hydrazine (361 mg, 2.74 mmol), and the mixture was stirred at 60° C. for 14 hours. To the mixture was added water and the mixture was extracted with ethyl acetate. The obtained organic layer was washed with a saturated aqueous solution of ammonium chloride and brine, dried over anhydrous magnesium sulfate, and concentrated under reduced pressure. The obtained residue was purified by silica gel column chromatography (chloroform-methanol) to obtain Compound 7 (519 mg, 73%).

1H-NMR (CDCl3) δ:1.24 (t, J=8.0 Hz, 3H), 1.46 (s, 9H), 4.26 (q, J=8.0 Hz, 2H), 5.28 (s, 2H), 6.40 (d, J=8.0 Hz, 1H), 7.27-7.38 (m, 4H), 7.40-7.45 (m, 2H).

Sixth Step

Compound 7 (500 mg, 1.29 mmol) was dissolved in 4 mol/L hydrogen chloride in ethyl acetate (5 mL), and the mixture was stirred at room temperature for 1 hour. The mixture was concentrated under reduced pressure. To the obtained residue was added a saturated aqueous solution of sodium hydrogen carbonate, and the mixture was extracted with dichloromethane. The obtained organic layer was washed with brine, dried over anhydrous magnesium sulfate, and concentrated under reduced pressure to obtain Compound 8 (369 mg, 99%).

1H-NMR (CDCl3) δ:1.26 (t, J=8.0 Hz, 3H), 4.31 (q, J=8.0 Hz, 2H), 5.24 (s, 2H), 6.47 (d, J=8.0, 1H), 7.28-7.44 (m, 5H), 7.64 (d, J=8.0, 1H).

Seventh Step

To a solution of Compound 8 (365 mg, 1.27 mmol) and Compound 4 (306 mg, 1.52 mmol) in acetonitrile (8 mL) was added dropwise tin chloride (0.223 mL, 1.90 mmol) at −25° C. under a nitrogen atmosphere, and the mixture was stirred at −25° C. for 45 minutes. The mixture was quenched with a saturated aqueous solution of sodium hydrogen carbonate, and dichloromethane was added thereto. The mixture was stirred at room temperature and filtered through Celite, and filtrate was extracted with dichloromethane. The obtained organic layer was washed with brine, dried over anhydrous magnesium sulfate, and concentrated under reduced pressure to obtain crude Compound 9. The obtained Compound 9 was dissolved in THF (8 mL), morpholine (1.10 mL, 12.7 mmol) and tetrakis(triphenylphosphine)palladium (146 mg, 0.127 mmol) were added thereto, and the mixture was stirred at room temperature for 2 hours. To the mixture was added diethyl ether (16 mL), and the precipitated solid was filtered and dried to obtain Compound 10 (418 mg, 100%).

1H-NMR(CDCl3) δ:2.90-2.99 (m, 1H), 3.13 (t, J=12.0 Hz, 1H), 3.40-3.46 (m, 1H), 4.00-4.08 (m, 1H), 4.14 (d, J=12.0 Hz, 1H), 5.07 (s, 2H), 6.22 (d, J=8.0 Hz, 1H), 7.29-7.40 (m, 3H), 7.56 (d, J=8.0 Hz, 2H), 7.71 (d, J=8.0 Hz, 1H)

Eighth Step

To a suspension of (R)-2-Tetrahydrofurioic Acid (855 mg, 7.36 mmol) and Compound 10 (2.00 g, 6.11 mmol) in ethyl acetate (9 ml) were added pyridine (4.00 ml, 49.6 mmol) and T3P (50% in ethyl acetate, 11.0 ml, 18.5 mmol) at room temperature, and the mixture was stirred over night. The precipitated solid was filtered and washed with ethyl acetate (4 ml) and ethanol (4 ml). The obtained solid was suspended in ethanol (6 ml) and the suspension was stirred at room temperature for 6.5 hours. The suspension was filtered and the obtained solid was washed with ethanol (2 ml) twice to obtain Compound 11 (1.18 g, 45.4%).

¹H-NMR (DMSO) δ:1.80-1.94 (m, 2H), 1.95-2.14 (m, 2H), 3.21-3.35-(m, 2H), 3.50-3.60 (m, 1H), 3.70-3.82 (m, 3H), 4.00-4.05 (m, 1H), 4.32-4.38 (m, 1H), 5.14 (dd, J=10.8 Hz, 21.6 Hz, 2H), 5.76-5.81 (m, 1H), 6.29 (d; J=4.8 Hz, 1H), 7.28-7.39 (m, 3H), 7.48-7.54 (m, 2H), 7.64-7.75 (m, 1H)

Ninth Step

To a suspension of Compound 11 (500 mg, 1.18 mmol) in ethanol (3.5 ml) was added DBU (0.0035 ml, 0.023 mmol) at room temperature, and the mixture was stirred for 30 minutes. To the obtained suspension was added diisopropylether (6.5 ml), and the mixture was stirred at room temperature for 30 minutes. The precipitated solid was filtered and washed with ethyl acetate (1.5 ml) twice to obtain Compound i1 (346 mg, 89.9%).

¹H-NMR (DMSO) δ:2.80-3.00 (m, 1H), 3.10-3.18 (m, 1H), 3.38-3.50 (m, 1H), 3.98-4.08 (m, 2H), 4.10-4.20 (m, 1H), 4.76-4.84 (m, 1H), 5.04-5.14 (m, 2H), 6.22 (m, J=7.6 Hz, 1H), 7.27-7.40 (m, 4H), 7.56-7.60 (m, 2H), 7.70 (d, J=7.6 Hz, 1H)

Reference Example 2

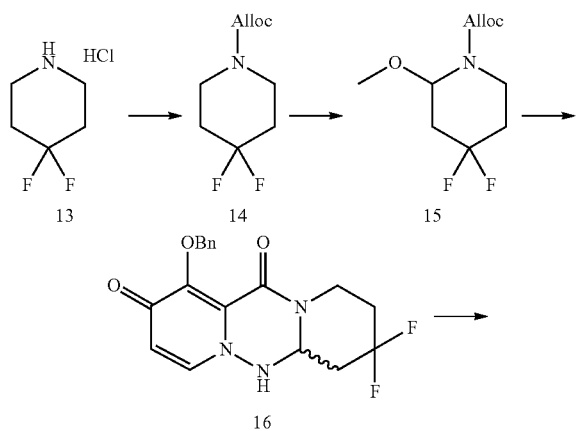

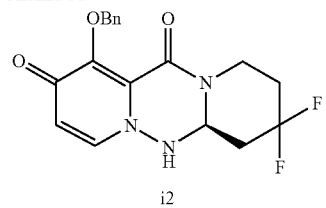

First Step

To a suspension of Compound 13 (8.0 g, 50.8 mmol) in dichloromethane (120 mL) was added triethylamine (17.6 mL, 127 mmol) under ice-water bath, and allyl chloroformate (6.44 mL, 60.9 mmol) was added dropwise thereto, and the mixture was stirred at 0° C. for 1 hour. To the mixture was added water, and the mixture was extracted with dichloromethane. The obtained organic layer was washed with 5% aqueous solution of citric acid and a saturated aqueous solution of sodium hydrogen carbonate, dried over anhydrous magnesium sulfate, and concentrated under reduced pressure to obtain Compound 14 (10.1 g, 97%).

1H-NMR (CDCl3) δ:1.96 (br, 4H), 3.62 (s, 4H), 4.60 (s, 2H), 5.22 (d, J=12.0 Hz, 1H), 5.30 (d, J=16.0 Hz, 1H), 5.86-5.99 (m, 1H)

Second Step

To a solution of Compound 14 (0.9 g, 4.39 mmol), potassium carbonate (60 mg, 0.44 mmol) and tetraethylammonium perchlorate (50 mg, 0.22 mmol) in methanol (30 mL) were immersed carbon electrode (anode) and platinum electrode (cathode), and the mixture was flushed with a constant current of 0.1A with stirring at room temperature for 6 hours. To the mixture were added ethyl acetate and water, and the mixture was extracted with ethyl acetate. The obtained organic layer was dried over anhydrous magnesium sulfate, and concentrated under reduced pressure to obtain Compound 15 (992 mg, 96%).

1H-NMR (CDCl3) δ:1.81-2.15 (m, 3H), 2.39 (t, J=12.0 Hz, 1H), 3.27 (s, 3H), 3.61 (s, 1H), 4.11 (br, 1H), 4.61 (br, 2H), 5.20-5.36 (m, 2H), 5.57 (br, 1H), 5.88-5.99 (m, 1H)

Third Step

Compound 16 was obtained in the same manner as in the seventh and eighth steps in reference example 1.

Fourth Step

The optical resolution of Compound 16 (870 mg, 2.41 mmol) by Waters SFC30 System (Daicel CHIRALPAK IB, liquefied carbon dioxide-methanol) gave Compound i2 (270 mg, 31%).

Analysis Condition

<Waters SFC30 System>

Column: CHIRALPAK IB/SFC (5 μm, i.d.250×4.6 mm) (DAICEL)

Flow rate: 8.0 mL/min; UV detection wavelength: 254 nm

Back pressure: 100 bar

Mobile phase: [A]: liquefied carbon dioxide, [B]: methanol

Gradient: 5% solvent [B] was kept for 1 minute, a linear gradient of 5% to 40% solvent [B] was carried out in 6 minutes, 40% solvent [B] was kept for 2 minutes, and 5% solvent [B] was kept for 1 minute.

Elution time: 7.3 minutes

Reference Example 3

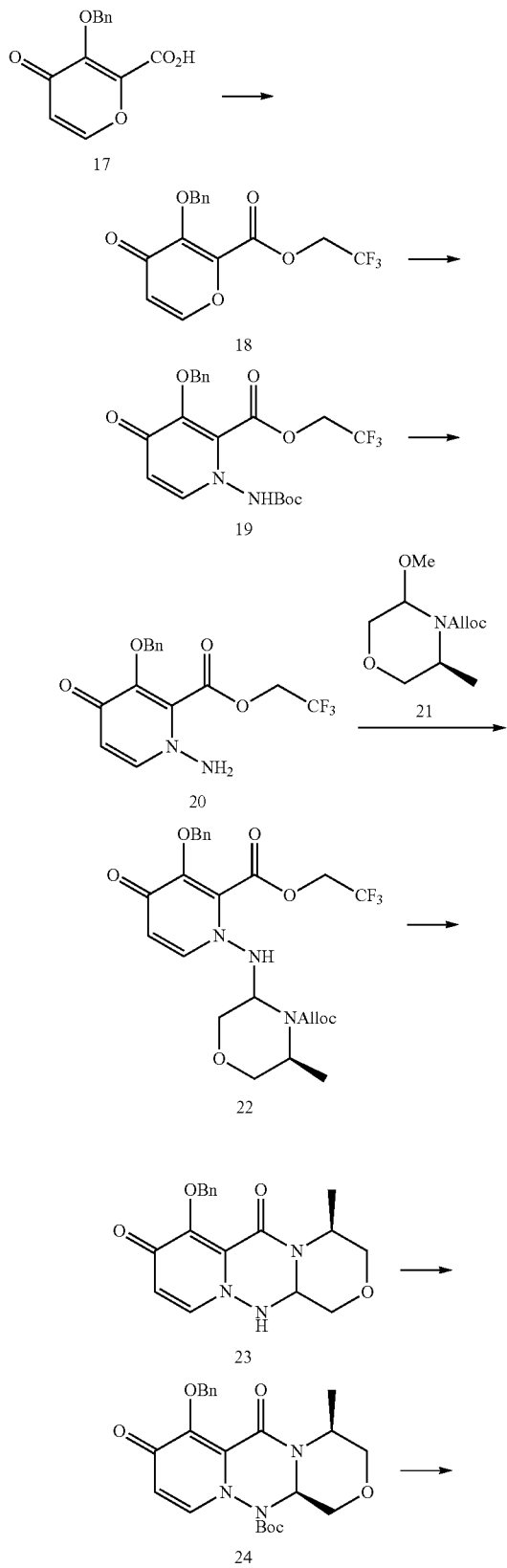

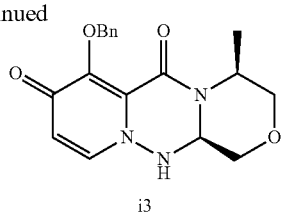

First Step

To a solution of Compound 17 (4.00 g, 16.3 mmol) in dichloromethane (40 mL) were added oxalyl dichloride (1.56 mL, 17.9 mmol) and DMF (0.013 mL, 0.162 mmol) under iced-bath, and the mixture was warmed up to room temperature and stirred for 5 hours. The mixture was concentrated under reduced pressure, and the obtained residue was dissolved in dichloromethane (40 mL), 2,2,2-trifluoroethanol (2.44 g, 24.4 mmol), triethylamine (4.50 mL, 32.5 mmol) and 4-(dimethylamino)pyridine (99.0 mg, 0.812 mmol) were added thereto under iced-bath, and the mixture was warmed up to room temperature and stirred for 1 hour. The mixture was concentrated under reduced pressure and to the obtained residue was added 1 mol/L aqueous solution of hydrochloric acid, and the mixture was extracted with ethyl acetate. The obtained organic layer was washed with 1 mol/L aqueous solution of hydrochloric acid and brine, dried over anhydrous magnesium sulfate to obtain Compound 18 (5.33 g, 100%). 1H-NMR (CDCl3) δ:4.64 (q, J=8.2 Hz, 2H), 5.38 (s, 2H), 6.49 (d, J=5.6 Hz, 1H), 7.30-7.38 (m, 3H), 7.43-7.49 (m, 2H), 7.75 (d, J=5.6 Hz, 1H).

Second and Third Steps

Compound 20 was obtained in the same manner as in the fifth and sixth steps in reference example 1.

1H-NMR (CDCl3) δ:4.55 (q, J=8.3 Hz, 2H), 5.18 (s, 2H), 5.29 (s, 2H), 6.37 (d, J=7.8 Hz, 1H), 7.30-7.42 (m, 6H).

Fourth and Fifth Steps

Compound 23 was obtained in the same manner as in the seventh step in reference example 1.

LC/MS (ESI):m/z=342.1 [M+H]+, RT=1.00, 1.09 min, method (1)

Sixth Step

To a solution of Compound 23 (820 mg, 2.40 mmol) in dichloromethane (16.5 mL) were added Boc2O (0.837 mL, 3.60 mmol), triethylamine (0.499 mL, 3.60 mmol) and 4-(dimethylamino)pyridine (44.0 mg, 0.360 mmol), and the mixture was stirred at room temperature for 3.5 hours. To the mixture was added 1 mol/L aqueous solution of hydrochloric acid and the mixture was extracted with ethyl acetate. The obtained organic layer was washed with 1 mol/L aqueous solution of hydrochloric acid and brine, dried over anhydrous sodium sulfate, and concentrated under reduced pressure. The obtained residue was purified by silica gel column chromatography (chloroform-methanol) to obtain Compound 24 (593 mg, 56%) and Compound i3 (170 mg, 16%). Compound 24:LC/MS (ESI):m/z=441.9 [M+H]+, RT=1.67 min, method (1)

Seventh Step: Method for Producing Compound i3

Compound 24 (547 mg, 1.24 mmol) was dissolved in acetic acid (5.5 mL) and the mixture was stirred at 80° C. for 5 hours. The mixture was concentrated under reduced pressure and the obtained residue was purified by silica gel column chromatography (chloroform-methanol) to obtain Compound i3 (454 mg, 100%).

1H-NMR (CDCl3) δ:1.46 (d, J=6.4 Hz, 3H), 3.45 (dd, J=10.5, 10.5 Hz, 1H), 3.55 (dd, J=11.7, 4.3 Hz, 1H), 3.92 (dd, J=11.7, 3.6 Hz, 1H), 3.95-4.01 (m, 2H), 4.76 (dq,

J=13.9, 4.3 Hz, 1H), 5.19 (d, J=10.2 Hz, 1H), 5.22 (d, J=10.2 Hz, 1H), 5.36 (d, J=12.9 Hz, 1H), 6.28 (d, J=7.8 Hz, 1H), 7.25 (d, J=7.8 Hz, 1H), 7.28-7.36 (m, 3H), 7.56-7.61 (m, 2H).

Example 1

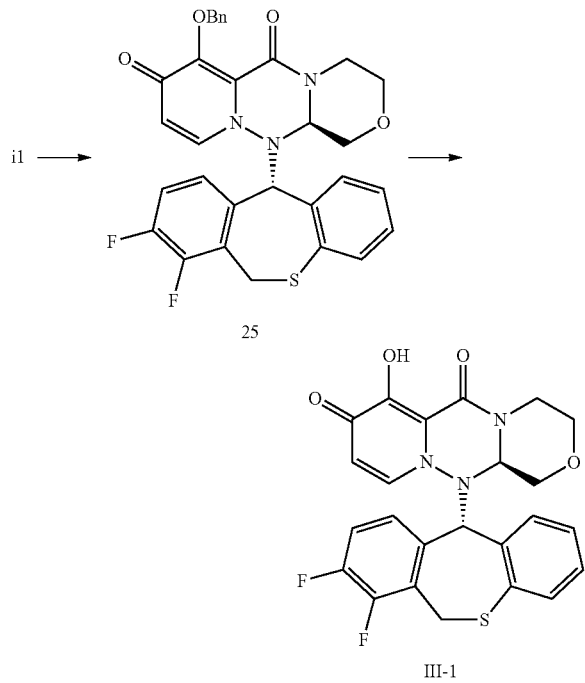

First Step

Compound i1 (1100 g, 3360 mmol) and 7,8-difluoro-6,11-dihydrodibenzothiepine-11-ol (977 g, 3697 mmol) were suspended in 50 wt % T3P in ethyl acetate (3208 g, 5041 mmol) and ethyl acetate (1.1 L). To the mixture was added methanesulfonic acid (436 ml, 6721 mmol) at room temperature and the mixture was stirred at 70° C. for 5.5 hours. To the mixture was added water under ice-water bath and the mixture was stirred at room temperature for 1 hour. THF was added thereto and the mixture was extracted with ethyl acetate. The obtained organic layer was washed with water and 8% aqueous solution of sodium hydrogen carbonate, dried over anhydrous sodium sulfate, and concentrated under reduced pressure. The obtained residue was dissolved in THF (5.5 L) and potassium carbonate (790 g, 5713 mmol) was added thereto. The mixture was warmed up to 50° C., benzyl bromide (240 ml, 2016 mmol) was added dropwise thereto, and the mixture was stirred at 60° C. for 8.5 hours. To the mixture was added dropwise 2 mol/L aqueous solution of hydrochloric acid under ice-water bath, and the mixture was stirred at room temperature for 10 minutes and extracted with ethyl acetate. The obtained organic layer was washed with water and 8% aqueous solution of sodium hydrogen carbonate and dried over anhydrous magnesium sulfate. An activated carbon (Norit SX-2, 240 g) was added thereto, the mixture was filtered through Celite, and the filtrate was concentrated under reduced pressure. To the obtained residue was added ethyl acetate and hexane and the precipitated solid was filtered to obtain Compound 25 (1019 g, 1776 mmol, 53%).

$^1$H-NMR (CDCl$_3$) δ:2.88 (1H, t, J=11.2 Hz), 3.28-3.39 (2H, m), 3.72 (1H, d, J=12.6 Hz), 3.86 (1H, d, J=9.6 Hz), 4.03 (1H, d, J=13.9 Hz), 4.45 (1H, d, J=8.6 Hz), 4.67 (1H, d, J=13.1 Hz), 5.19-5.26 (2H, m), 5.45 (1H, d, J=10.9 Hz), 5.63 (1H, d, J=10.9 Hz), 5.77 (1H, d, J=7.6 Hz), 6.40 (1H, d, J=7.8 Hz), 6.68 (1H, t, J=6.9 Hz), 6.94-7.01 (2H, m), 7.03-7.12 (3H, m), 7.29-7.38 (3H, m), 7.61 (2H, d, J=7.1 Hz).

Second Step

To a solution of Compound 25 (1200 g, 2092 mmol) in DMA (3.6 L) was added lithium chloride (443 g, 10.5 mol) at room temperature, and the mixture was stirred at 80° C. for 3 hours. To the mixture were added acetone (1.2 L), 0.5 mol/L aqueous solution of hydrochloric acid (6.0 L) and water (2.4 L) under ice-water bath, and the mixture was stirred for 1 hour. The precipitated solid was filtered. The obtained solid was dissolved in chloroform, isopropyl ether was added thereto, and the precipitated solid was filtered to obtain Compound III-1 (950 g, 1965 mmol, 94%).

$^1$H-NMR (CDCl$_3$) δ:2.99 (1H, dt, J=17.5, 6.8 Hz), 3.47 (1H, td, J=11.9, 2.5 Hz), 3.60 (1H, t, J=10.6 Hz), 3.81 (1H, dd, J=11.9, 3.3 Hz), 3.96 (1H, dd, J=11.0, 2.9 Hz), 4.07 (1H, d, J=13.8 Hz), 4.58 (1H, dd, J=10.0, 2.9 Hz), 4.67 (1H, dd, J=13.5, 1.9 Hz), 5.26-5.30 (2H, m), 5.75 (1H, d, J=7.8 Hz), 6.69 (1H, d, J=7.7 Hz), 6.83-6.87 (1H, m), 6.99-7.04 (2H, m), 7.07-7.15 (3H, m).

The following example compounds were synthesized from commercially available compounds or intermediates described in reference example according to the above examples.

TABLE 1

| No. | Structure | H-NMR or LC/MS |
|---|---|---|
| III-2 | (structure image) | 1H-NMR (CDCl3) δ: 2.99 (t, J = 12.4 Hz, 1H), 3.43-3.61 (m, 3H), 3.81 (d, J = 12.0 Hz, 1H), 3.96 (d, J = 11.0 Hz, 1H), 4.59 (d, J = 9.8 Hz, 1H), 4.66 (d, J = 13.2 Hz, 1H), 5.26 (s, 1H), 5.54 (d, J = 13.4 Hz, 1H), 5.75 (d, J = 8.2 Hz, 1H), 6.69 (d, J = 7.7 Hz, 1H), 6.84 (t, J = 7.0 Hz, 1H), 6.98-7.05 (m, 2H), 7.07-7.12 (m, 3H), 7.22 (t, J = 7.0 Hz, 1H). |

TABLE 1-continued

| No. | Structure | H-NMR or LC/MS |
|---|---|---|
| III-3 | 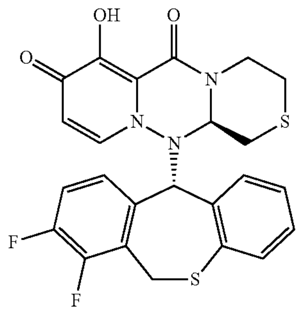 [SMILES: O=C1c2c(O)c(=O)ccn2N([C@@H]2c3ccccc3SCc3c2ccc(F)c3F)[C@@H]2CSCCN12] | 1H-NMR(CDCl3)δ: 2.37 (d, J = 13.2 Hz, 1H), 2.57 (d, J = 12.4 Hz, 1H), 2.79-2.87 (m, 1H), 2.90-3.03 (m, 2H), 4.08 (d, J = 13.6 Hz, 1H), 4.64 (d, J = 10.8 Hz, 1H), 5.05 (d, J = 12.0 Hz, 1H), 5.19 (s, 1H), 5.25-5.32 (m, 1H), 5.78 (d, J = 7.6 Hz, 1H), 6.66 (d, J = 7.6 Hz, 1H), 6.84 (t, J = 7.6 Hz, 1H), 6.90-7.20 (m, 5H). |
| III-4 | 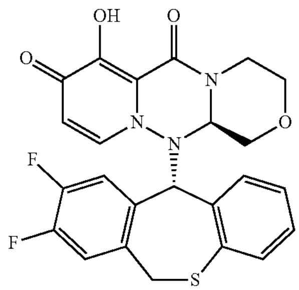 [SMILES: O=C1c2c(O)c(=O)ccn2N([C@H]2c3cc(F)c(F)cc3CSc3ccccc32)[C@@H]2COCCN12] | 1H-NMR(CDCl3)δ: 3.04 (t, J = 12.8 Hz, 1H), 3.40-3.62 (m, 3H), 3.82 (d, J = 12.0 Hz, 1H), 3.96 (d, J = 11.2 Hz, 1H), 4.58 (d, J = 9.6 Hz, 1H), 4.68 (d, J = 13.6 Hz, 1H), 4.57 (d, J = 13.6 Hz, 1H), 5.19 (s, 1H), 5.49 (d, J = 13.6 Hz, 1H), 5.74 (d, J = 7.6 Hz, 1H), 6.68 (d, J = 7.2 Hz, 1H), 6.85 (t, J = 7.6 Hz, 1H), 7.03 (d, J = 7.6 Hz, 1H), 7.06-7.16 (m, 3H), 7.21 (t, J = 8.8 Hz, 1H). |
| III-5 | 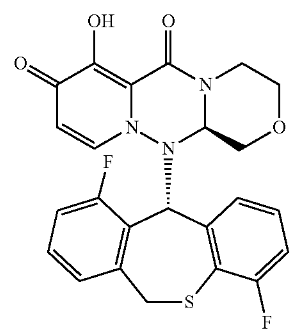 [SMILES: O=C1c2c(O)c(=O)ccn2N([C@@H]2c3cccc(F)c3SCc3cccc(F)c32)[C@@H]2COCCN12] | 1H-NMR(CDCl3)δ: 3.04 (t, J = 12.0 Hz, 1H), 3.47 (t, J = 12.0 Hz, 1H), 3.58 (t, J = 10.8 Hz, 1H), 3.69 (d, J = 13.6 Hz, 1H), 3.81 (d, J = 12.0 Hz, 1H), 3.94 (d, J = 11.2 Hz, 1H), 4.57 (d, J = 13.6 Hz, 1H), 4.69 (d, J = 14.0 Hz, 1H), 5.59 (d, J = 13.6 Hz, 1H), 5.79 (d, J = 7.6 Hz, 1H), 5.96 (s, 1H), 6.63 (d, J = 7.6 Hz, 1H), 6.81-6.88 (m, 1H), 6.96 (t, J = 9.6 Hz, 1H), 7.04-7.13 (m, 2H), 7.17 (d, J = 7.6 Hz, 1H), 7.38-7.45 (m, 1H). |
| III-6 | 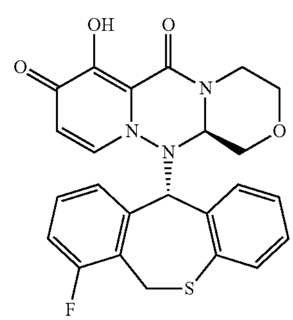 [SMILES: O=C1c2c(O)c(=O)ccn2N([C@@H]2c3ccccc3SCc3c(F)cccc32)[C@@H]2COCCN12] | 1H-NMR(CDCl3) δ: 2.95-3.03 (m, 1H), 3.43-3.49 (m, 2H), 3.59 (t, J = 10.6 Hz, 1H), 3.81 (dd, J = 12.0, 3.2 Hz, 1H), 3.97 (dd, J = 11.2, 3.0 Hz, 1H), 4.08 (d, J = 13.7 Hz, 1H), 4.60 (dd, J = 10.0, 3.0 Hz, 1H), 4.67 (dd, J = 13.6, 2.3 Hz, 1H), 5.23 (dd, J = 13.7, 2.1 Hz, 1H), 5.31 (s, 1H), 5.76 (d, J = 7.7 Hz, 1H), 6.70 (d, J = 7.5 Hz, 1H), 6.81-6.86 (m, 1H), 7.02-7.14 (m, 4H), 7.20-7.30 (m, 1H). |
| III-7 | 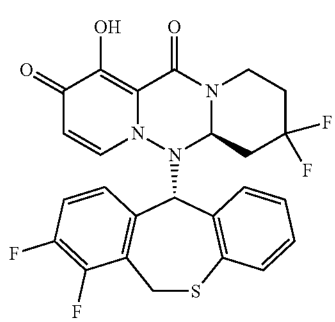 [SMILES: O=C1c2c(O)c(=O)ccn2N([C@@H]2c3ccccc3SCc3c2ccc(F)c3F)[C@@H]2CC(F)(F)CCN12] | 1H-NMR(CDCl3)δ: 1.85-1.98 (m, 1H), 2.10-2.23 (m, 2H), 2.31-2.43 (m, 1H), 2.69 (t, J = 10.8 Hz, 1H), 4.09 (d, J = 13.2 Hz, 1H), 4.51 (d, J = 12.4 Hz, 1H), 4.77 (d, J = 13.6 Hz, 1H), 5.20-5.30 (m, 1H), 5.78 (d, J = 7.2 Hz, 1H), 5.77 (d, J = 7.6 Hz, 1H), 6.68 (d, J = 7.2 Hz, 1H), 6.81-6.88 (m, 1H), 6.96-7.02 (m, 1H), 7.05-7.17 (m, 4H). |

TABLE 1-continued

| No. | Structure | H-NMR or LC/MS |
|---|---|---|
| III-8 | 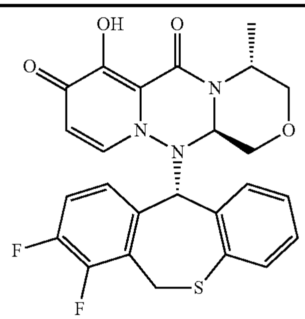 | 1H-NMR(CDCl3) δ: 1.22 (d, J = 7.2 Hz, 3H), 3.49-3.58 (m, 4H), 3.95 (dd, J = 10.8, 2.8 Hz, 1H), 4.08 (d, J = 13.8 Hz, 1H), 4.74 (dd, J = 10.0, 2.8 Hz, 1H), 4.99-5.05 (m, 1H), 5.22 (s, 1H), 5.30 (dd, J = 13.8, 2.3 Hz, 1H), 5.75 (d, J = 7.8 Hz, 1H), 6.69 (d, J = 7.7 Hz, 1H), 6.84 (t, J = 7.0 Hz, 1H), 6.97-7.02 (m, 2H), 7.08-7.14 (m, 3H). |

TABLE 2

| No. | Structure | H-NMR or LC/MS |
|---|---|---|
| III-9 | 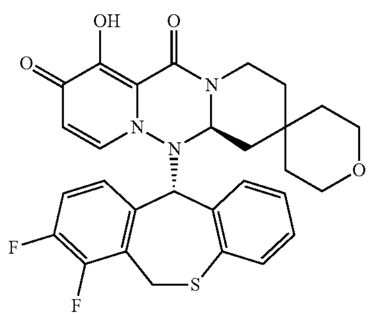 [SMILES: O=C1c2c(O)c(=O)ccn2N([C@@H]2c3ccccc3SCc3c2ccc(F)c3F)[C@@H]2CC3(CCOCC3)CCN12] | 1H-NMR (CDCl3) δ: 1.29-1.87 (m, 8H), 2.67 (td, J = 13.5, 2.6 Hz, 1H), 3.54-3.66 (m, 5H), 4.08 (d, J = 13.7 Hz, 1H), 4.47 (dd, J = 12.0, 2.3 Hz, 1H), 4.61 (dd, J = 13.8, 3.1 Hz, 1H), 5.24-5.33 (m, 2H), 5.79 (d, J = 7.8 Hz, 1H), 6.68 (d, J = 7.5 Hz, 1H), 6.83-6.87 (m, 1H), 6.98-7.15 (m, 5H). |
| III-10 | 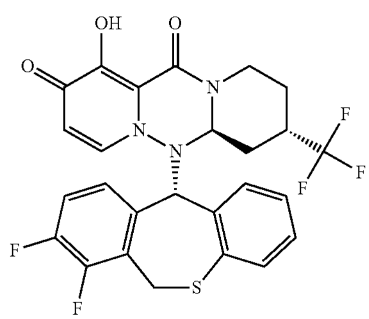 [SMILES: O=C1c2c(O)c(=O)ccn2N([C@@H]2c3ccccc3SCc3c2ccc(F)c3F)[C@@H]2C[C@@H](C(F)(F)F)CCN12] | 1H-NMR (CDCl3) δ: 1.82-2.17 (5H, m), 2.59-2.76 (1H, m), 2.84 (1H, t, J = 11.5 Hz) 4.09 (1H, d, J = 13.8 Hz), 4.63-4.69 (2H, m), 5.22 (1H, s), 5.27 (1H, dd, J = 13.9, 2.4 Hz), 5.79 (1H, d, J = 7.7 Hz), 6.68 (1H, d, J = 7.7 Hz), 6.83-6.87 (1H, m), 7.15-6.96 (5H, m). |
| III-11 | 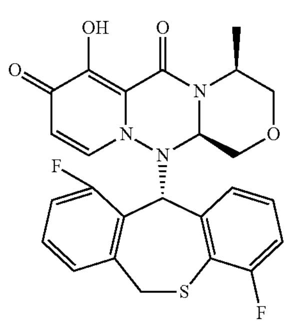 [SMILES: C[C@H]1COC[C@@H]2N1C(=O)c1c(O)c(=O)ccn1N2[C@@H]1c2cccc(F)c2SCc2cccc(F)c21] | 1H-NMR (CDCl3) δ: 1.79 (d, J = 7.2 Hz, 3H), 3.33-3.40 (m, 1H), 3.46-3.75 (m, 5H), 3.94 (dd, J = 11.0, 2.9 Hz, 1H), 4.43 (dd, J = 9.7, 2.7 Hz, 1H), 5.58 (d, J = 13.6 Hz, 1H), 5.81 (d, J = 7.7 Hz, 1H), 6.00 (s, 1H), 6.65 (d, J = 7.7 Hz, 1H), 6.82-6.88 (m, 1H), 6.94-7.01 (m, 2H), 7.11 (t, J = 9.2 Hz, 1H), 7.17 (d, J = 7.5 Hz, 1H), 7.39-7.44 (m, 1H). |

TABLE 2-continued
| No. | Structure | H-NMR or LC/MS |
|---|---|---|
| III-12 | 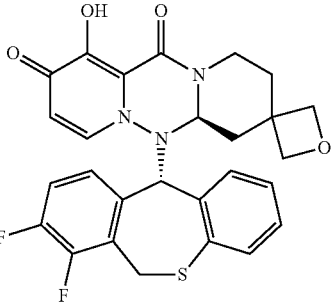 | 1H-NMR (CDCl3) δ: 1.62-1.69 (m, 1H), 1.90 (t, J = 12.4 Hz, 1H), 2.13 (d, J = 13.7 Hz, 1H), 2.38-2.46 (m, 2H), 4.09-4.20 (m, 3H), 4.32 (d, J = 6.3 Hz, 1H), 4.37-4.41 (m, 2H), 4.71 (dd, J = 13.7, 3.4 Hz, 1H), 5.23 (s, 1H), 5.36 (dd, J = 13.7, 2.6 Hz, 1H), 5.79 (d, J = 7.8 Hz, 1H), 6.68 (d, J = 7.8 Hz, 1H), 6.82-6.87 (m, 1H), 6.94-6.99 (m, 1H), 7.05-7.15 (m, 4H). |
| III-13 | 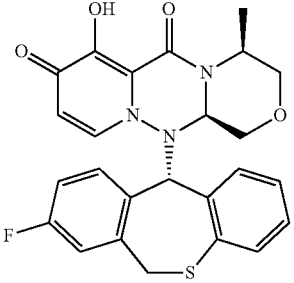 [SMILES: C[C@H]1COC[C@@H]2N1C(=O)c1c(O)c(=O)ccn1N2[C@H]1c2ccc(F)cc2CSc2ccccc21] | 1H-NMR (CDCl3) δ: 1.78 (d, J = 7.2 Hz, 3H), 3.26-3.32 (m, 1H), 3.44-3.60 (m, 3H), 3.72 (dd, J = 11.7, 2.6 Hz, 1H), 3.94 (dd, J = 11.2, 2.9 Hz, 1H), 4.42 (dd, J = 9.9, 2.8 Hz, 1H), 5.29 (s, 1H), 5.54 (d, J = 13.6 Hz, 1H), 5.76 (d, J = 7.8 Hz, 1H), 6.71 (d, J = 7.7 Hz, 1H), 6.81-6.86 (m, 1H), 6.96-7.04 (m, 2H), 7.07-7.11 (m, 3H), 7.23-7.25 (m, 1H). |
| III-14 | 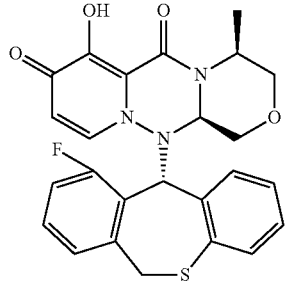 [SMILES: C[C@H]1COC[C@@H]2N1C(=O)c1c(O)c(=O)ccn1N2[C@@H]1c2ccccc2SCc2cccc(F)c21] | LC/MS (ESI): m/z = 480 [M + H]+, RT = 1.81 min, method (1) |
| III-15 | 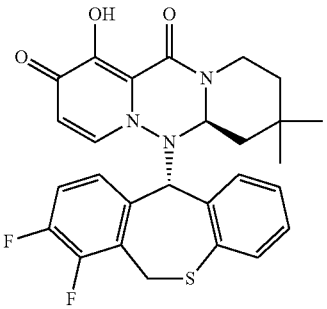 [SMILES: CC1(C)CCN2C(=O)c3c(O)c(=O)ccn3N([C@@H]3c4ccccc4SCc4c3ccc(F)c4F)[C@@H]2C1] | 1H-NMR (CDCl3) δ: 0.85(s, 3H), 0.97(s, 3H), 1.34-2.00(m, 4H), 2.62-2.66(m, 1H), 4.05(d, J = 13.6 Hz, 1H), 4.40-4.48(m, 1H), 4.56-4.63(m, 1H), 5.24(s, 1H), 5.30-5.35(s, 1H), 5.80(d, J = 7.6 Hz, 1H), 6.68(d, J = 7.6 Hz, 1H), 6.78-6.90(m, 1H), 6.95-7.15(m, 4H), 7.16-7.22(m, 1H) |

TABLE 3

| No. | Structure | H-NMR or LC/MS |
|---|---|---|
| III-16 | 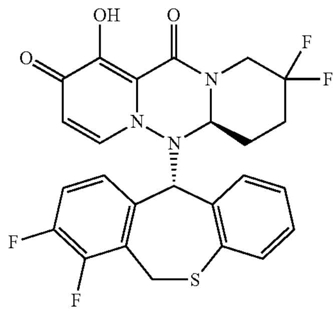 [SMILES: O=C1c2c(O)c(=O)ccn2N([C@@H]2c3ccccc3SCc3c2ccc(F)c3F)[C@@H]2CCC(F)(F)CN12] | 1H-NMR (CDCl3) δ: 1.86-2.18 (4H, m), 2.30-2.46 (1H, m), 2.90 (1H, dd, J = 30.0, 13.9 Hz), 4.07 (1H, d, J = 13.7 Hz), 4.41-4.48 (1H, m), 4.99-5.06 (1H, m), 5.20 (1H, s), 5.30 (1H, dd, J = 13.7, 2.4 Hz), 5.78 (1H, d, J = 7.8 Hz), 6.68 (1H, d, J = 7.8 Hz), 6.83-6.87 (1H, m), 7.00 (1H, dd, J = 8.3, 4.1 Hz), 7.06-7.17 (4H, m). |
| III-17 | 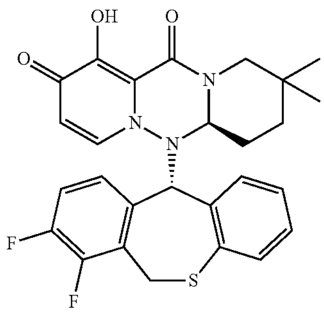 [SMILES: CC1(C)CC[C@@H]2N(C1)C(=O)c1c(O)c(=O)ccn1N2[C@@H]1c2ccccc2SCc2c1ccc(F)c2F] | 1H-NMR(CDCl3)δ: 0.89(s, 3H), 0.95(s, 3H), 1.25-2.20(m, 4H), 2.39(d, J = 12.4 Hz, 1H), 4.05(d, J = 12.4 Hz, 1H), 4.20-4.28(m, 1H), 4.39-4.44(m, 1H), 5.20(m, 1H), 5.33-5.38(m, 1H), 5.78(d, J = 7.6 Hz, 1H), 6.68(d, J = 7.6 Hz, 1H), 6.80-6.83(m, 1H), 6.88-7.18(m, 5H) |
| III-18 | 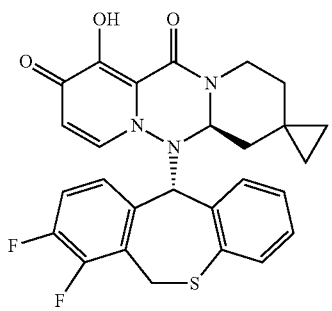 [SMILES: O=C1c2c(O)c(=O)ccn2N([C@@H]2c3ccccc3SCc3c2ccc(F)c3F)[C@@H]2CC3(CCN12)CC3] | 1H-NMR(CDCl3)δ: 0.18-0.25(m, 1H), 0.26-0.35(m, 1H), 0.36-0.50(m, 2H), 0.76-0.83(m, 1H), 0.98-1.40(m, 1H), 1.60-2.24(m, 4H), 2.60-2.70(m, 1H), 4.04(d, J = 13.6 Hz, 1H), 4.32-4.48(m, 1H), 4.69-4.75(m, 1H), 5.26(s, 1H), 5.77(d, J = 8.0 Hz, 1H), 6.69(d, J = 8.0 Hz, 1H), 6.80-6.90(m, 1H), 7.00-7.18(m, 5H) |
| III-19 | 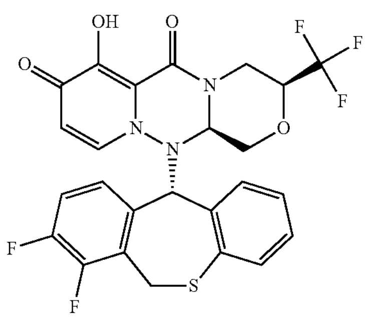 [SMILES: O=C1c2c(O)c(=O)ccn2N([C@@H]2c3ccccc3SCc3c2ccc(F)c3F)[C@@H]2CO[C@H](C(F)(F)F)CN12] | 1H-NMR(CDCl3) δ: 3.26 (dd, J = 14.6, 5.7 Hz, 1H), 3.85-4.11 (m, 4H), 4.68 (dd, J = 10.4, 3.6 Hz, 1H), 5.07 (d, J = 14.7 Hz, 1H), 5.22-5.27 (m, 2H), 5.74 (d, J = 7.7 Hz, 1H), 6.69 (d, J = 7.5 Hz, 1H), 6.85 (t, J = 6.9 Hz, 1H), 6.97-7.15 (m, 5H). |
| III-20 | 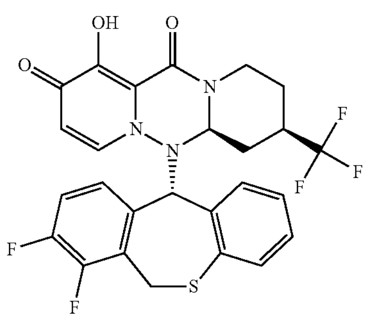 [SMILES: O=C1c2c(O)c(=O)ccn2N([C@@H]2c3ccccc3SCc3c2ccc(F)c3F)[C@@H]2C[C@H](C(F)(F)F)CCN12] | 1H-NMR (CDCl3) δ: 1.49-1.79 (m, 2H), 1.91 (d, J = 11.9 Hz, 1H), 2.08-2.13 (m, 1H), 2.47-2.62 (m, 2H), 4.07-4.10 (m, 1H), 4.35 (dd, J = 11.9, 2.3 Hz, 1H), 4.84 (dd, J = 13.4, 4.0 Hz, 1H), 5.25 (s, 1H), 5.31 (dd, J = 13.9, 2.4 Hz, 1H), 5.79 (d, J = 7.7 Hz, 1H), 6.69 (d, J = 7.9 Hz, 1H), 6.83-6.87 (m, 1H), 6.97-7.00 (m, 1H), 7.06-7.15 (m, 4H). |

TABLE 3-continued

| No. | Structure | H-NMR or LC/MS |
|---|---|---|
| III-21 | 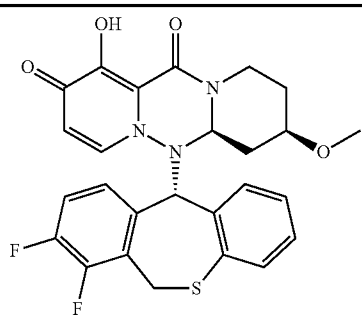 | 1H-NMR(CDCl3) δ: 1.31-1.44(m, 1H), 1.58 (q, J = 11.6 Hz, 1H), 2.05 (d, J = 10.8 Hz, 1H), 2.26 (d, J = 11.6 Hz, 1H), 2.47 (t, J = 11.2 Hz, 1H), 3.31 (s, 3H), 3.40-3.48 (m, 1H), 4.06 (d, J = 13.6 Hz, 1H), 4.24 (d, J = 10.0 Hz, 1H), 4.68-4.76 (m, 1H), 5.23 (s, 1H), 5.34 (d, J = 13.6 Hz, 1H), 5.78 (d, J = 7.6 Hz, 1H), 6.68 (d, J = 7.6 Hz, 1H), 6.84 (t, J = 7.6 Hz, 1H), 6.95-7.00 (m, 1H), 7.03-7.15 (m, 4H). |
| III-22 | 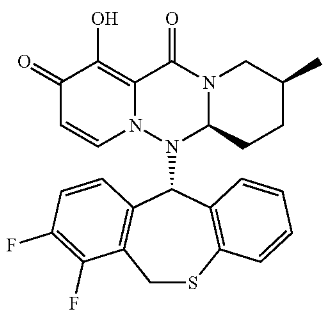 [SMILES: C[C@H]1CC[C@@H]2N(C1)C(=O)c1c(O)c(=O)ccn1N2[C@@H]1c2ccccc2SCc2c1ccc(F)c2F] | 1H-NMR (CDCl3) δ: 0.94 (3H, d, J = 7.2 Hz), 1.45-1.86 (5H, m), 1.86-2.12 (1H, m), 2.79 (1H, dd, J = 13.3, 3.5 Hz), 4.05 (1H, d, J = 13.7 Hz), 4.27 (1H, dd, J = 11.6, 2.4 Hz), 4.56 (1H, d, J = 13.2 Hz), 5.36 (1H, dd, J = 13.6, 2.4 Hz), 5.20 (1H, s), 5.79 (1H, d, J = 7.7 Hz), 6.69 (1H, d, J = 7.4 Hz), 6.81-6.87 (1H, m), 6.95-7.01 (1H, m), 7.05-7.14 (4H, m). |

TABLE 4

| No. | Structure | H-NMR or LC/MS |
|---|---|---|
| III-23 | 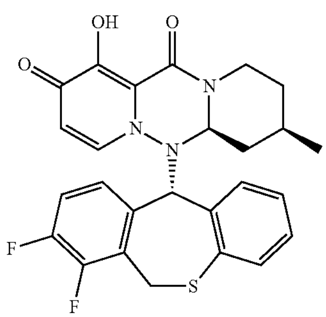 [SMILES: C[C@@H]1CCN2C(=O)c3c(O)c(=O)ccn3N([C@@H]3c4ccccc4SCc4c3ccc(F)c4F)[C@@H]2C1] | 1H-NMR (CDCl3) δ: 0.96 (3H, d, J = 6.5 Hz), 1.16-1.20 (1H, m), 1.34-1.40 (1H, m), 1.64-1.79 (3H, m),. 1.85-1.89 (1H, m), 2.52 (1H, td, J = 13.1, 2.6 Hz), 4.05 (1H, d, J = 13.8 Hz), 4.28 (1H, dd, J = 11.5, 2.2 Hz), 4.70 (1H, dd, J = 13.3, 3.6 Hz), 5.23 (1H, s), 5.36 (1H, dd, J = 13.7, 2.4 Hz), 5.79 (1H, d, J = 7.8 Hz), 6.68 (1H, d, J = 7.5 Hz), 6.82-6.86 (1H, m), 6.98 (1H, dd, J = 8.3, 5.3 Hz),7.02-7.15 (4H, m). |
| III-24 | 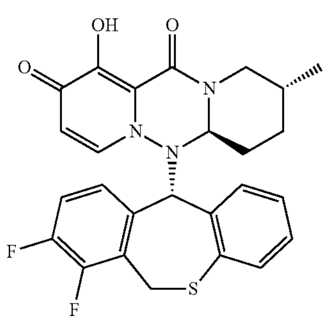 | 1H-NMR (CDCl3) δ: 0.91 (3H, d, J = 6.6 Hz), 1.22-1.29 (2H, m), 1.57-1.87 (5H, m), 1.96 (1H, d, J = 13.6 Hz), 2.18 (1H, t, J = 12.4 Hz), 4.05 (1H, d, J = 13.9 Hz), 4.25 (1H, dd, J = 11.4, 2.5 Hz), 4.57-4.65 (1H, m), 5.22 (1H, s), 5.35 (1H, dd, J = 13.8, 2.4 Hz), 5.78 (1H, d, J = 7.6 Hz), 6.68 (1H, d, J = 7.8 Hz), 6.82-6.86 (1H, m), 6.94-7.01 (1H, m), 7.03-7.15 (4H, m). |

TABLE 4-continued

| No. | Structure | H-NMR or LC/MS |
|---|---|---|
| III-25 | 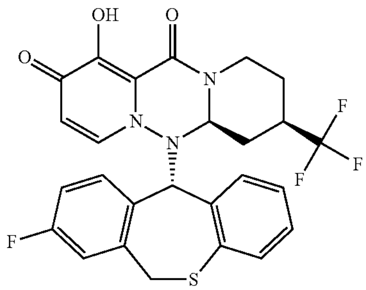 [SMILES: O=C1c2c(O)c(=O)ccn2N([C@H]2c3ccc(F)cc3CSc3ccccc32)[C@@H]2C[C@H](C(F)(F)F)CCN12] | 1H-NMR (CDCl3) δ: 1.55 (1H, ddd, J = 26.3, 13.0, 4.6 Hz), 1.74 (1H, q, J = 12.3 Hz), 1.89 (1H, d, J = 13.1 Hz), 2.09 (1H, d, J = 12.7 Hz), 2.58 (1H, td, J = 13.2, 2.6 Hz), 2.40-2.52 (1H, m), 3.54 (1H, d, J = 13.4 Hz), 4.35 (1H, dd, J = 11.7, 2.3 Hz), 4.84 (1H, dd, J = 13.4, 3.8 Hz), 5.23 (1H, s), 5.57 (1H, d, J = 13.4 Hz), 5.80 (1H, d, J = 7.7 Hz), 6.69 (1H, d, J = 7.7 Hz), 6.82-6.86 (1H, m), 6.98 (1H, td, J = 8.2, 2.6 Hz), 7.07-7.14 (4H, m), 7.20 (1H, dd, J = 8.3, 5.5 Hz). |
| III-26 | 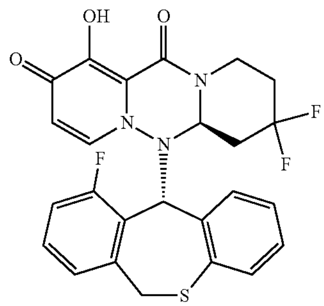 [SMILES: O=C1c2c(O)c(=O)ccn2N([C@@H]2c3ccccc3SCc3cccc(F)c32)[C@@H]2CC(F)(F)CCN12] | 1H-NMR(CDCl3)δ: 1.83-2.00 (m, 1H), 2.08-2.23 (m, 2H), 2.37 (t, J = 13.6 Hz, 1H), 2.74 (t, J = 13.2 Hz, 1H), 3.63 (d, J = 13.6 Hz, 1H) 4.51 (d, J = 11.6 Hz, 1H), 4.76-4.84 (m, 1H), 5.54 (d, J = 13.2 Hz, 1H), 5.79 (d, J = 8.0 Hz, 1H), 5.87 (s, 1H), 6.77 (d, J = 7.2 Hz, 1H), 6.85 (t, J = 7.2 Hz, 1H), 7.04-7.18 (m, 5H), 7.35-7.43 (m, 1H). |
| III-27 | 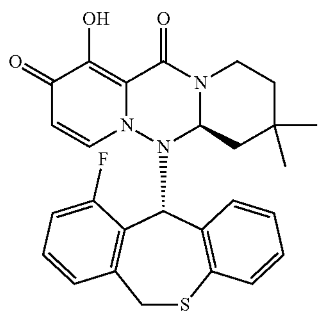 [SMILES: CC1(C)CCN2C(=O)c3c(O)c(=O)ccn3N([C@@H]3c4ccccc4SCc4cccc(F)c43)[C@@H]2C1] | 1H-NMR(CDCl3)δ: 0.82 (s, 3H), 0.96 (s, 3H), 1.30-1.61 (m, 4H), 2.71 (t, J = 13.2 Hz, 1H), 1.99 (d, J = 12.8 Hz, 1H), 2.54 (t, J = 12.8 Hz, 1H), 4.04 (d, J = 13.6 Hz, 1H), 4.27 (dd, J = 2.0 Hz, 11.2 Hz, 1H), 4.69-4.74 (m, 1H), 5.23 (s, 1H), 5.35 (dd, J = 2.4 Hz, 13.6 Hz, 1H), 5.77 (d, J = 7.6 Hz, 1H), 6.68 (d, J = 7.6 Hz, 1H), 6.80-6.86 (m, 1H), 6.95-7.00 (m, 1H), 7.03-7.14 (m, 4H). |
| III-28 | 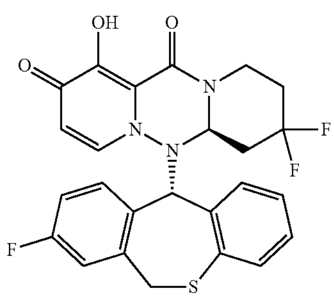 [SMILES: O=C1c2c(O)c(=O)ccn2N([C@H]2c3ccc(F)cc3CSc3ccccc32)[C@@H]2CC(F)(F)CCN12] | 1H-NMR(CDCl3)δ: 1.83-2.00 (m, 1H), 2.07-2.27 (m, 2H), 2.37 (t, J = 13.2 Hz, 1H), 2.67 (t, J = 13.2 Hz, 1H), 3.54 (d, J = 13.2 Hz, 1H), 4.51 (d, J = 11.2 Hz, 1H), 4.75-4.82 (m, 1H), 5.24 (s, 1H), 5.50 (d, J = 13.2 Hz, 1H), 5.77 (d, J = 7.2 Hz, 1H), 6.68 (d, J = 7.6 Hz, 1H), 6.80-6.86 (m, 1H), 6.95-7.02 (m, 1H), 7.05-7.14 (m, 4H), 7.16-7.23 (m, 1H) |
| III-29 | 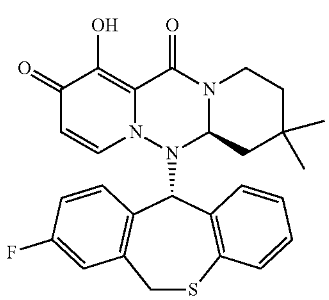 [SMILES: CC1(C)CCN2C(=O)c3c(O)c(=O)ccn3N([C@H]3c4ccc(F)cc4CSc4ccccc43)[C@@H]2C1] | 1H-NMR(CDCl3)δ: 0.82 (s, 3H), 0.97 (s, 3H), 1.24-1.44 (m, 2H), 1.46-1.60 (m, 2H), 2.58-2.68 (m, 1H), 3.50 (d, J = 13.2 Hz, 1H), 4.44 (dd, J = 2.8 Hz, 11.6 Hz, 1H), 4.57 (dd, J = 2.8 Hz, 13.2 Hz, 1H), 5.23 (s, 1H), 5.58 (d, J = 13.6 Hz, 1H), 5.78 (d, J = 7.6 Hz, 1H), 6.68 (d, J = 7.6 Hz, 1H), 6.80-6.86 (m, 1H), 6.95-7.03 (m, 2H), 7.05-7.13 (m, 3H), 7.18-7.24 (m, 1H). |

TABLE 5

| No. | Structure | H-NMR or LC/MS |
|---|---|---|
| III-30 | 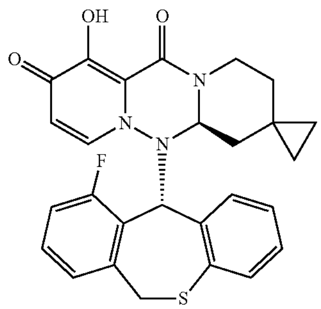 [SMILES: O=C1c2c(O)c(=O)ccn2N([C@@H]2c3ccccc3SCc3cccc(F)c32)[C@@H]2CC3(CCN12)CC3] | 1H-NMR(CDCl3)δ: 0.10-0.16 (m, 1H), 0.25-0.31 (m, 1H), 0.36-0.49 (m, 2H), 0.79 (d, J = 14.0 Hz, 1H), 0.99 (d, J = 12.8 Hz, 1H), 1.92-2.03 (m, 1H), 2.18 (t, J = 12.0 Hz, 1H), 2.65-2.77 (m, 1H), 3.58 (d, J = 13.6 Hz, 1H), 4.45 (dd, J = 2.4 Hz, 11.6 Hz, 1H), 4.73 (dd, J = 3.6 Hz, 13.2 Hz, 1H), 5.58 (d, J = 13.6 Hz, 1H), 5.81 (d, J = 7.6 Hz, 1H), 5.88 (s, 1H), 6.78 (d, J = 7.2 Hz, 1H), 6.81-6.88 (m, 1H), 7.05-7.16 (m, 5H), 7.34-7.43 (m, 1H). |
| III-31 | 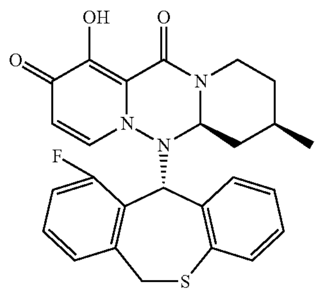 [SMILES: C[C@@H]1CCN2C(=O)c3c(O)c(=O)ccn3N([C@@H]3c4ccccc4SCc4cccc(F)c43)[C@@H]2C1] | 1H-NMR(CDCl3) δ: 0.95 (d, J = 6.5 Hz, 3H), 1.12-1.24 (m, 1H), 1.36 (dd, J = 24.1, 11.7 Hz, 1H), 1.48-1.75 (m, 2H), 1.86 (d, J = 12.7 Hz, 1H), 2.59 (td, J = 13.1, 2.8 Hz, 1H), 3.59 (d, J = 13.3 Hz, 1H), 4.28 (dd, J = 11.5, 2.4 Hz, 1H), 4.73 (dd, J = 13.6, 3.0 Hz, 1H), 5.66 (d, J = 13.3 Hz, 1H), 5.79 (d, J = 7.7 Hz, 1H), 5.85 (s, 1H), 6.77-6.79 (m, 1H), 6.82-6.86 (m, 1H), 7.03-7.11 (m, 3H), 7.14 (d, J = 7.7 Hz, 2H), 7.36 (td, J = 8.0, 5.5 Hz, 1H). |
| III-32 | 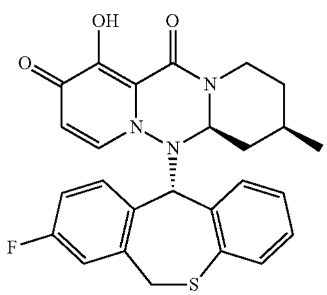 [SMILES: C[C@@H]1CCN2C(=O)c3c(O)c(=O)ccn3N([C@H]3c4ccc(F)cc4CSc4ccccc43)[C@@H]2C1] | 1H-NMR(CDCl3) δ: 0.95 (d, J = 6.5 Hz, 3H), 1.12-1.28 (m, 1H), 1.36 (q, J = 12.0 Hz, 1H), 1.63-1.78 (m, 3H), 1.86 (d, J = 12.8 Hz, 1H), 2.52 (td, J = 13.1, 2.8 Hz, 1H), 3.51 (d, J = 13.4 Hz, 1H), 4.28 (dd, J = 11.6, 2.3 Hz, 1H), 4.69 (dd, J = 13.5, 3.3 Hz, 1H), 5.22 (s, 1H), 5.62 (d, J = 13.4 Hz, 1H), 5.78 (d, J = 7.7 Hz, 1H), 6.68 (d, J = 7.7 Hz, 1H), 6.81-6.85 (m, 1H), 6.97 (td, J = 8.3, 2.6 Hz, 1H), 7.05-7.10 (m, 4H), 7.20 (dd, J = 8.4, 5.4 Hz, 1H). |
| III-33 | 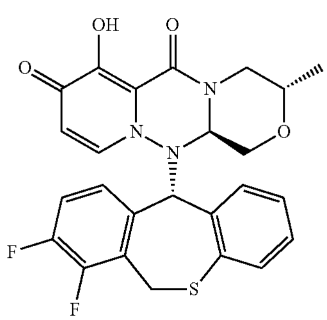 | 1H-NMR(CDCl3) δ: 1.17 (d, J = 6.1 Hz, 3H), 2.61 (dd, J = 13.3, 10.7 Hz, 1H), 3.54-3.59 (m, 1H), 3.64 (t, J = 10.6 Hz, 1H), 3.96 (dd, J = 11.1, 2.9 Hz, 1H), 4.07 (d, J = 13.8 Hz, 1H), 4.54 (dd, J = 10.0, 2.9 Hz, 1H), 4.64 (dd, J = 13.4, 2.3 Hz, 1H), 5.26-5.30 (m, 2H), 5.75 (d, J = 7.7 Hz, 1H), 6.68 (d, J = 7.7 Hz, 1H), 6.85 (t, J = 7.2 Hz, 1H), 6.98-7.03 (m, 2H), 7.07-7.15 (m, 3H). |
| III-34 | 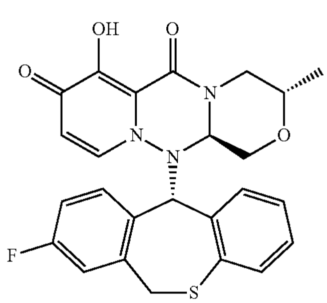 [SMILES: C[C@H]1CN2C(=O)c3c(O)c(=O)ccn3N([C@H]3c4ccc(F)cc4CSc4ccccc43)[C@@H]2CO1] | 1H-NMR(CDCl3)δ: 1.16 (d, J = 6.0 Hz, 3H), 2.55-2.65 (m, 1H), 3.48-3.60 (m, 2H), 3.64 (t, J = 10.4 Hz, 1H), 3.94 (dd, J = 2.8 Hz, 11.2 Hz, 1H), 4.54 (dd, J = 2.8 Hz, 10.0 Hz, 1H), 4.62 (dd, J = 2.0 Hz, 13.6 Hz, 1H), 5.25 (s, 1H), 5.54 (d, J = 13.2 Hz, 1H), 5.74 (d, J = 7.2 Hz, 1H), 6.68 (d, J = 7.2 Hz, 1H), 6.79-6.86 (m, 1H), 6.96-7.05 (m, 2H), 7.05-7.15 (m, 3H), 7.17-7.24 (m, 1H). |

Example 2

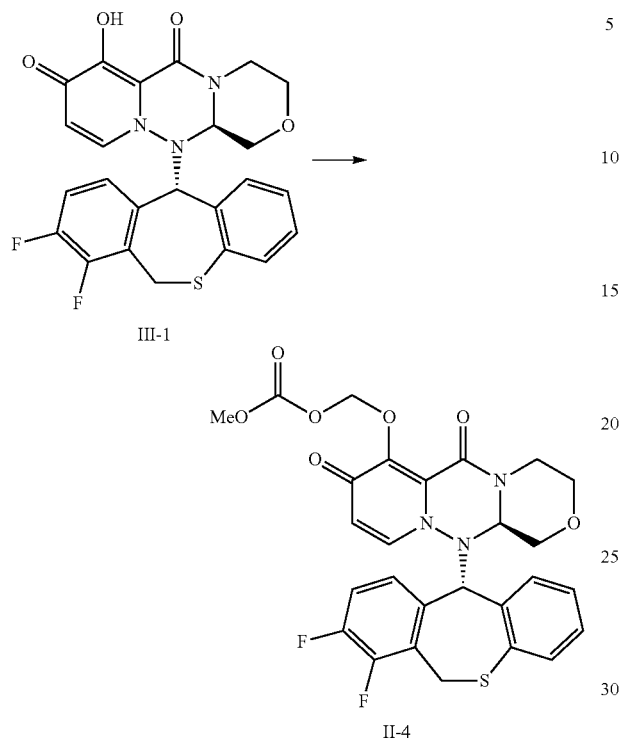

To a suspension of Compound III-1 (1.00 g, 2.07 mmol) in DMA (5 ml) were added chloromethyl methyl carbonate (0.483 g, 3.10 mmol), potassium carbonate (0.572 g, 4.14 mmol) and potassium iodide (0.343 g, 2.07 mmol) and the mixture was stirred at 50° C. for 6 hours. To the mixture was added DMA (1 ml) and the mixture was stirred for 6 hours. The mixture was cooled to room temperature, DMA (6 ml) was added thereto, and the mixture was stirred at 50° C. for 5 minutes. The mixture was filtered. To the obtained filtrate were added 1 mol/L aqueous solution of hydrochloric acid (10 ml) and water (4 ml) and the mixture was stirred for 1 hour. The presipitated solid was filtered and dried under reduced pressure at 60° C. for 3 hours to obtain Compound II-4 (1.10 g, 1.93 mmol, 93%).

1H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

Example 3

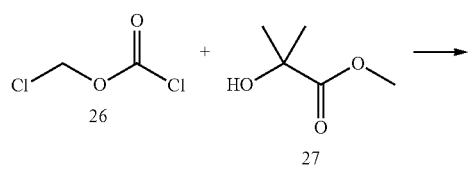

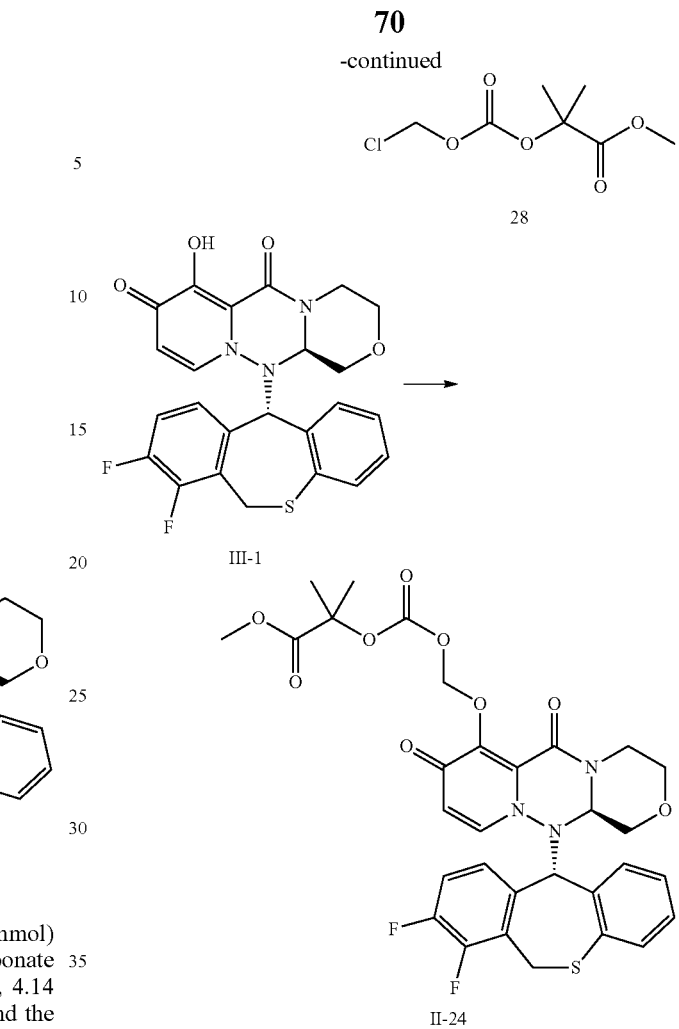

First Step

To a solution of chloromethyl chloroformate (300 mg, 2.33 mmol) and Compound 27 (330 mg, 2.79 mmol) in dichloromethane (6.0 mL) was added pyridine (207 μL, 2.56 mmol) at 0° C. under nitrogen atmosphere, and the mixture was stirred at 0° C. for 30 minutes, was warmed up to room temperature and was stirred for 1 hour. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure to obtain Compound 28 (440 mg, 90%).

1H-NMR (CDCl3) δ:1.65 (s, 6H), 3.77 (s, 3H), 5.71 (s, 2H).

Second Step

Compound III-1 (300 mg, 0.62 mmol), potassium carbonate (172 mg, 1.24 mmol), potassium iodide (103 mg, 0.62 mmol) and Compound 28 (261 mg, 1.24 mmol) were dissolved in DMA (3.0 mL) and the mixture was stirred at 80° C. for 3 hours. To the mixture was added 2 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was purified by silica gel column chromatography (chloroform-methanol) to obtain Compound II-24 (350 mg, 86%).

1H-NMR (CDCl3) δ:1.63 (s, 3H), 1.67 (s, 3H), 2.86-2.93 (m, 1H), 3.38-3.61 (m, 2H), 3.68-3.78 (m, 4H), 3.90-3.96

(m, 1H), 4.06 (d, J=14.0 Hz, 1H), 4.51 (dd, J=2.0 Hz, 9.6 Hz, 1H), 4.65 (d, J=12.4 Hz, 1H), 5.21 (d, J=14.4 Hz, 1H), 5.36 (s, 1H), 5.80-5.95 (m, 3H), 6.85-6.92 (m, 2H), 7.03-7.22 (m, 5H).

Example 4

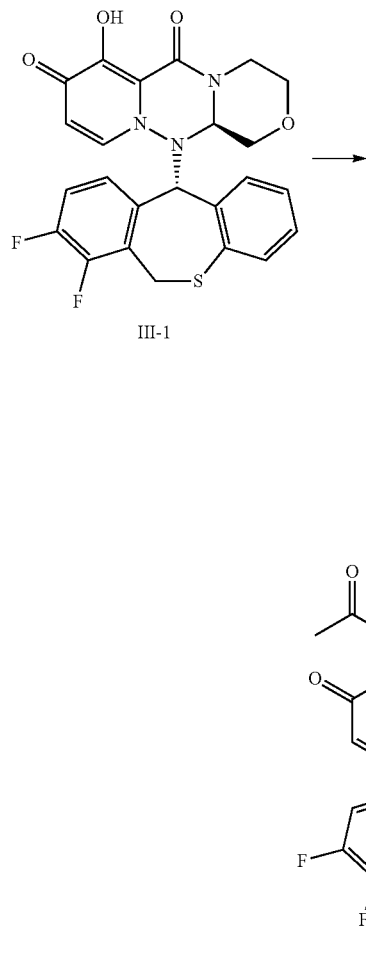

To a solution of Compound III-1 (90 mg, 0.186 mmol) in dichloromethane (2 mL) were added acetic anhydride (0.053 mL, 0.558 mmol), triethylamine (0.077 mL, 0.558 mmol) and a catalytic amount of DMAP, and the mixture was stirred at room temperature for 2 hours. The mixture was concentrated under reduced pressure and the obtained residue was purified by silica gel column chromatography (chloroform-methanol). To the obtained solution was added ether and the precipitated solid was filtered to obtain Compound II-2 (71 mg, 73%).

1H-NMR (CDCl3) δ:2.46 (s, 3H), 2.88-2.99 (m, 1H), 3.35-3.50 (m, 1H), 3.60-3.65 (m, 1H), 3.75-3.83 (m, 1H), 3.90-4.00 (m, 1H), 4.05 (d, J=14.0 Hz, 1H), 4.52-4.57 (m, 1H), 4.60-4.70 (m, 1H), 5.24-5.34 (m, 1H), 5.35 (s, 1H), 5.88 (d, J=7.6 Hz, 1H), 6.85-6.82 (m, 1H), 6.90-7.05 (m, 2H), 7.06-7.20 (m, 4H).

LC/MS (ESI):m/z=526.2 [M+H]+, RT=1.87 min, method (1)

Example 5

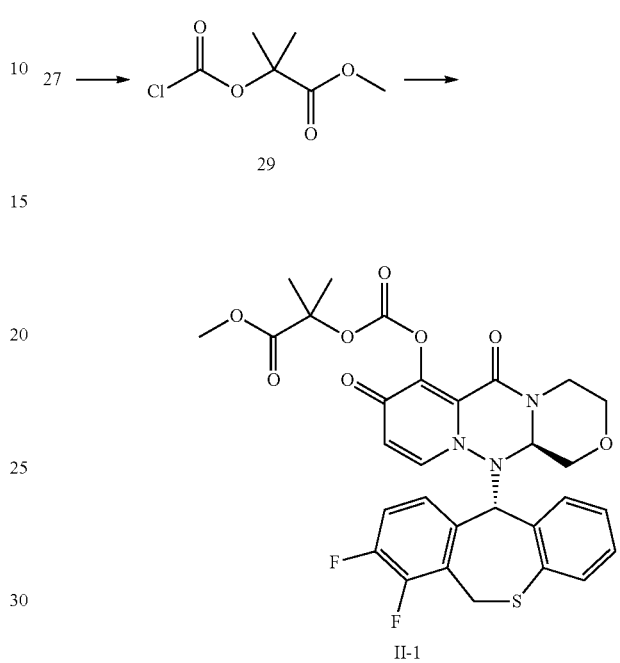

First Step

To a solution of triphosgene (300 mg, 2.54 mmol) in dichloromethane (6.0 mL) was added pyridine (257 μL, 3.17 mmol) at 0° C. under nitrogen atmosphere and the mixture was stirred for 15 minutes. To the mixture was added a solution of Compound 27 (377 mg, 1.27 mmol) in dichloromethane (1.0 mL), and the mixture was stirred at 0° C. for 15 minutes, warmed up to room temperature and stirred for 15 minutes. The mixture was concentrated under reduced pressure, ethyl acetate (4.0 mL) was added thereto, and the mixture was filtered. The filtrate was concentrated under reduced pressure to obtain Compound 29 (380 mg).

Second Step

To a solution of Compound III-1 (350 mg, 0.724 mmol) in dichloromethane (3.5 mL) were added Compound 29 (196 mg, 1.09 mmol) and triethylamine (301 μL, 2.17 mmol) at 0° C. and the mixture was stirred at 0° C. for 30 minutes. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure. The obtained residue was purified by silica gel column chromatography (chloroform-methanol) to obtain Compound II-1 (380 mg, 84%).

1H-NMR (CDCl3) δ:1.73 (s, 3H), 1.77 (s, 3H), 2.90-2.99 (m, 1H), 3.37-3.43 (m, 1H), 3.57 (t, J=8.8 Hz, 1H), 3.76 (dd, J=2.8 Hz, 12.0 Hz, 1H), 3.81 (s, 3H), 3.94 (dd, J=2.8 Hz, 10.8 Hz, 1H), 4.05 (d, J=14.0 Hz, 1H), 4.55 (dd, J=2.8 Hz, 9.6 Hz, 1H), 4.65 (d, J=12.0 Hz, 1H), 5.28 (d, J=12.0 Hz, 1H), 5.34 (s, 1H), 5.89 (d, J=8.0 Hz, 1H), 6.86-6.95 (m, 2H), 7.03-7.15 (m, 5H).

Example 6

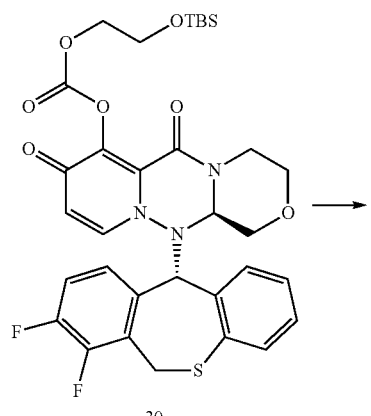

30

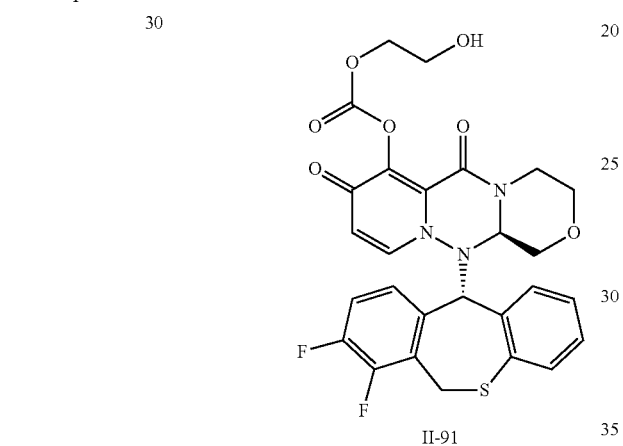

II-91

To a solution of Compound 30 (276 mg, 0.402 mmol) in THF (1 mL) were added acetic acid (121 mg, 2.01 mmol) and 1 mol/L TBAF in THF (1.21 mL, 1.21 mmol) under ice-water bath and the mixture was stirred at room temperature for 4 hours. The mixture was concentrated under reduced pressure. The obtained residue was purified by silica gel column chromatography (ethyl acetate-methanol) to obtain Compound II-91 (179 mg, 78%).

LC/MS (ESI):m/z=572.0 [M+H]$^+$, RT=1.74 min, method (2)

Example 7

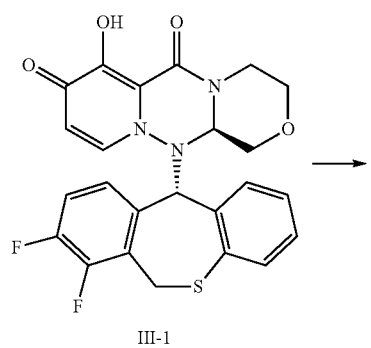

III-1

-continued

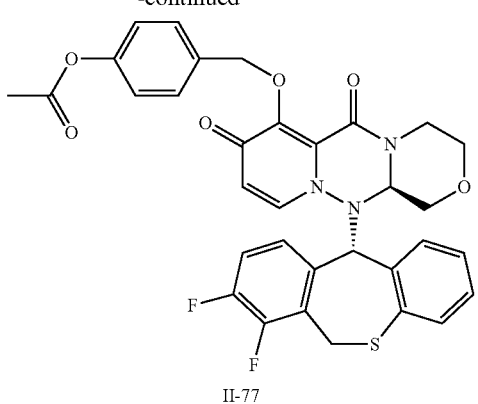

II-77

To a solution of Compound III-1 (300 mg, 0.62 mmol) in DMF (4 mL) were added potassium carbonate (258 mg, 1.87 mmol), 4-(chloromethyl)phenyl acetate (344 mg, 1.87 mmol) and sodium iodide (139 mg, 1.87 mmol) at room temperature and the mixture was stirred at 65° C. for 1 hour. To the mixture was added water and the mixture was extracted with ethyl acetate. The obtained organic layer was washed with water, dried over anhydrous sodium sulfate, and concentrated under reduced pressure. The obtained residue was purified by silica gel column chromatography (ethyl acetate-methanol) to obtain Compound II-77 (120 mg, 31%).

LC/MS (ESI):m/z=631.95 [M+H]$^+$, RT=2.07 min, method (2)

Example 8

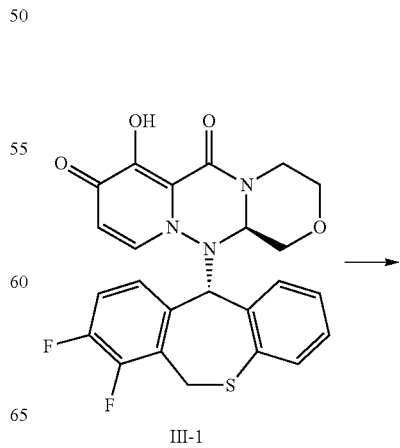

III-1

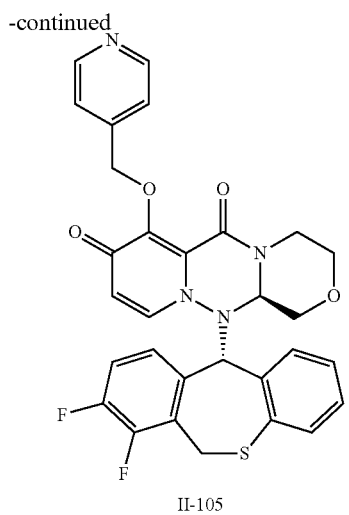

II-105

To a solution of Compound III-1 (150 mg, 0.31 mmol) in dichloromethane (2 mL) 3 mmol/g triphenylphosphine supported on polymer (310 mg, 0.93 mmol), pyridin-4-ylmethanol (68 mg, 0.62 mmol) and 40% DEAD in toluene (270 mg, 0.62 mmol) at room temperature and the mixture was stirred at room temperature for 30 minutes. The mixture was purified by amino column chromatography (ethyl acetate-methanol) to obtain Compound II-105 (63 mg, 35%).

LC/MS (ESI):m/z=575.00 [M+H]$^+$, RT=1.43 min, method (2)

Example 9

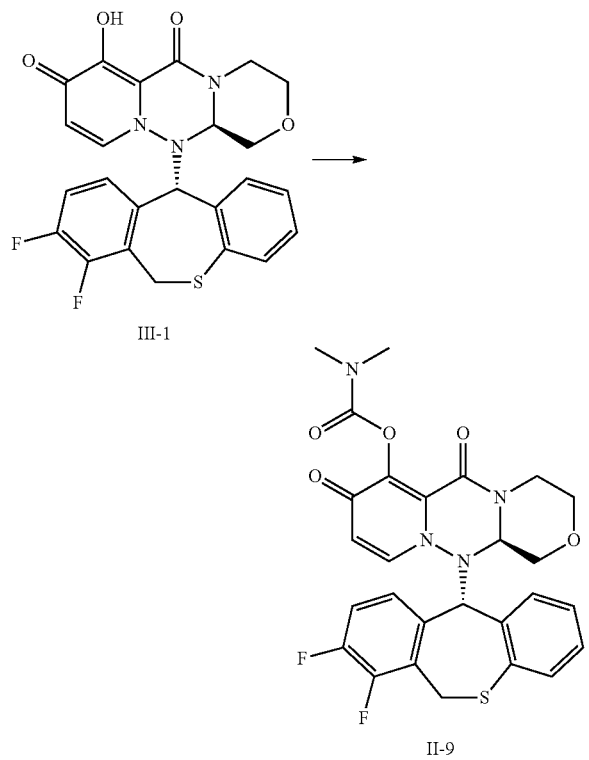

III-1

II-9

To a solution of Compound III-1 (65 mg, 0.134 mmol) in pyridine (0.8 mL) was added dimethylcarbamoyl chloride (21.7 mg, 0.202 mmol) and the mixture was stirred at 80° C. over night. To the mixture was added 1 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was solidified with ethyl acetate-hexane to obtain Compound II-9 (65 mg, 87%).

1H-NMR (CDCl3) δ:2.89 (t, J=11.2 Hz, 1H), 2.99 (s, 1H), 3.01 (s, 3H), 3.18-3.26 (m, 4H), 3.45 (t, J=10.8 Hz, 1H), 3.59 (t, J=10.8 Hz, 1H), 3.70-3.80 (m, 1H), 3.90-3.98 (m, 1H), 4.03 (d, J=13.6 Hz, 1H), 4.50-4.70 (m, 2H), 5.21-5.35 (m, 2H), 5.82 (d, J=7.6 Hz, 1H), 6.91 (t, J=7.6 Hz, 1H), 7.00-7.20 (m, 6H).

Example 10

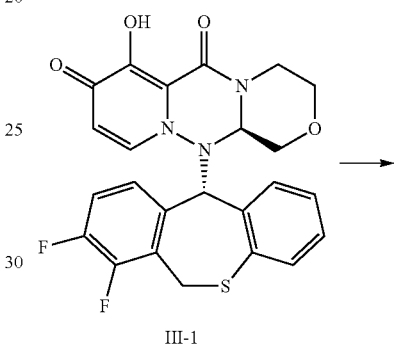

III-1

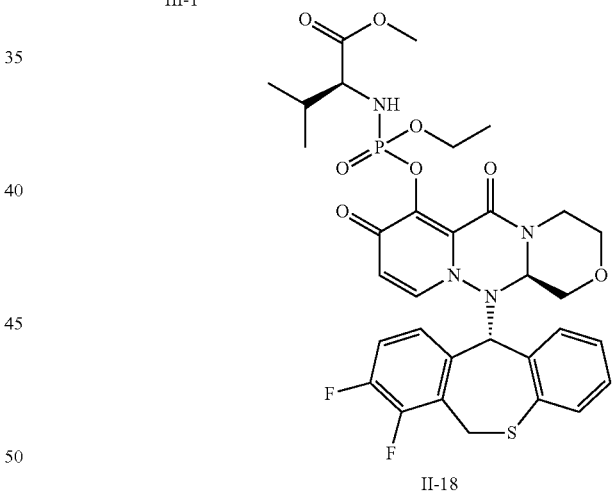

II-18

To a solution of ethyl phosphorodichloridate (135 mg, 0.829 mmol) in dichloromethane (3 mL) was added L-valine methyl ester hydrochloride (139 mg, 0.829 mmol) and then added dropwise a solution of triethylamine (168 mg, 1.66 mmol) in dichloromethane (2 mL) at −78° C. The mixture was stirred at room temperature for 1 hour. Compound III-1 (200 mg, 0.414 mmol) and triethylamine (126 mg, 1.25 mmol) were added thereto, and the mixture was stirred at same temperature for 6 hours. The mixture was concentrated and the obtained residue was purified by silica gel column chromatography (ethyl acetate-methanol) to obtain Compound II-18 (112 mg, 38%).

LC/MS (ESI):m/z=705.05 [M+H]$^+$, RT=2.18 min, method (2)

Example 11

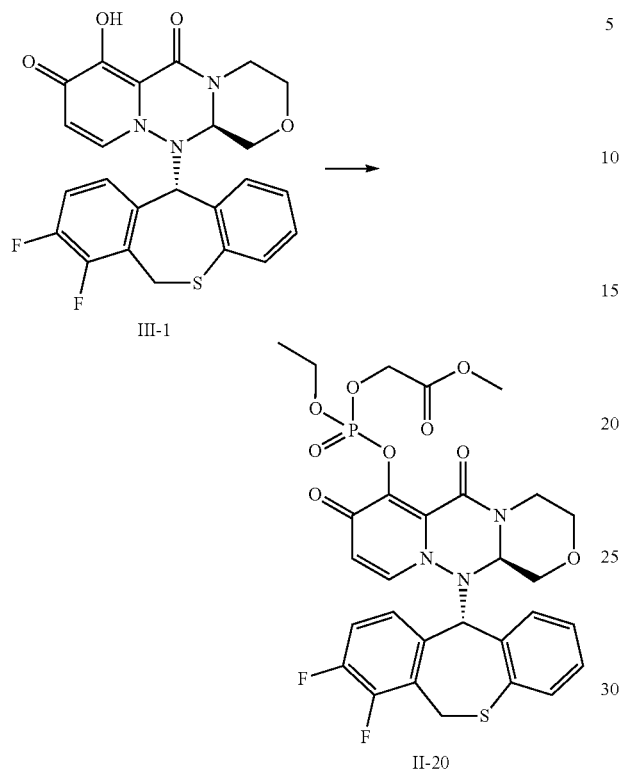

To a solution of ethyl phosphorodichloridate (202 mg, 1.24 mmol) in dichloromethane (3 mL) was added dropwise a mixture of triethylamine (126 mg, 1.24 mmol) and methyl glycolate (112 mg, 1.24 mmol) in dichloromethane (2 mL). The mixture was stirred at room temperature for 2 hours. Compound III-1 (200 mg, 0.414 mmol) and triethylamine (126 mg, 1.25 mmol) were added thereto and the mixture was stirred at same temperature for 1 hour. The mixture was concentrated and the obtained residue was purified by silica gel column chromatography (ethyl acetate-methanol) to obtain Compound II-20 (143 mg, 52%).

LC/MS (ESI):m/z=664.00 [M+H]$^+$, RT=1.93 min, method (2)

Example 12

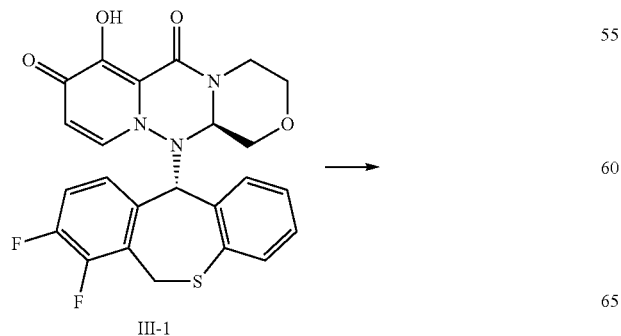

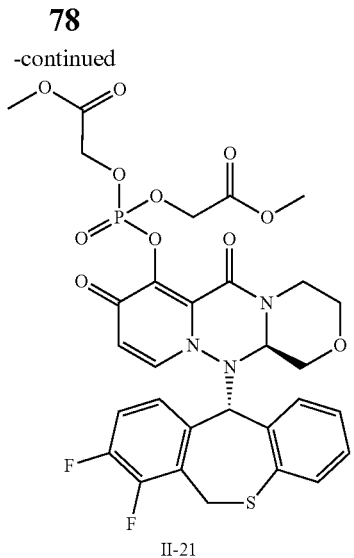

To a solution of phosphoryl chloride (1.53 g, 10 mmol) in dichloromethane (10 mL) was added dropwise the mixture of triethylamine (2.12 g, 20.95 mmol) and methyl glycolate (1.89 mg, 21 mmol) in dichloromethane (5 mL). The mixture was stirred at room temperature for 2 hours. To the mixture (2 mL) were added Compound III-1 (200 mg, 0.414 mmol) and triethylamine (126 mg, 1.25 mmol) and the mixture was stirred at same temperature for 1 hour. The mixture was concentrated and the obtained residue was purified by silica gel column chromatography (ethyl acetate-methanol) to obtain Compound II-21 (166 mg, 57%).

LC/MS (ESI):m/z=707.90 [M+H]$^+$, RT=1.93 min, method (2)

Example 13

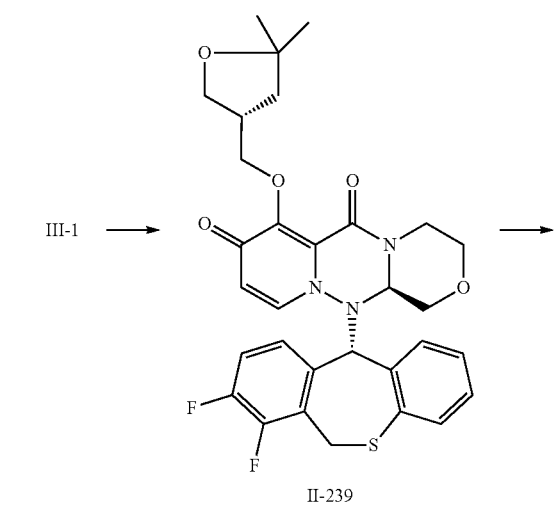

-continued

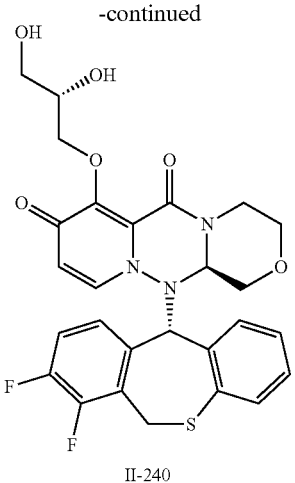

II-240

First Step

To a solution of (R)-(2,2-dimethyl-1,3-dioxolan-4-yl)methanol (492 mg, 3.72 mmol) in THF (6.0 mL) was added Compound III-1 (300 mg, 0.620 mmol) and PPh$_3$ (651 mg, 2.482 mmol) at 0° C. and the mixture was stirred. To the mixture was added dropwise DIAD (1.3 mL, 2.482 mmol), and the mixture was stirred for 3 hours. The mixture was concentrated and the obtained residue was purified by silica gel column chromatography (chloroform-methanol) to obtain Compound II-239 (130 mg, 35%).

LC/MS (ESI):m/z=558 [M+H]$^+$, RT=1.66 min, method (2)

Second Step

To a solution of Compound II-239 in ethanol (2.4 mL) was added 4-methylbenzenesulfonic acid (13.83 mg, 0.080 mmol) and the mixture was stirred for 4 hours. The mixture was concentrated and the obtained residue was purified by silica gel column chromatography (chloroform-methanol) to obtain Compound II-240 (52 mg, 70%).

LC/MS (ESI):m/z=558 [M+H]$^+$, RT=1.66 min, method (2)

The following example compounds were synthesized from commercially available compounds according to the above examples.

TABLE 6

| No. | PR | data | comment |
|---|---|---|---|
| II-3 | acetoxymethyl | 1H-NMR(DMSO-d6)δ: 2.04(s, 3H), 2.90-3.00(m, 1H), 3.44-3.50(m, 3.64 -3.72(m, 1H), 3.95-4.00(m, 1H), 4.11-4.10(m, 1H), 4.20-4.30(m, 2H), 5,40-5.5.46(m, 1H), 6.62-5.75(m, 4H), 6.80-6.90(m, 1H), 6.98-7.10(m, 1H), 7.11-7.20(m, 2H), 7.21-7.30(m, 1H), 7.45-7.50(m, 2H) | |
| II-5 | methoxyethyl carbonate methyl | 1H-NMR(CDCl3)δ: 2.85-2.97 (m, 1H), 3.38 (s, 3H), 3.39-3.48 (m, 1H), 3.54 (t, J = 10.4 Hz, 1H), 3.68 (t, J = 4.4 Hz, 2H), 3.74 (dd, J = 2.8 Hz, 12.0 Hz, 1H), 3.92 (dd, J = 2.8 Hz, 10.8 Hz, 1H), 4.05 (d, J = 13.6 Hz, 1H), 4.36 (q, J = 4.4 Hz, 2H), 4.51 (dd, J = 2.8 Hz, 9.6 Hz, 1H), 4.66 (d, J = 12.0 Hz, 1H), 5.27 (dd, J = 2.0 Hz, 13.6 Hz, 1H), 5.34 (s, 1H), 5.86 (d, J = 8.0 Hz, 1H), 5.93 (s, 2H), 6.81-6.89 (m, 2H), 6.98-7.15 (m, 5H). | |
| II-6 | propionyl | 1H-NMR (CDCl3)δ: 1.33 (3H, t, J = 7.0 Hz), 2.82 (2H, d, J = 6.1 Hz), 2.93 (1H, t, J = 11.2 Hz), 3.42 (1H, t, J = 11.4 Hz), 3.59 (1H, t, J = 10.2 Hz), 3.78 (1H, d, J = 11.2 Hz). 3.96 (1H. d. J = 10.3 Hz), 4.06 (1H, d, J = 13.8 Hz), 4.55 (1H, d, J = 8.9 Hz), 4.63 (1H, d, J = 13.6 Hz), 5.29 (1H, d, J = 13.9 Hz), 5.36 (1H, s), 5.88 (1H, d, J = 7.4 Hz), 6.90 (1H, s), 7.03-7.12 (6H, m). | |
| II-7 | isobutyryl | 1H-NMR (CDCl3)δ: 1.42 (d, J = 6.8 Hz, 6H), 2.85-3.05 (m, 2H), 3.40-3.49 (m, 1H), 3.69 (t, J = 10.4 Hz, 1H), 3.76 (d, J = 11.4 Hz, 1H), 3.94 (d, J = 10.4 Hz, 1H), 4.06 (d, J = 14.1 Hz. 1H), 4.51-4.57 (m, 1H), 4.59-4.70 (m, 1H), 5.25-5.32 (m, 1H), 5.35-5.39 (m, 1H), 5.80-5.89 (m, 1H), 6.85-7.15 (m, 7H). | |
| II-8 | methyl carbonate | LC/MS (ESI): m/z = 542 [M + H]$^+$, RT = 1.92 min, method (1) | |

TABLE 6-continued

| No. | PR | data | comment |
|---|---|---|---|
| II-10 | *N-methylpiperazine carbonyl* | LC/MS (ESI): m/z = 610 [M + H]+, RT = 1.57 min, method (1) | |
| II-11 | *butanoyl* | LC/MS (ESI): m/z = 554 [M + H]+, RT = 2.10 min, method (1) | |
| II-12 | *benzyl* | 1H-NMR (CDCl3)δ: 2.88 (1H, t, J = 11.2 Hz), 3.28-3.39 (2H, m), 3.72 (1H, d, J = 12.6 Hz), 3.86 (1H, d, J = 9.6 Hz), 4.03 (1H, d, J = 13.9 Hz), 4.45 (1H, d, J = 8.6 Hz), 4.67 (1H, d, J = 13.1 Hz), 5.19-5.26 (2H, m), 5.45 (1H, d, J = 10.9 Hz), 5.63 (1H, d, J = 10.9 Hz), 5.77 (1H, d, J = 7.6 Hz), 6.40 (1H, d, J = 7.8 Hz), 6.68 (1H, t, J = 6.9 Hz), 6.94-7.01 (2H, m), 7.03-7.12 (3H, m), 7.29-7.38 (3H, m), 7.61 (2H, d, J = 7.1 Hz). | |
| II-13 | *ethoxycarbonyl* | 1H-NMR (CDCl3)δ: 1.46 (t, J = 7.2 Hz, 3H), 2.95 (m, 1H), 3.42 (td, J = 12.0. 2.4 Hz, 1H), 3.68 (t, J = 10.4Hz, 1H), 3.78 (dd, J = 12.0, 2.8 Hz, 1H), 3.95 (dd, J = 11.2, 2.8 Hz, 1H), 4.07 (d, J = 13.6 Hz, 1H), 4.41 (m, 2H), 4.56 (dd, J = 10.0, 2.8 Hz, 1H), 4.67 (dd, J = 10.0, 2.4 Hz, 1H), 5.29 (dd, J = 13.6, 2.0 Hz, 1H), 5.36 (s, 1H), 5.91 (d, J = 8.0 Hz, 1H), 6.88-7.15 (m, 7H). | |

TABLE 7

| No. | PR | data | comment |
|---|---|---|---|
| II-14 | *isopropoxycarbonyl* | 1H-NMR (CDCl3)δ: 1.46 (m, 6H), 2.95 (m, 1H), 3.41 (td, J = 12.0, 2.0 Hz, 1H), 3.58 (t, J = 10.8 Hz, 1H), 3.77 (dd, J = 12.0, 3.2 Hz, 1H), 3.95 (dd, J = 10.8, 2.4Hz, 1H), 4.06 (d, J = 14.0 Hz, 1H), 4,55 (dd, J = 9.6, 2.8 Hz, 1H), 4.67 (d, J = 13.6 Hz, 1H), 5.04 (m, 1H), 5.29 (d, J = 13.6 Hz, 1H), 5.36 (s, 1H), 5.90 (d, J = 8.0 Hz, 1H), 6.90-7.13 (m, 7H). | |
| II-15 | *4-nitrobenzoyloxymethyl* | LC/MS (ESI): m/z = 663 [M + H]+, RT = 2.29 min, method (1) | |
| II-16 | *methyl 3,3-dimethyl-4-oxo ester* | LC/MS (ESI): m/z = 626 [M + H]+, RT = 2.18 min, method (1) | |

TABLE 7-continued

| No. | PR | data | comment |
|---|---|---|---|
| II-17 | (methyl 4-oxobutanoate group) | LC/MS (ESI): m/z = 598 [M + H]+, RT = 1.96 min, method (2) | |
| II-19 | (4-methyl-2-oxo-1,3-dioxol-5-yl)methyl | LC/MS (ESI): m/z = 596 [M + H]+, RT = 1.93 min, method (2) | |
| II-22 | (isopropyl (ethoxycarbonyl)-L-alaninyl phosphoramidate) | LC/MS (ESI): m/z = 705 [M + H]+, RT = 2.16 min, method (2) | |
| II-23 | (ethyl (ethoxycarbonyl)-L-alaninyl phosphoramidate) | LC/MS (ESI): m/z = 691 [M + H]+, RT = 2.08 min, method (2) | |
| II-25 | (3-isobenzofuranonyl) | LC/MS (ESI): m/z = 616 [M + H]+, RT = 2.07 min, method (2) | |
| II-26 | (3-methyl-5H-furan-2-one-5-yl) | LC/MS (ESI): m/z = 580 [M + H]+, RT = 1.92 min, method (2) | |
| II-27 | (ethyl methyl (S)-succinate) | LC/MS (ESI): m/z = 642 [M + H]+, RT = 2.05 min, method (2) | |
| II-28 | (cyclohexyl 1-ethylcarbonate) | LC/MS (ESI): m/z = 654 [M + H]+, RT = 2.43, 2.51 min, method (2) | |
| II-29 | (ethyl 1-ethylcarbonate) | LC/MS (ESI): m/z = 600 [M + H]+, RT = 2.05, 2.11 min, method (2) | |
| II-30 | (1,3-dioxolan-2-one-4-yl) | LC/MS (ESI): m/z = 570 [M + H]+, RT = 1.84 min, method (2) | |
| II-31 | (pivaloyl) | LC/MS (ESI): m/z = 568 [M + H]+, RT = 2.17 min, method (2) | |

TABLE 8

| No. | PR | data | comment |
|---|---|---|---|
| II-32 | (pivaloyloxymethyl group) | LC/MS (ESI): m/z = 598 [M + H]+, RT = 2.23 min, method (2) | |
| II-33 | (N-methyl-N-(ethoxycarbonyl)aminomethyl group) | LC/MS (ESI): m/z = 599 [M + H]+, RT = 1.99 min, method (2) | |
| II-34 | (2-methyl-2-(methoxycarbonyl)propanoyloxymethyl group) | LC/MS (ESI): m/z = 656 [M + H]+, RT = 2.13 min, method (2) | |
| II-35 | (ethoxy-(N-(methoxycarbonyl)-leucinyl)phosphoramidate group) | LC/MS (ESI): m/z = 719 [M + H]+, RT = 2.28 min, method (2) | |
| II-36 | (N-(methoxycarbonyl)prolyl group) | LC/MS (ESI): m/z = 639 [M + H]+, RT = 1.89 min, method (2) | |
| II-37 | (N-(methoxycarbonylmethoxycarbonyl)prolyl group) | LC/MS (ESI): m/z = 669 [M + H]+, RT = 1.97 min, method (2) | |
| II-38 | (1-(methoxycarbonyl)-1H-indol-3-ylmethyl group) | LC/MS (ESI): m/z = 671 [M + H]+, RT = 2.24 min, method (2) | |
| II-39 | (hexyloxycarbonyl group) | LC/MS (ESI): m/z = 612 [M + H]+, RT = 2.45 min, method (2) | |
| II-40 | (neopentyloxycarbonyl group) | LC/MS (ESI): m/z = 598 [M + H]+, RT = 2.29 min, method (2) | |

TABLE 8-continued

| No. | PR | data | comment |
|---|---|---|---|
| II-41 | (structure) | LC/MS (ESI): m/z = 672 [M + H]+, RT = 2.27 min, method (1) | |
| II-42 | (structure) | LC/MS (ESI): m/z = 706 [M + H]+, RT = 2.39 min, method (1) | |
| II-43 | (structure) | LC/MS (ESI): m/z = 644 [M + H]+, RT = 2.13 min, method (1) | |

TABLE 9

| No. | PR | data | comment |
|---|---|---|---|
| II-44 | (structure) | LC/MS (ESI): m/z = 630 [M + H]+, RT = 2.03 min, method (1) | |
| II-45 | (structure) | LC/MS (ESI): m/z = 644 [M + H]+, RT = 2.06 min, method (1) | |
| II-46 | (structure) | LC/MS (ESI): m/z = 644 [M + H]+, RT = 2.15 min, method (1) | |
| II-47 | (structure) | LC/MS (ESI): m/z = 692 [M + H]+, RT = 2.31 min, method (1) | |
| II-48 | (structure) | LC/MS (ESI): m/z = 670 [M + H]+, RT = 2.20 min, method (1) | |
| II-49 | (structure) | LC/MS (ESI): m/z = 700 [M + H]+, RT = 2.45 min, method (1) | |

TABLE 9-continued

| No. | PR | data | comment |
|---|---|---|---|
| II-50 | 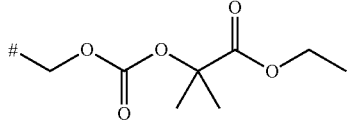 | LC/MS (ESI): m/z = 672 [M + H]+, RT = 2.31 min, method (1) | |
| II-51 | 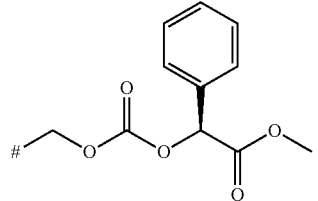 | LC/MS (ESI): m/z = 706 [M + H]+, RT = 2.37 min, method (1) | |
| II-52 | 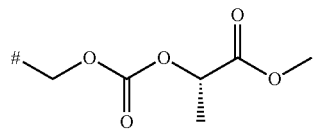 | LC/MS (ESI): m/z = 644 [M + H]+, RT = 2.13 min, method (1) | |
| II-53 | 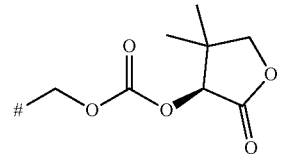 | LC/MS (ESI): m/z = 670 [M + H]+, RT = 2.16 min, method (1) | |
| II-54 | 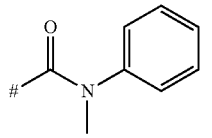 | LC/MS (ESI): m/z = 61 [M + H]+, RT = 2.09 min, method (2) | |
| II-55 | 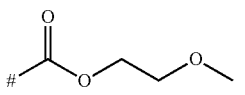 | LC/MS (ESI): m/z = 586 [M + H]+, RT = 1.91 min, method (2) | |
| II-56 | 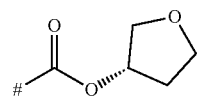 | LC/MS (ESI): m/z = 598 [M + H]+, RT = 1.89 min, method (2) | |
| II-57 | 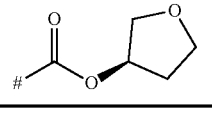 | LC/MS (ESI): m/z = 598 [M + H]+, RT = 1.89 min, method (2) | |

TABLE 10

| No. | PR | data | comment |
|---|---|---|---|
| II-58 | 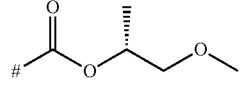 | LC/MS (ESI): m/z = 600 [M + H]+, RT = 2.01 min, method (2) | |
| II-59 | 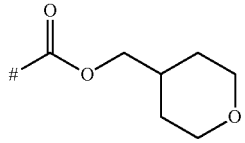 | LC/MS (ESI): m/z = 626 [M + H]+, RT = 1.98 min, method (2) | |

TABLE 10-continued

| No. | PR | data | comment |
|---|---|---|---|
| II-60 | | LC/MS (ESI): m/z = 612 [M + H]+, RT = 1.93 min, method (2) | |
| II-61 | | LC/MS (ESI): m/z = 626 [M + H]+, RT = 2.46 min, method (2) | |
| II-62 | | LC/MS (ESI): m/z = 682 [M + H]+, RT = 2.27 min, method (2) | |
| II-63 | | LC/MS (ESI): m/z = 719 [M + H]+, RT = 2.26 min, method (2) | |
| II-64 | | LC/MS (ESI): m/z = 731 [M + H]+, RT = 2.29 min, method (2) | |
| II-65 | | LC/MS (ESI): m/z = 691 [M + H]+, RT = 2.05 min, method (2) | |
| II-66 | | LC/MS (ESI): m/z = 689 [M + H]+, RT = 1.98 min, method (2) | |
| II-67 | | LC/MS (ESI): m/z = 759 [M + H]+, RT = 2.53 min, method (2) | |
| II-68 | | LC/MS (ESI): m/z = 640 [M + H]+, RT = 2.01 min, method (2) | |

TABLE 10-continued

| No. | PR | data | comment |
|---|---|---|---|
| II-69 | [structure] | LC/MS (ESI): m/z = 684 [M + H]+, RT = 1.87 min, method (2) | |
| II-70 | [structure] | LC/MS (ESI): m/z = 625 [M + H]+, RT = 1.75 min, method (2) | |

TABLE 11

| No. | PR | data | comment |
|---|---|---|---|
| II-71 | [structure] | LC/MS (ESI): m/z = 640 [M + H]+, RT = 1.90 min, method (2) | |
| II-72 | [structure] | LC/MS (ESI): m/z = 634 [M + H]+, RT = 1.82 min, method (2) | |
| II-73 | [structure] | LC/MS (ESI): m/z = 661 [M + H]+, RT = 1.90 min, method (2) | |
| II-74 | [structure] | LC/MS (ESI): m/z = 625 [M + H]+, RT = 1.38 min, method (2) | |
| II-75 | [structure] | LC/MS (ESI): m/z = 692 [M + H]+, RT = 2.00 min, method (2) | |
| II-76 | [structure] | LC/MS (ESI): m/z = 604 [M + H]+, RT = 2.09 min, method (2) | |
| II-78 | [structure] | LC/MS (ESI): m/z = 631 [M + H]+, RT = 2.18 min, method (2) | |
| II-79 | [structure] | LC/MS (ESI): m/z = 620 [M + H]+, RT = 1.93 min, method (2) | |

TABLE 11-continued

| No. | PR | data | comment |
|---|---|---|---|
| II-80 | (ethyl phosphate ester of hydroxy-dimethyl-butyrolactone) | LC/MS (ESI): m/z = 620 [M + H]+, RT = 1.93 min, method (2) | |
| II-81 | (1-(methoxycarbonylmethyl)cyclopentyl ethyl carbonate) | LC/MS (ESI): m/z = 614 [M + H]+, RT = 2.31 min, method (1) | |
| II-82 | (tert-butyl ethyl carbonate) | LC/MS (ESI): m/z = 614 [M + H]+, RT = 2.24 min, method (1) | |
| II-83 | (ethyl 3-((ethoxycarbonyl)oxy)-2,2-dimethylpropanoate) | LC/MS (ESI): m/z = 686 [M + H]+, RT = 2.27 min, method (1) | |
| II-84 | (ethyl 2-((formyloxy))-2-methylpropanoate derivative) | LC/MS (ESI): m/z = 642 [M + H]+, RT = 2.19 min, method (1) | |
| II-85 | (methyl 3-(formyloxy)-2,2-dimethylpropanoate) | LC/MS (ESI): m/z = 642 [M + H]+, RT = 2.17 min, method (1) | |
| II-86 | (methyl 2-(formyloxy)benzoate) | LC/MS (ESI): m/z = 662 [M + H]+, RT = 2.22 min, method (1) | |

TABLE 12

| No. | PR | data | comment |
|---|---|---|---|
| II-87 | (1-((formyloxy)methyl)cyclopentane-1-carboxylic acid methyl ester) | LC/MS (ESI): m/z = 668 [M + H]+, RT = 2.32 min, method (1) | |
| II-88 | (1-phenylethyl) | LC/MS (ESI): m/z = 588 [M + H]+, RT = 2.24 min, method (2) | |

TABLE 12-continued

| No. | PR | data | comment |
|---|---|---|---|
| II-89 | | LC/MS (ESI): m/z = 588 [M + H]+, RT = 2.17 min, method (2) | |
| II-90 | | LC/MS (ESI): m/z = 686 [M + H]+, RT = 2.67 min, method (2) | |
| II-92 | | LC/MS (ESI): m/z = 646 [M + H]+, RT = 2.12 min, method (2) | |
| II-93 | | LC/MS (ESI): m/z = 615 [M + H]+, RT = 2.24 min, method (2) | |
| II-94 | | LC/MS (ESI): m/z = 659 [M + H]+, RT = 2.31 min, method (2) | |
| II-95 | | LC/MS (ESI): m/z = 661 [M + H]+, RT = 2.06 min, method (2) | |
| II-96 | | LC/MS (ESI): m/z = 656 [M + H]+, RT = 2.24 min, method (1) | |
| II-97 | | 1H-NMR (CDCl3)δ: 1.24 (s, 3H), 1.38 (s, 3H), 2.94 (td, J = 11.8, 3.5 Hz, 1H), 3.44 (dd, J = 12.0, 10.9 Hz, 1H), 3.57 (t, J = 10.9 Hz, 1H), 3.78 (dd, J = 12.0, 3.5 Hz, 1H), 3.96 (dd, J = 10.9, 2.9 Hz, 1H), 4.05-4.12 (m, 3H), 4.58 (dd, J = 10.0, 2.9 Hz, 1H), 4.66 (d, J = 13.5 Hz, 1H) 5.24 (d, J = 13.5 Hz, 1H), 5.32 (s, 1H), 5.58 (s, 1H), 5.91 (d, J = 7.8 Hz, 1H), 6.81 (s, 2H), 7.06-7.20 (m, 5H). | |
| II-98 | | 1H-NMR (CDCl3)δ: 1.26 (s, 3H), 1.33 (s, 3H), 2.96 (t, J = 11.9 Hz, 1H), 3.46 (t, J = 10.6 Hz, 1H), 3.59 (t, J = 10.6 Hz, 1H), 3.77 (dd, J = 11.9, 2.9 Hz, 1H), 3.95 (dd, J = 11.0, 2.9 Hz, 1H), 4.04-4.13 (m, 3H), 4.56 (dd, J = 10.0, 2.9 Hz, 1H), 4.72 (d, J = 13.4 Hz, 1H), 5.27-5.31 (m, 2H). 5.37 (s, 1H), 5.91 (d, J = 8.0 Hz, 1H), 6.87-6.91 (m, 2H), 7.00-7.06 (m, 1H), 7.07-7.15 (m, 4H). | |
| II-99 | | 1H-NMR (CDCl3)δ: 2.92 (t, J = 11.0 Hz, 1H), 3.38 (t, J = 11.0 Hz, 1H), 3.56 (t, J = 10.4 Hz, 1H), 3.75 (d, J = 9.3 Hz, 1H), 3.81 (s, 3H), 3.95 (d, J = 9.3 Hz. 1H), 4.06 (d, J = 13.9 Hz, 1H), 4.55 (d, J = 8.1 Hz, 1H), 4.63 (d, J = 13.0 Hz, 1H), 5.27 (d, J = 13.9 Hz, 1H), 5.43 (br s, 1H), 5.91 (d, J = 8.1 Hz, 1H), 6.09 (s, 1H), 6.82-6.86 (m, 1H), 6.93 (d, J = 8.1 Hz, 1H), 7.04-7.13 (m, 5H), 7.39-7.43 (m, 3H), 7.56 7.59 (m, 2H). | |

TABLE 13

| No. | PR | data | comment |
|---|---|---|---|
| II-100 | 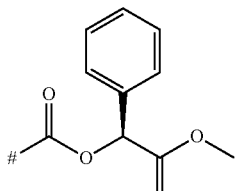 | 1H-NMR (CDCl3)δ: 2.94 (t, J = 11.3 Hz, 1H), 3.41 (t, J = 11.3 Hz, 1H), 3.5 (t, J = 10.5 Hz, 1H), 3.76 (d, J = 11.0 Hz, 1H), 3.83 (s, 3H), 3.94 (dd, J = 10.5, 2.7 Hz, 1H), 4.06 (d, J = 14.0 Hz, 1H), 4.55 (dd, J = 9.5, 2.7 Hz, 1H), 4.58 (d, J = 12.6 Hz, 1H), 5.28 (d, J = 14.0 Hz, 1H), 5.35 (s, 1H), 5.90 (d, J = 8.0 Hz, 1H), 6.05 (s, 1H), 6.84-6.90 (m, 2H), 7.00-7.15 (m, 5H), 7.38-7.42 (m, 3H), 7.56-7.60 (m, 2H). | |
| II-101 | 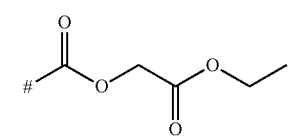 | LC/MS (ESI): m/z = 614 [M + H]+, RT = 2.10 min, method (1) | |
| II-102 | 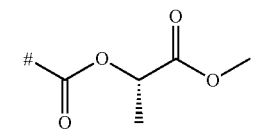 | LC/MS (ESI): m/z = 614 [M + H]+, RT = 2..04 min, method (1) | |
| II-103 | 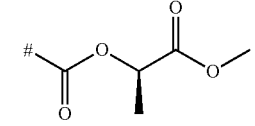 | LC/MS (ESI): m/z = 614 [M + H]+, RT = 2.02 min, method (1) | |
| II-104 | 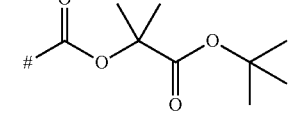 | LC/MS (ESI): m/z = 670 [M + H]+, RT = 2.41 min, method (l) | |
| II-106 | 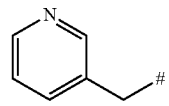 | LC/MS (ESI): m/z = 575 [M + H]+, RT = 1.49 min, method (2) | |
| II-107 | 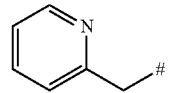 | LC/MS (ESI): m/z = 575 [M + H]+, RT = 1.52 min, method (2) | |
| II-108 | 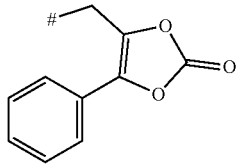 | LC/MS (ESI): m/z = 658 [M + H]+, RT = 2.23 min, method (2) | |
| II-109 | 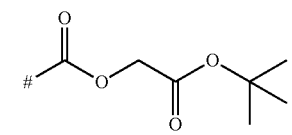 | LC/MS(ESI): m/z = 643 [M + H]+, RT = 2.28 min, method (1) | |
| II-110 | 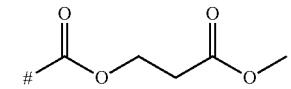 | LC/MS(ESI): m/z = 614 [M + H]+, RT = 1.97 min, method (1) | |

TABLE 13-continued

| No. | PR | data | comment |
|---|---|---|---|
| II-111 | 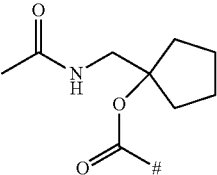 | LC/MS(ESI): m/z = 667 [M + H]+, RT = 1.99 min, method (1) | |
| II-112 | 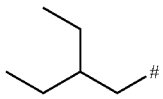 | LC/MS(ESI): m/z = 569 [M + H]+, RT = 2.42 min, method (1) | |
| II-113 | 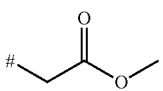 | LC/MS(ESI): m/z = 556 [M + H]+, RT = 1.91 min, method (1) | |
| II-114 |  | LC/MS(ESI): m/z = 528 [M + H]+, RT = 1.89 min, method (1) | |
| II-115 | 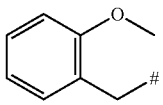 | LC/MS(ESI): m/z = 605 [M + H]+, RT = 2.19 min, method (1) | |

TABLE 14

| No. | PR | data | comment |
|---|---|---|---|
| II-116 |  | LC/MS(ESI): m/z = 526 [M + H]+, RT = 1.98 min, method (1) | |
| II-117 | 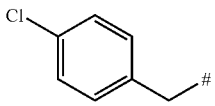 | LC/MS(ESI): m/z = 609 [M + H]+, RT = 2.36 min, method (1) | |
| II-118 | 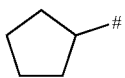 | LC/MS(ESI): m/z = 552 [M + H]+, RT = 2.16 min, method (1) | |
| II-119 | 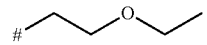 | LC/MS(ESI): m/z = 556 [M + H]+, RT = 1.96 min, method (1) | |
| II-120 |  | LC/MS(ESI): m/z = 512 [M + H]+, RT = 1.88 min, method (1) | |
| II-121 | 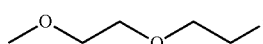 | LC/MS(ESI): m/z = 586 [M + H]+, RT = 1.88 min, method (1) | |
| II-122 | 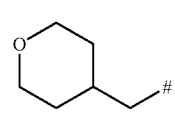 | LC/MS(ESI): m/z = 583 [M + H]+, RT = 1.94 min, method (1) | |
| II-123 |  | LC/MS(ESI): m/z = 542 [M + H]+, RT = 1.87 min, method (1) | |
| II-124 | 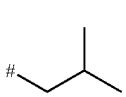 | LC/MS(ESI): m/z = 540 [M + H]+, RT = 2.15 min, method (1) | |
| II-125 |  | LC/MS(ESI): m/z = 498 [M + H]+, RT = 1.81 min, method (1) | |
| II-126 | 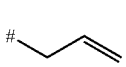 | LC/MS(ESI): m/z = 524 [M + H]+, RT = 1.97 min, method (1) | |

TABLE 14-continued

| No. | PR | data | comment |
|---|---|---|---|
| II-127 |  | LC/MS(ESI): m/z = 540 [M + H]+, RT = 2.14 min, method (1) | |
| II-128 | 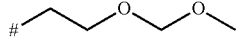 | LC/MS(ESI): m/z = 572 [M + H]+, RT = 2.04 min, method (1) | |
| II-129 | 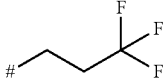 | LC/MS(ESI): m/z = 580 [M + H]+, RT = 2.16 min, method (1) | |
| II-130 | 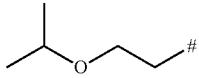 | LC/MS(ESI): m/z = 570 [M + H]+, RT = 2.05 min, method (1) | |
| II-131 | 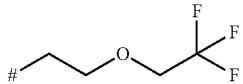 | LC/MS(ESI): m/z = 610 [M + H]+, RT = 2.18 min, method (1) | |
| II-132 | 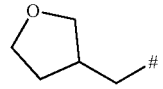 | LC/MS(ESI): m/z = 568 [M + H]+, RT = 1.90 min, method (1) | |
| II-133 | 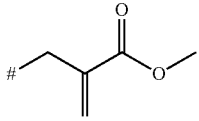 | LC/MS(ESI): m/z = 582 [M + H]+, RT = 1.99 min, method (1) | |
| II-134 | 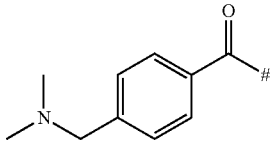 | LC/MS(ESI): m/z = 645 [M + H]+, RT = 1.45 min, method (2) | |
| II-135 | 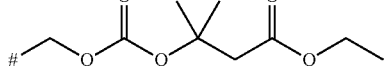 | LC/MS(ESI): m/z = 686 [M + H]+, RT = 2.27 min, method (1) | |
| II-136 | 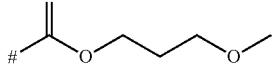 | LC/MS(ESI): m/z = 600 [M + H]+, RT = 1.97 min, method (2) | |
| II-137 | 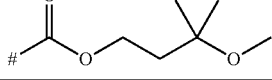 | LC/MS(ESI): m/z = 628 [M + H]+, RT = 2.11 min, method (2) | |

TABLE 15

| No. | PR | data | comment |
|---|---|---|---|
| II-138 | 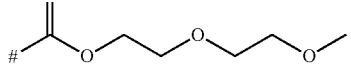 | LC/MS(ESI): m/z = 630 [M + H]+, RT = 1.92 min, method (2) | |
| II-139 | 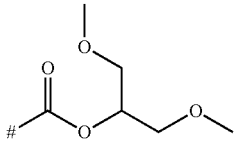 | LC/MS(ESI): m/z = 630 [M + H]+, RT = 2.11 min, method (2) | |

TABLE 15-continued

| No. | PR | data | comment |
|---|---|---|---|
| II-140 | 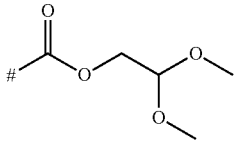 | LC/MS(ESI): m/z = 616 [M + H]+, RT = 1.99 min, method (2) | |
| II-141 | 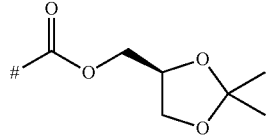 | LC/MS(ESI): m/z = 642 [M + H]+, RT = 2.06 min, method (2) | |
| II-142 | 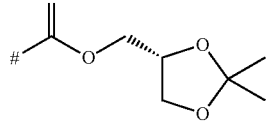 | LC/MS(ESI): m/z = 642 [M + H]+, RT = 2.06 min, method (2) | |
| II-143 | 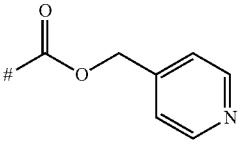 | LC/MS(ESI): m/z = 619 [M + H]+, RT = 1.52 min, method (2) | |
| II-144 | 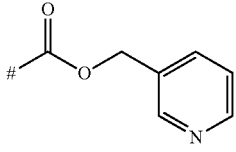 | LC/MS(ESI): m/z = 619 [M + H]+, RT = 1.63 min, method (2) | |
| II-145 | 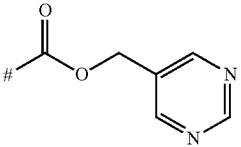 | LC/MS(ESI): m/z = 620 [M + H]+, RT = 1.80 min, method (2) | |
| II-146 | 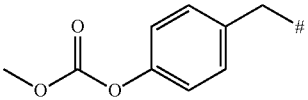 | LC/MS(ESI): m/z = 648 [M + H]+, RT = 2.10 min, method (2) | |
| II-147 | 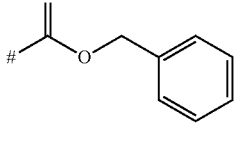 | LC/MS(ESI): m/z = 618 [M + H]+, RT = 2.25 min, method (1) | |
| II-148 | 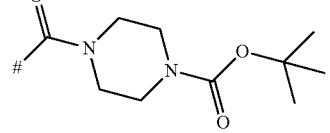 | LC/MS(ESI): m/z = 696 [M + H]+, RT = 2.14 min, method (1) | |
| II-149 | 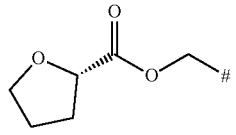 | LC/MS(ESI): m/z = 612 [M + H]+, RT = 1.92 min, method (2) | |

TABLE 15-continued

| No. | PR | data | comment |
|---|---|---|---|
| II-150 | 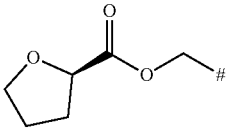 | LC/MS(ESI): m/z = 612 [M + H]+, RT = 1.92 min, method (2) | |
| II-151 | 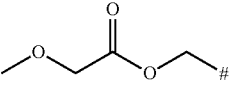 | LC/MS(ESI): m/z = 586 [M + H]+, RT = 1.87 min, method (2) | |

TABLE 16

| No. | PR | data | comment |
|---|---|---|---|
| II-152 | 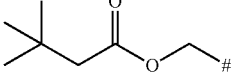 | LC/MS(ESI): m/z = 612 [M + H]+, RT = 2.34 min, method (2) | |
| II-153 | 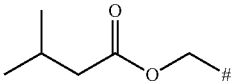 | LC/MS(ESI): m/z = 598 [M + H]+, RT = 2.23 min, method (2) | |
| II-154 | 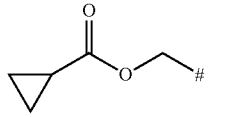 | LC/MS(ESI): m/z = 582 [M + H]K RT = 1.99 min, method (2) | |
| II-155 | 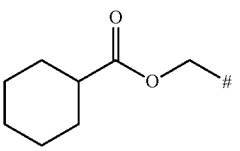 | LC/MS(ESI): m/z = 624 [M + H]+, RT = 2.37 min, method (2) | |
| II-156 | 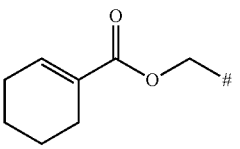 | LC/MS(ESI): m/z = 622 [M + H]+, RT = 2.27 min, method (2) | |
| II-157 | 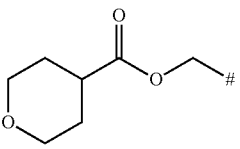 | LC/MS(ESI): m/z = 626 [M + H]+, RT = 2.00 min, method (2) | |
| II-158 | 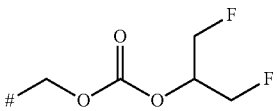 | LC/MS(ESI): m/z = 636 [M + H]+, RT = 2.15 min, method (1) | |
| II-159 | 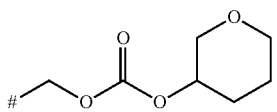 | LC/MS(ESI): m/z = 642 [M + H]+, RT = 2.09, 2.13 min, method (1) | diastereomer mixture |
| II-160 | 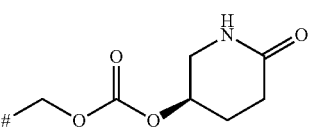 | LC/MS(ESI): m/z = 655 [M + H]+, RT = 1.76 min, method (1) | |

TABLE 16-continued

| No. | PR | data | comment |
|---|---|---|---|
| II-161 | 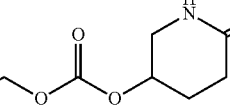 | LC/MS(ESI): m/z = 670 [M + H]+, RT = 2.00 min, method (1) | |
| II-162 | | LC/MS(ESI): m/z = 655 [M + H]+, RT = 1.81 min, method (1) | |
| II-163 | | LC/MS(ESI): m/z = 640 [M + H]+, RT = 2.11 min, method (1) | |
| II-164 | | LC/MS(ESI): m/z = 641 [M + H]+, RT = 1.79 min, method (1) | |
| II-165 | | LC/MS(ESI): m/z = 628 [M + H]+, RT = 2.03 min, method (1) | |

TABLE 17

| No. | PR | data | comment |
|---|---|---|---|
| II-166 | 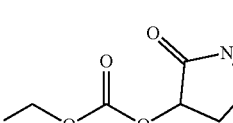 | LC/MS(ESI): m/z = 655 [M + H]+, RT = 1.76 min, method (1) | |
| II-167 | | LC/MS(ESI): m/z = 641 [M + H]+, RT - 1.79 min, method (1) | |
| II-168 | | LC/MS(ESI): m/z = 596 [M + H]+, RT = 1.55 min, method (1) | HCl salt |
| II-169 | | LC/MS(ESI): m/z = 556 [M + H]+, RT = 1.85 min, method (2) | |
| II-170 | | LC/MS(ESI): m/z = 598 [M + H]+, RT = 1.99 min, method (2) | |

TABLE 17-continued

| No. | PR | data | comment |
|---|---|---|---|
| II-171 | 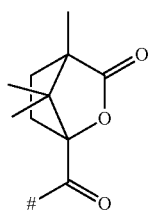 | LC/MS(ESI): m/z = 664 [M + H]+, RT = 2.19 min, method (2) | |
| II-172 | 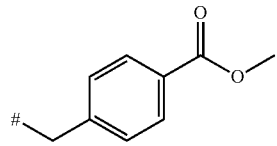 | LC/MS(ESI): m/z = 632 [M + H]+, RT = 2.11 min, method (2) | |
| II-173 | 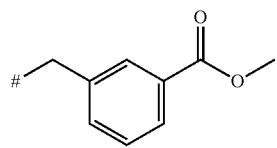 | LC/MS(ESI): m/z = 632 [M + H]+, RT = 2.12 min, method (2) | |
| II-174 | 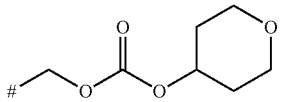 | LC/MS(ESI): m/z = 642 [M + H]+, RT = 2.05 min, method (1) | |
| II-175 | 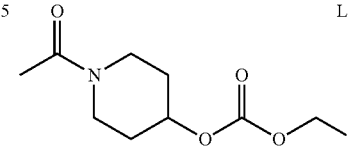 | LC/MS(ESI): m/z = 683 [M + H]+, RT = 1.88 min, method (1) | |
| II-176 | 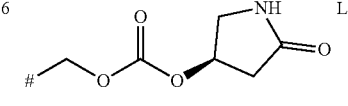 | LC/MS(ESI): m/z = 641 [M + H]+, RT = 1.75 min, method (1) | |
| II-177 | 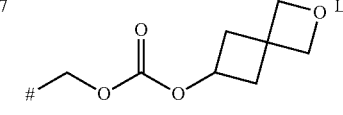 | LC/MS(ESI): m/z = 654 [M + H]+, RT = 2.00 min, method (1) | |
| II-178 | 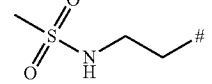 | LC/MS(ESI): m/z = 605 [M + H]+, RT = 1.88 min, method (1) | |
| II-179 | 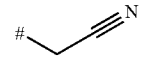 | LC/MS(ESI): m/z = 523 [M + H]+, RT = 1.93 min, method (1) | |
| II-180 | 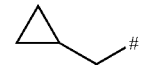 | LC/MS(ESI): m/z = 538 [M + H]+, RT = 2.01 min, method (1) | |

TABLE 18

| No. | PR | data | comment |
|---|---|---|---|
| II-181 | 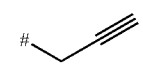 | LC/MS(ESI): m/z = 522 [M + H]+, RT = 1.91 min, method (1) | |

TABLE 18-continued

| No. | PR | data | comment |
|---|---|---|---|
| II-182 | 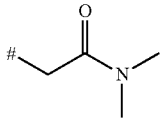 | LC/MS(ESI): m/z = 569 [M + H]+, RT = 1.77 min, method (1) | |
| II-183 | 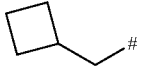 | LC/MS(ESI): m/z = 552 [M + H]+, RT = 2.17 min, method (1) | |
| II-184 | 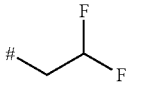 | LC/MS(ESI): m/z = 548 [M + H]+, RT = 2.05 min, method (1) | |
| II-185 | 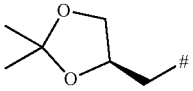 | LC/MS(ESI): m/z = 598 [M + H]+, RT = 2.05 min, method (1) | |
| II-186 | 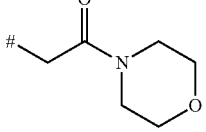 | LC/MS(ESI): m/z = 611 [M + H]+, RT = 1.78 min, method (1) | |
| II-187 | 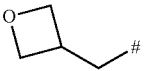 | LC/MS(ESI): m/z = 554 [M + H]+, RT = 1.82 min, method (1) | |
| II-188 | 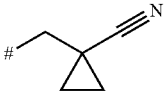 | LC/MS(ESI): m/z = 563 [M + H]+, RT = 1.98 min, method (1) | |
| II-189 | 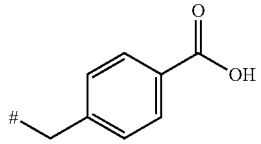 | LC/MS(ESI): m/z = 618 [M + H]+, RT = 1.85 min, method (2) | |
| II-190 | 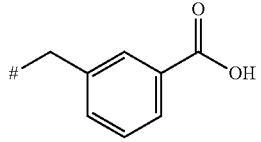 | LC/MS(ES!): m/z = 618 [M + H]+, RT = 1.86 min, method (2) | |
| II-191 | 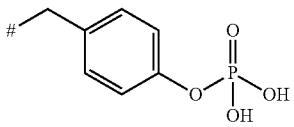 | LC/MS(ESI): m/z = 670 [M + H]+, RT = 1.84 min, method (2) | |
| II-192 | 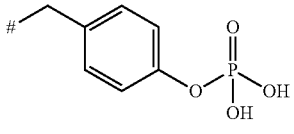 | LC/MS(ESI): m/z = 670 [M + H]+, RT = 1.84 min, method (2) | Na salt |
| II-193 | 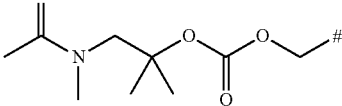 | LC/MS(ESI): m/z = 685 [M + H]+, RT = 1.89 min, method (1) | |

TABLE 18-continued

| No. | PR | data | comment |
|---|---|---|---|
| II-194 | (tetrahydrofuran-2-carbonyl) | LC/MS(ESI): m/z = 582 [M + H]+, RT = 1.91 min, method (2) | |
| II-195 | (tetrahydrofuran-2-carbonyl) | LC/MS(ESI): m/z = 582 [M + H]+, RT = 1.91 min, method (2) | |
| II-196 | (1-methylimidazol-5-ylmethyl) | LC/MS(ESI): m/z = 578 [M + H]+, RT = 1.33 min, method (2) | |

TABLE 19

| No. | PR | data | comment |
|---|---|---|---|
| II-197 | (oxazol-2-ylmethyl) | LC/MS(ESI): m/z = 565 [M + H]+, RT = 1.79 min, method (2) | |
| II-198 | (furan-2-ylmethyl) | LC/MS(ESI): m/z = 564 [M + H]+, RT = 1.95 min, method (2) | |
| II-199 | (thiophen-2-ylmethyl) | LC/MS(ESI): m/z = 580 [M + H]+, RT = 2.04 min, method (2) | |
| II-200 | (oxazol-4-ylmethyl) | LC/MS(ESI): m/z = 565 [M + H]+, RT = 1.78 min, method (2) | |
| II-201 | (2-methoxythiazol-5-ylmethyl) | LC/MS(ESI): m/z = 611 [M + H]+, RT = 1.95 min, method (2) | |
| II-202 | (2-(thiophen-3-yl)ethyl) | LC/MS(ESI): m/z = 594 [M + H]+, RT = 2.16 min, method (2) | |
| II-203 | (isoxazol-4-ylmethyl) | LC/MS(ESI): m/z = 565 [M + H]+, RT = 1.86 min, method (2) | |
| II-204 | (thiazol-2-ylmethyl) | LC/MS(ESI): m/z = 581 [M + H]+, RT = 1.87 min, method (2) | |
| II-205 | (5-methylisoxazol-3-ylmethyl) | LC/MS(ESI): m/z = 579 [M + H]+, RT = 1.95 min, method (2) | |
| II-206 | (4-methyl-1,2,5-oxadiazol-3-ylmethyl) | LC/MS(ESI): m/z = 580 [M + H]+, RT = 2.03 min, method (2) | |

TABLE 19-continued

| No. | PR | data | comment |
|---|---|---|---|
| II-207 | 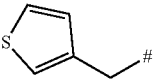 | LC/MS(ESI): m/z = 580 [M + H]+, RT = 2.07 min, method (2) | |
| II-208 | 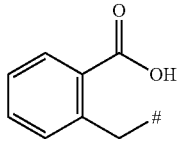 | LC/MS(ESI): m/z = 632 [M + H]+, RT = 2.15 min, method (2) | |
| II-209 | 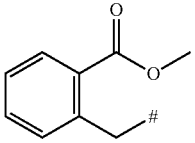 | LC/MS(ESI): m/z = 632 [M + H]+, RT = 2.15 min, method (2) | |
| II-210 | 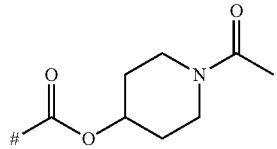 | LC/MS(ESI): m/z = 653 [M + H]+, RT = 1.81 min, method (2) | |
| II-211 | 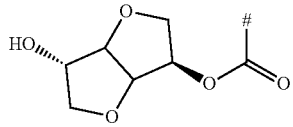 | LC/MS(ESI): m/z = 597 [M + H]+, RT = 1.75 min, method (2) | |
| II-212 |  | LC/MS(ESI): m/z = 580 [M + H]+, RT = 1.86 min, method (1) | |
| II-213 |  | LC/MS(ESI): m/z = 568 [M + H]+, RT = 1.89 min, method (1) | |
| II-214 | 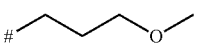 | LC/MS(ESI): m/z = 556 [M + H]+, RT = 1.94 min, method (1) | |

TABLE 20

| No. | PR | data | comment |
|---|---|---|---|
| II-215 | 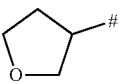 | LC/MS(ESI): m/z = 554 [M + H]+, RT = 1.85 min, method (3) | |
| II-216 | 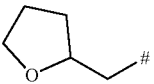 | LC/MS(ESI): m/z = 568 [M + H]+, RT = 1.94 min, method (3) | |
| II-217 | 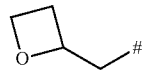 | LC/MS(ESI): m/z = 554 [M + H]+, RT = 1.88 min, method (1) | |
| II-218 | 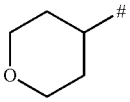 | LC/MS(ESI): m/z = 568 [M + H]+, RT = 1.82 min, method (2) | |

TABLE 20-continued

| No. | PR | data | comment |
|---|---|---|---|
| II-219 | morpholine-4-carbonyl | LC/MS(ESI): m/z = 597 [M + H]+, RT = 1.75 min, method (2) | |
| II-220 | 3-methoxy-3-methylbutyl | LC/MS(ESI): m/z = 584 [M + H]+, RT = 2.05 min, method (1) | |
| II-221 | 3-(allyloxy)propyl | LC/MS(ESI): m/z = 582 [M + H]+, RT = 2.12 min, method (1) | |
| II-222 | (2-oxooxazolidin-5-yl)methyl | LC/MS(ESI): m/z = 583 [M + H]+, RT = 1.76 min, method (1) | |
| II-223 | (5-oxopyrrolidin-3-yl) | LC/MS(ESI): m/z = 567 [M + H]+, RT = 1.70 min, method (1) | |
| II-224 | 3-hydroxy-2,2-dimethylpropyl | LC/MS(ESI): m/z = 570 [M + H]+, RT = 2.09 min, method (1) | |
| II-225 | 5-hydroxypent-3-yn-1-yl | LC/MS(ESI): m/z = 552 [M + H]+, RT = 1.81 min, method (1) | |
| II-226 | (E)-5-hydroxypent-3-en-1-yl | LC/MS(ESI): m/z = 554 [M + H]+, RT = 1.79 min, method (1) | |
| II-227 | (trimethylsilyl)methyl | LC/MS(ESI): m/z = 570 [M + H]+, RT = 2.39 min, method (1) | |
| II-228 | (5-oxopyrrolidin-2-yl)methyl | LC/MS(ESI): m/z = 581 [M + H]+, RT = 1.80 min, method (1) | |
| II-229 | 3-hydroxy-3-methylbutyl | LC/MS(ESI): m/z = 570 [M + H]+, RT = 1.96 min, method (1) | |
| II-230 | (2-oxo-1,3-dioxolan-4-yl)methyl | LC/MS(ESI): m/z = 584 [M + H]+, RT = 1.94 min, method (1) | |
| II-231 | 4-hydroxycyclohexyl | LC/MS(ESI): m/z = 582 [M + H]+, RT = 1.86 min, method (1) | |
| II-232 | 4-methoxybutan-2-yl | LC/MS(ESI): m/z = 570 [M + H]+, RT = 2.01 min, method (1) | |
| II-233 | (6-oxopiperidin-3-yl) | LC/MS(ESI): m/z = 581 [M + H]+, RT = 1.73 min, method (1) | |

TABLE 20-continued

| No. | PR | data | comment |
|---|---|---|---|
| II-234 | 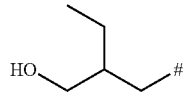 | LC/MS(ESI): m/z = 584 [M + H]+, RT = 1.83 min, method (1) | |

TABLE 21

| No. | PR | data | comment |
|---|---|---|---|
| II-235 | 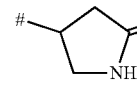 | LC/MS(ESI): m/z = 570 [M + H]+, RT = 2.06 min, method (1) | |
| II-236 | 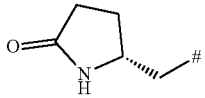 | LC/MS(ESI): m/z = 567 [M + H]+, RT = 1.70 min, method (1) | |
| II-237 | 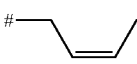 | LC/MS(ESI): m/z = 581 [M + H]+, RT = 1.80 min, method (1) | |
| II-238 | 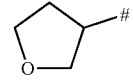 —OH | LC/MS(ESI): m/z = 554 [M + H]+, RT = 1.80 min, method (1) | |
| II-241 | 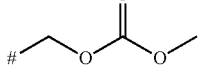 | LC/MS(ESI): m/z = 554 [M + H]+, RT = 1.88 min, method (1) | |

TABLE 22

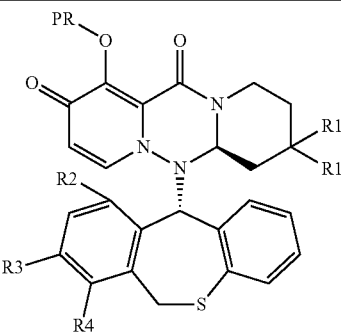

| No. | PR | R1 | R2 | R3 | R4 | data |
|---|---|---|---|---|---|---|
| II-242 | 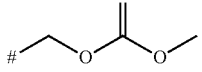 | F | H | F | F | LC/MS (ESI): m/z = 606 [M + H]+, RT = 2.12 min, method (2) |
| II-243 | 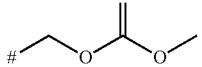 | F | F | H | H | LC/MS (ESI): m/z = 588 [M + H]+, RT = 2.00 min, method (2) |
| II-244 | 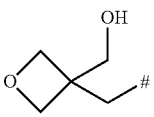 | F | H | F | H | LC/MS (ESI): m/z = 588 [M + H]+, RT = 2.04 min, method (2) |

TABLE 22-continued

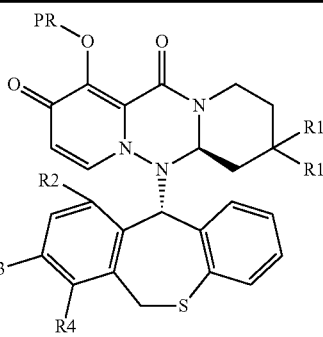

| No. | PR | R1 | R2 | R3 | R4 | data |
|---|---|---|---|---|---|---|
| II-245 | (methoxycarbonyloxymethyl) | Me | H | F | F | LC/MS (ESI): m/z = 598 [M + H]+, RT = 2.27 min, method (2) |
| II-246 | (methoxycarbonyloxymethyl) | Me | F | H | H | LC/MS (ESI): m/z = 580 [M + H]+, RT = 2.14 min, method (2) |
| II-247 | (methoxycarbonyloxymethyl) | Me | H | F | H | LC/MS (ESI): m/z = 580 [M + H]+, RT = 2.17 min, method (2) |

TABLE 23

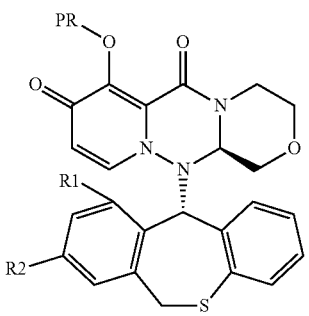

| No. | PR | R2 | R3 | data |
|---|---|---|---|---|
| II-248 | (acetyl) | F | H | LC/MS (ESI): m/z = 508 [M + H]+, RT = 1.76 min, method (2) |
| II-249 | (ethoxycarbonyloxymethyl) | F | H | LC/MS (ESI): m/z = 568 [M + H]+, RT = 1.91 min, method (1) |

TABLE 23-continued

| No. | PR | R2 | R3 | data |
|---|---|---|---|---|
| II-250 | CH₃C(O)OCH₂# | F | H | 1H-NMR(CDCL3)δ: 2.05(s, 3H), 2.92-3.02(m, 1H), 3.40-3.48 (m, 1H), 3.51-3.62(m, 2H), 3.72-3.80(m, 1H), 3.88-3.92(m, 1H), 4 50-4.56(m, 1H), 4.64-4.72(m, 1H), 5.55(d, J = 13.6 Hz, 1H), 5.78-5.82(m, 1H), 5.84-5.88(m, 1H), 5.90-5.98(m, 2H), 6.82-7.00(m, 2H), 7.00-7.20(m, 5H), 7.35-7.42(m, 1H) |
| II-251 | #CH₂OC(O)OCH₃ | F | H | LC/MS (ESI): m/z = 554 [M + H]+, RT = 1.76 min, method (1) |
| II-252 | #CH₂OC(O)OCH₂CH₂OCH₃ | F | H | LC/MS (ESI): m/z = 598 [M + H]+, RT = 1.80 min, method (2) |
| II-253 | CH₃C(O)# | H | F | LC/MS (ESI): m/z = 508 [M + H]+, RT = 1.76 min, method (2) |
| II-254 | CH₃C(O)OCH₂# | H | F | LC/MS (ESI): m/z = 538 [M + H]+, RT = 1.78 min, method (2) |
| II-255 | #CH₂OC(O)OCH₃ | H | F | LC/MS (ESI): m/z = 554 [M + H]+, RT = 1.81 min, method (2) |
| II-256 | #CH₂OC(O)OCH₂CH₂OCH₃ | H | F | LC/MS (ESI): m/z = 598 [M + H]+, RT = 1.85 min, method (2) |
| II-257 | (CH₃)₂CHC(O)# | F | H | 1H-NMR (CDCl3)δ: 1.42 (d, J = 6.8 Hz, 6H), 2.90-3.07 (m, 2H), 3.44 (t, J = 10.8 Hz, 1H), 3.60 (d, J = 12.8 Hz, 2H), 3.77 (d, J = 10.8 Hz, 1H), 3.93 (dd, J = 10.8, 2.8 Hz, 1H), 4.56 (dd, J = 9.6, 2.8 Hz, 1H), 4.67 (m, 1H), 5.59 (m, 1H), 5.87 (m, 1H), 5.59 (s, 1H), 6.91-7.21 (m. 7H), 7.38 (m, 1H). |
| II-258 | PhCH₂# | F | H | 1H-NMR (CDCl3)δ: 2.89-2.93 (m, 1H), 3.30-3.43 (m, 2H), 3.57 (d, J = 13.4 Hz, 1H), 3.73 (dd, J = 11.6, 2.8 Hz, 1H), 3.87 (dd, J = 10.7, 2.4 Hz, 1H), 4.49 (dd, J = 9.9, 2.5 Hz, 1H), 4.72 (d, J = 12.9 Hz, 1H), 5.43 (d, J = 10.8 Hz, 1H), 5.51 (d, J = 13.4 Hz, 1H), 5.64 (d, J = 10.9 Hz, 1H), 5.78 (d, J = 7.7 Hz, 1H), 5.84 (s, 1H), 6.44 (d, J = 7.8 Hz, 1H), 6.67 (t, J = 7.0 Hz, 1H), 7.02-7.13 (m, 5H), 7.29-7.40 (m, 4H), 7.64 (d, J = 7.7 Hz, 2H). |

TABLE 24

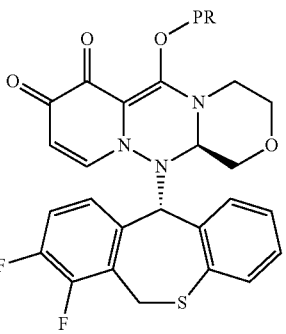

| No. | PR | LC/MS |
|---|---|---|
| II-259 | 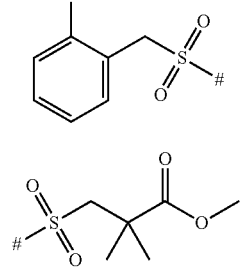 | LC/MS(ESI): m/z = 683 [M + H]+, RT = 2.33 min, method (1) |
| II-260 | 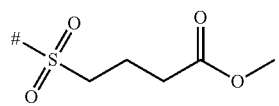 | LC/MS(ESI): m/z = 662 [M + H]+, RT = 2.22 min, method (1) |
| II-261 | 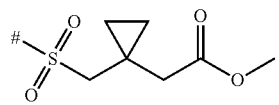 | LC/MS(ESI): m/z = 648 [M + H]+, RT = 2.09 min, method (1) |
| II-262 | 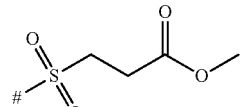 | LC/MS(ESI): m/z = 674 [M + H]+, RT = 2.20 min, method (1) |
| II-263 | 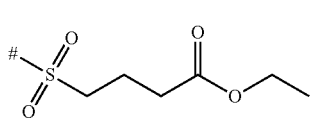 | LC/MS(ESI): m/z = 634 [M + H]+, RT = 2.07 min, method (1) |
| II-264 | 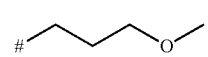 | LC/MS(ESI): m/z = 662 [M + H]+, RT = 2.22 min, method (1) |
| II-265 | 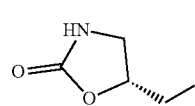 | LC/MS(ESI): m/z = 556 [M + H]+, RT = 1.79 min, method (1) |
| II-266 | 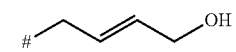 | LC/MS(ESI): m/z = 583 [M + H]+, RT = 1.59 min, method (1) |
| II-267 | 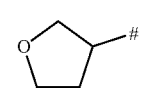 | LC/MS(ESI): m/z = 554 [M + H]+, RT = 1.65 min, method (1) |
| II-268 | 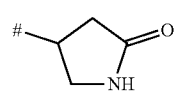 | LC/MS(ESI): m/z = 554 [M + H]+, RT = 1.71 min, method (1) |
| II-269 |  | LC/MS(ESI): m/z = 567 [M + H]+, RT = 1.51 min, method (1) |

TABLE 24-continued

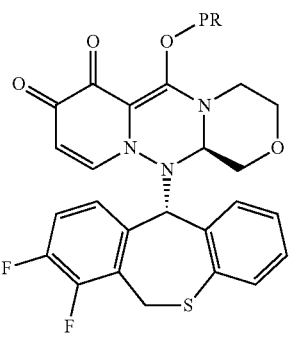

| No. | PR | LC/MS |
|---|---|---|
| II-270 | (trimethylsilylmethyl) | LC/MS(ESI): m/z = 570 [M + H]+, RT = 2.16 min, method (1) |
| II-271 | (5-oxopyrrolidin-2-yl)methyl | LC/MS(ESI): m/z = 581 [M + H]+, RT = 1.57 min, method (1) |
| II-272 | (oxetan-2-yl)methyl | LC/MS(ESI): m/z = 554 [M + H]+, RT = 1.70 min, method (1) |
| II-273 | trans-4-hydroxycyclohexyl | LC/MS(ESI): m/z = 582 [M + H]+, RT = 1.70 min, method (1) |
| II-274 | 4-methoxybutan-2-yl | LC/MS(ESI): m/z = 570 [M + H]+, RT = 1.89 min, method (1) |

TABLE 25

| No. | PR | LC/MS |
|---|---|---|
| II-275 | 6-oxopiperidin-3-yl | LC/MS(ESI): m/z = 581 [M + H]+, RT = 1.55 min, method (1) |
| II-276 | 2-ethyl-3-hydroxypropyl | LC/MS(ESI): m/z = 570 [M + H]+, RT = 1.81 min, method (1) |
| II-277 | ((S)-5-oxopyrrolidin-2-yl)methyl | LC/MS(ESI): m/z = 581 [M + HJ+, RT = 1.58 min, method (1) |
| II-278 | (Z)-4-hydroxybut-2-en-1-yl | LC/MS(ESI): m/z = 554 [M + H]+, RT = 1.65 min, method (1) |

TABLE 26

| No. | Structure | data |
|---|---|---|
| II-279 | 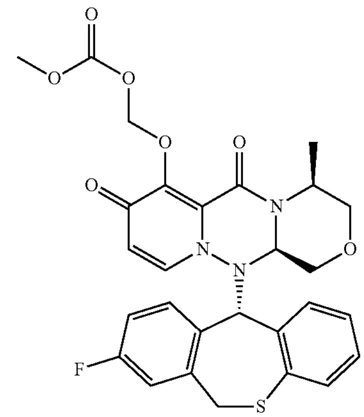 [SMILES: COC(=O)OCOc1c2n(ccc1=O)N([C@H]1c3ccc(F)cc3CSc3ccccc31)[C@@H]1COC[C@H](C)N1C2=O] | LC/MS (ESI): m/z = 568 [M + H]+, RT = 1.92 min, method (2) |
| II-280 | 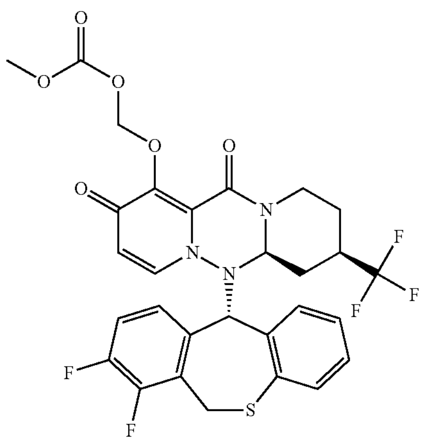 [SMILES: COC(=O)OCOc1c2n(ccc1=O)N([C@@H]1c3ccccc3SCc3c1ccc(F)c3F)[C@@H]1C[C@H](C(F)(F)F)CCN1C2=O] | LC/MS (ESI): m/z = 638 [M + H]+, RT = 2.17 min, method (2) |
| II-281 | 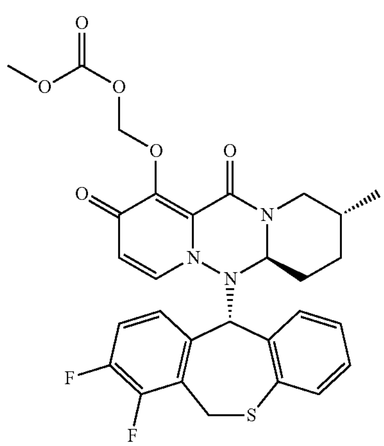 | LC/MS (ESI): m/z = 584 [M + H]+, RT = 2.18 min, method (2) |

TABLE 26-continued
| No. | Structure | data |
|---|---|---|
| II-282 | 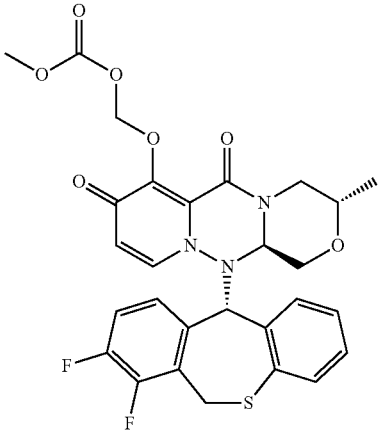 | LC/MS (ESI): m/z = 586 [M + H]+, RT = 2.03 min, method (2) |
| II-283 | 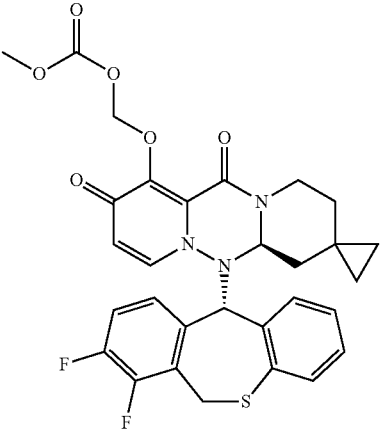 [SMILES: COC(=O)OCOc1c2n(ccc1=O)N([C@@H]1c3ccccc3SCc3c1ccc(F)c3F)[C@@H]1CC3(CCN1C2=O)CC3] | LC/MS (ESI): m/z = 596 [M + H]+, RT = 2.18 min, method (2) |
| II-284 | 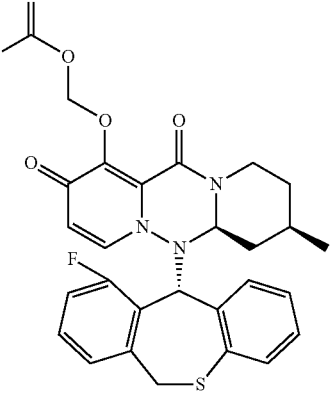 | LC/MS (ESI): m/z = 566 [M + H]+, RT = 2.02 min, method (2) |

TABLE 26-continued

| No. | Structure | data |
|---|---|---|
| II-285 | 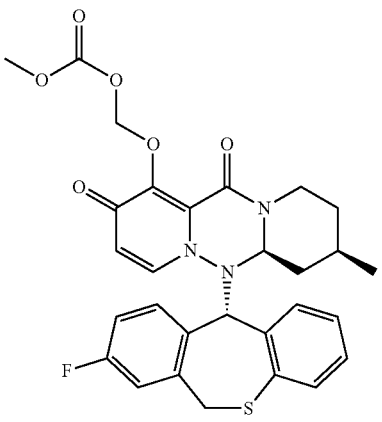 | LC/MS (ESI): m/z = 566 [M + H]+, RT = 2.08 min, method (2) |
| II-286 | 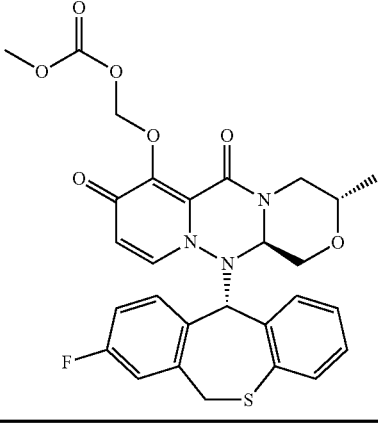 | LC/MS (ESI): m/z = 568 [M + H]+, RT = 1.93 min, method (2) |

Test Example 1: Measurement of Cap-Dependant Endonuclease (CEN) Inhibitory Activity 1) Preparation of Substrate 30 mer RNA(5'-pp-[m2'-O]GAA UAU(-Cy3) GCA UCA CUA GUA AGC UUU GCU CUA-BHQ2-3': manufactured by Japan Bio Services Co., LTD.) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPICENTRE (a product was m7G [5']-ppp-[5'] [m2'-O]GAA UAU(-Cy3) GCA UCA CUA GUA AGC UUU GCU CUA(-BHQ2)-3'). This was separated and purified by denatured polyacrylamide gel electrophoresis, and used as a substrate.

2) Preparation of Enzyme

RNP was prepared from a virus particle using standard method (Reference Document: VIROLOGY(1976) 73, p 327-338 OLGA M. ROCHOVANSKY). Specifically, A/WSN/33 virus (1×10³ PFU/mL, 200 µL) was inoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1-PB2-PA complex).

3) Enzymatic Reaction

An enzymatic reaction solution (2.5 µL) (composition: 53 mM Tris-hydrochloride (pH 7.8), 1 mM $MgCl_2$, 1.25 mM dithiothreitol, 80 mM NaCl, 12.5% glycerol, enzyme solution 0.15 µL) was dispensed into a 384-well plate made of polypropylene. Then, 0.5 µL of a test compound solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystems (ABI)) in order to stop the reaction. For NC, the reaction was stopped in advance by adding EDTA (4.5 mM) before initiation of the reaction (all concentrations described above are final concentrations).

4) Measurement of Inhibition Ratio ($IC_{50}$ Value)

The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an $IC_{50}$ value was obtained using curve fitting software (XLfit2.0: Model 205 (manufactured by IDBS) etc.).

Test Example 2: CPE Inhibitory Effect Confirming Assay

<Material>
2% FCS E-MEM (prepared by adding kanamycin and FCS to MEM (Minimum Essential Medium) (Invitrogen))
0.5% BSA E-MEM (prepared by adding kanamycin and BSA to MEM (Minimum Essential Medium) (Invitrogen))
HBSS (Hanks' Balanced Salt Solution)
MDBK cell
Cells were adjusted to the appropriate cell number ($3 \times 10^5$/mL) with 2% FCS E-MEM.
MDCK cell
After washing with HBSS two times, cells were adjusted to the appropriate cell number ($5 \times 10^5$/mL) with 0.5% BSA E-MEM.
Trypsin solution
Trypsin from porcine pancreas (SIGMA) was dissolved in PBS(−), and filtrated with a 0.45 μm filter.
EnVision (PerkinElmer)
WST-8 Kit (Kishida Chemical Co., Ltd.)
10% SDS solution
<Operation Procedure>
Dilution and dispensation of test sample As a culture medium, 2% FCS E-MEM was used at the use of MDBK cells, and 0.5% BSA E-MEM was used at the use of MDCK cells. Hereinafter, for diluting virus, cells and a test sample, the same culture medium was used.

A test sample was diluted with a culture medium to an appropriate concentration in advance, and then 2 to 5-fold serial dilution on a 96 well plate (50 μL/well) was prepared. Two plates, one for measuring anti-Flu activity and the another for measuring cytotoxity, were prepared. Each assay was performed triplicate for each drug.

At the use of MDCK cells, Trypsin was added to the cells to be a final concentration of 3 μg/mL only for measuring anti-Flu activity.

Dilution and dispensation of influenza virus

An influenza virus was diluted with a culture medium to an appropriate concentration in advance, and each 50 μL/well was dispensed on a 96-well plate containing a test substance. Each 50 μL/well of a culture medium was dispensed on a plate containing a test substance for measuring cytotoxity.

Dilution and dispensation of cell

Each 100 μL/well of cells which had been adjusted to the appropriate cell number was dispensed on a 96 well plate containing a test sample.

This was mixed with a plate mixer, and incubated in a CO2 incubator for 3 days for measuring anti-Flu activity and measuring cytotoxity.

Dispensation of WST-8

The cells in the 96-well plate which had been incubated for 3 days was observed visually under a microscope, and appearance of the cells, the presence or absence of a crystal of test substance were checked. The supernatant was removed so that the cells were not absorbed from the plate.

WST-8 Kit was diluted 10-fold with a culture medium, and each 100 μL was dispensed into each well. After mixing with a plate mixer, cells were incubated in a CO2 incubator for 1 to 3 hours.

After incubation, regarding the plate for measuring anti-Flu activity, each 10 μL/well of a 10% SDS solution was dispensed in order to inactivate a virus.

Measurement of absorbance

After the 96-well plate was mixed, absorbance was measured with EnVision at two wavelengths of 450 nm/620 nm.

<Calculation of Each Measurement Item Value>

The value was calculated using Microsoft Excel or a program having the equivalent calculation and processing ability, based on the following calculation equation.

Calculation of effective inhibition concentration to achieve 50% influenza infected cell death ($EC_{50}$) $EC50=10^Z$ $Z=(50\%-\text{High }\%)/(\text{High }\%-\text{Low }\%) \times \{\log(\text{High conc.})-\log(\text{Low conc.})\}+\log(\text{High conc.})$ For the parent compounds of the compound represented by formula (I) in (A), measurement results of Test Example 1 and Test Example 2 are shown in Table 27.

TABLE 27

| No. | CEN_IC50 nM | CPE_EC50 nM |
|---|---|---|
| III-1 | 1.93 | 1.13 |
| III-2 | 2.22 | 3.39 |
| III-3 | 2.17 | 10.9 |
| III-4 | 2.18 | 3.38 |
| III-5 | 3.94 | 4 |
| III-6 | 2.37 | 1.43 |
| III-7 | 4.06 | 2.7 |
| III-8 | 3.46 | 3.07 |
| III-9 | 1.48 | 0.864 |
| III-10 | 1.63 | 3 |
| III-11 | 10.7 | 5.67 |
| III-12 | 0.87 | 0.656 |
| III-13 | 5.68 | 3.01 |
| III-14 | 18.5 | 3.17 |
| III-15 | 2.08 | 2.36 |
| III-16 | 4.69 | 2.85 |
| III-17 | 3.86 | 3 |
| III-18 | 2.37 | 2.45 |
| III-19 | 4.24 | 3.43 |
| III-20 | 8.26 | 4.04 |
| III-21 | 2.75 | 2.81 |
| III-22 | 2.99 | 2.95 |
| III-23 | 2.1 | 2.17 |
| III-24 | 3.93 | 2.64 |
| III-25 | 3.9 | 3.18 |
| III-26 | 3.81 | 3.68 |
| III-27 | 1.63 | 3.07 |
| III-28 | 2.91 | 3.18 |
| III-29 | 2.25 | 2.53 |
| III-30 | 3.49 | 3.57 |
| III-31 | 6.79 | 4.17 |
| III-32 | 2.55 | 4.36 |
| III-33 | 2.22 | 2.58 |
| III-34 | 3.62 | 3.28 |

Comparative Example

According to the method described in Test Example 1, the results of measuring the CEN inhibitory activity of the parent compound as a racemate described in Patent Document 2 are as follows. "Bold line" and "dashed line" in the table indicate relative stereo and the following compounds are racemic.

TABLE 28

| Structure | CEN_IC50 nM |
|---|---|
| 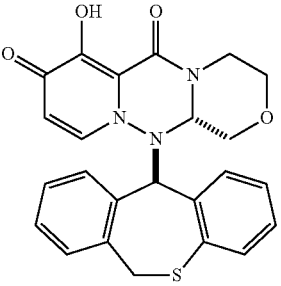 Reference 715 | 25.5 |
| 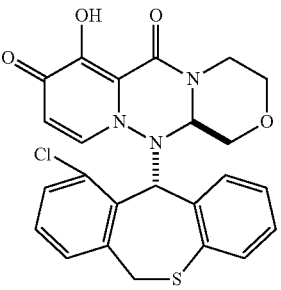 Reference 684 | 19.7 |
| 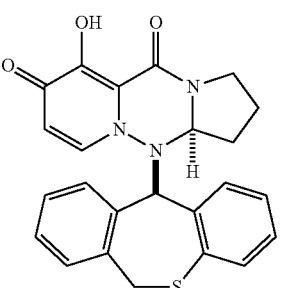 Reference 583 or 584 | 28.1 |
| 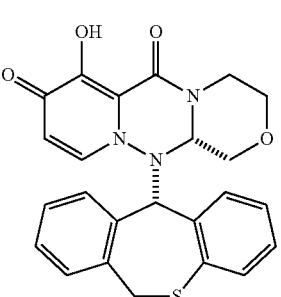 Reference 714 | 95.0 |

TABLE 28-continued

| Structure | CEN_IC50 nM |
|---|---|
| 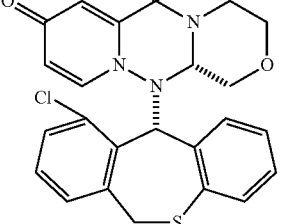 Reference 682 | 104 |
| 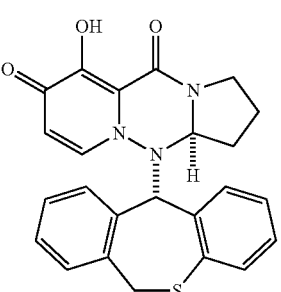 Reference 583 or 584 | 43.4 |

Based on the above test results, the parent compound of the compound represented by the formula (I) in (A) (a compound wherein P is hydrogen) has high cap-dependent endonuclease (CEN) inhibitory activity and/or high CPE inhibitory effect, and can be a useful medicine as a therapeutic and/or prophylactic agent for symptoms and/or diseases induced by infection with influenza virus.

Test Example 3: Synergistic CPE Inhibitory Effect Confirming Assay

<Material>
Trypsin solution
Trypsin from porcine pancreas (SIGMA) was dissolved in PBS(−), and filtrated with a 0.45 μm filter.
0.5% BSA MEM (prepared by adding kanamycin and BSA to MEM (Minimum Essential Medium) (Invitrogen))
MDCK cell
Cells were adjusted to the appropriate cell number ($7.5 \times 10^5$ cells/mL) with 0.5% BSA MEM
EnVision (PerkinElmer)
WST-8 Kit (Kishida Chemical Co., Ltd.)
10% SDS solution
<Operation Procedure>
Dilution and dispensation of cell
One day prior to infection, 80 μL of cell suspensions which had been adjusted to the appropriate cell number was dispensed to each well on a 96 well plate. The plates were incubated at 37° C. in a $CO_2$ incubator.
Dilution and dispensation of influenza virus
An influenza virus was diluted with 0.5% BSA MEM to an appropriate concentration, and 20 μL of virus dilution was dispensed to each wells on the plates (MOI=0.003). In order to attach the virus to cells, the plates were incubated at 37° C. in a $CO_2$ incubator for 1 hour.

Dilution and dispensation of test sample

A test sample was diluted with 0.5% BSA MEM containing 6 μg/mL trypsin to an appropriate concentration, and serial dilutions were prepared. After the viral attachment, the supernatants were removed and the cells were washed once to remove uninfected viruses. Fifty μL of 0.5% BSA MEM was added to each well on the plates. For each substance alone, 50 μL of the substance solutions were added to each well on the plates. For use in combination, 25 μL of the each substance solutions were added to each well on the plates. These plates were incubated at 37° C. in a $CO_2$ incubator for 2 or 3 days.

Dispensation of WST-8

The cells in the plates which had been incubated for 2 or 3 days were observed visually under a microscope, and appearance of the cells, the presence or absence of a crystal of test substance were checked. The supernatant was removed so that the cells were not absorbed from the plate. Hundred μL of MEM and 10 μL of WST-8 reagent were added to each well on the plates. After mixing with a plate mixer, the plates were incubated in a $CO_2$ incubator for 1 to 3 hours. After incubation, 10 μL of 10% SDS solution was dispensed to each well on the plates in order to inactivate the viral infectivity.

Measurement of absorbance

After the plates were mixed, absorbance was measured by EnVision using an absorption wavelength of 450 nm and 620 nm.

<Calculation of Each Measurement Item Value>

Calculation of effective inhibition concentration to achieve 50% influenza infected cell death ($EC_{50}$)

The % of inhibition against influenza virus replication was calculated by the following formula.

% of inhibition=$(X-Z)/(Y-Z)\times 100$

X: the average of O.D. (O.D. at 450 nm O.D. at 620 nm) of substance y: the average of O.D. (O.D. at 450 nm O.D. at 620 nm) of cell control Z: the average of O.D. (O.D. at 450 nm O.D. at 620 nm) of virus control The $EC_{50}$ of each substance was calculated by using software XLfit 5.3.1.3.

Calculation of combination index values (CIs)

CIs under the condition that both substances were added at the closest ratio of each $EC_{50}$ value were calculated by the following formula.

$$CI=(D_{A/A+B})/D_A+(D_{B/A+B})/D_B+(D_{A/A+B}\times D_{B/A+B})/(D_A\times D_B)$$

$D_A$: the $EC_{50}$ of substance A alone
$D_B$: the $EC_{50}$ of substance B alone
$D_{A/A+B}$: the concentration of substance A giving 50% inhibition in combination with substance B
$D_{B/A+B}$: the concentration of substance B giving 50% inhibition in combination with substance A <Determination of Combination Effect>

Combination effects were analyzed according to the report from Naruto Taira (Ac to Med. Okayama, 2006 vol. 60, p 25-34).

CI≤0.8: synergy
0.8≤CI<1.2: additive
1.2≤CI: antagonism

The EC 50 values of each single agent are shown in Table 29. Also, the CI values are shown in Table 30 in cases where the compound III-1 and the compound or antibody having an anti-influenza activity are used in combination at a ratio corresponding to the ratio of the EC50 values for each single agent.

TABLE 29

| | $EC_{50}$ (nM) | | | | | |
|---|---|---|---|---|---|---|
| Virus | III-1 | Oseltamivir | Peramivir | Laninamivir | Zanamivir | Favipiravir |
| A/WSN/33 (H1N1) | 2.85 | 59314.51 | | | | |
| A/PR/8/34 (H1N1) | 4.95 | 1829.67 | 213.77 | 212.74 | 1565.38 | 26919.33 |
| A/Victoria/3/75 (H3N2) | 3.48 | 244.62 | | | | |
| A/HongKong/8/68 (H3N2) | 2.08 | 71.19 | | | | |
| B/Maryland/1/59 | 14.70 | 863.72 | 353.88 | 109.81 | 162.60 | |

| | EC50 (nM) | | | | $EC_{50}$ (μg/mL) |
|---|---|---|---|---|---|
| Virus | VX-787 | Amantadine | Rimantadine | Tizoxanide | anti HA antibody |
| A/WSN/33 (H1N1) | | | | | |
| A/PR/8/34 (H1N1) | 9.38 | | | | 2.00 |
| A/Victoria/3/75 (H3N2) | | 2511.43 | 158.44 | 8314.73 | |
| A/HongKong/8/68 (H3N2) | | | | | |
| B/Maryland/1/59 | | | | | |

TABLE 30

| | CI value | | | | |
|---|---|---|---|---|---|
| Virus | III-1 + Oseltamivir | III-1 + Peramivir | III-1 + Laninamivir | III-1 + Zanamivir | III-1 + Favipiravir |
| A/WSN/33 (H1N1) | 0.38 | | | | |
| A/PR/8/34 (H1N1) | 0.53 | 0.59 | 0.58 | 0.52 | 0.99 |
| A/Victoria/3/75 (H3N2) | 0.31 | | | | |
| A/HongKong/8/68 (H3N2) | 0.45 | | | | |
| B/Maryland/1/59 | 0.86 | 0.94 | 1.06 | 0.91 | |

TABLE 30-continued

| | CI value | | | | |
|---|---|---|---|---|---|
| Virus | III-1 + VX-787 | III-1 + Amantadine | III-1 + Rimantadine | III-1 + Tizoxanide | III-1 + anti HA antibody |
| A/WSN/33 (H1N1) | | | | | |
| A/PR/8/34 (H1N1) | 0.61 | | | | 0.84 |
| A/Victoria/3/75 (H3N2) | | 0.82 | 0.80 | 0.87 | |
| A/HongKong/8/68 (H3N2) | | | | | |
| B/Maryland/1/59 | | | | | |

Based on the above test results, it was found that combination administrations of the compound (No. III-1) and the neuraminidase inhibitor (Oseltamivir, peramivir, Laninaminivir and Zanamivir), and the compound (No. III-1) and the PB2 Cap binding inhibitor (VX-787) were exhibited superior synergistic proliferation inhibitory effect on influenza virus A as compared with each single agent administration. Based on this fact, it has been found combinations a compound having a cap-dependent endonuclease inhibitory activity, its pharmaceutically acceptable salt or a solvate thereof with (B-1) a compound having a neuraminidase inhibitory activity, its pharmaceutically acceptable salt or a solvate thereof, or (B-2) a compound having a PB2 Cap binding inhibitory activity, its pharmaceutically acceptable salt or a solvate thereof were exhibited superior synergistic proliferation inhibitory effect on influenza virus A.

Also, it was found that combination administrations of the compound (No. III-1) with the RNA-dependent RNA polymerase inhibitor (Favipiravir), the M2 protein inhibitor (Amantadine and Rimantadine), the HA maturation inhibitor (Tizoxanide) and the anti-HA antibody were exhibited additive proliferation inhibitory effect on influenza virus A without antagonistic effect as compared with each single agent administration. Therefore, it has been found combinations a compound having a cap-dependent endonuclease inhibitory activity, its pharmaceutically acceptable salt or a solvate thereof with (B-3) a compound having a RNA-dependent RNA polymerase inhibitory activity, its pharmaceutically acceptable salt or a solvate thereof, (B-4) a compound having a M2 protein inhibitory activity, its pharmaceutically acceptable salt or a solvate thereof, (B-5) a compound having a HA maturation inhibitory activity, its pharmaceutically acceptable salt or a solvate thereof or (B-6) an anti-HA antibody were exhibited additive proliferation inhibitory effect on influenza virus A.

In addition, it was found that combination administration of the compound (No. III-1) and the neuraminidase inhibitor (Oseltamivir, peramivir, Laninaminivir and Zanamivir) was exhibited additive proliferation inhibitory effect on influenza virus B without antagonistic effect as compared with each single agent administration. Therefore, it has been found combination a compound having a cap-dependent endonuclease inhibitory activity, its pharmaceutically acceptable salt or a solvate thereof with (B-1) a compound having a neuraminidase inhibitory activity, its pharmaceutically acceptable salt or a solvate thereof was exhibited additive proliferation inhibitory effect on influenza virus B.

Test Example 4: BA Test

Materials and methods for experiments to evaluate oral absorption
(1) Experimental animals: mice or SD rats were used.
(2) Rearing condition: mice or SD rats were allowed free access to solid feed and sterilized tap water.

(3) Setting of dosage and grouping: Oral administration and intravenous administration were performed with the predetermined dosage. Grouping was set as below. (Dosage was changed per compound)
  Oral administration 1 to 30 mg/kg (n=2 to 3)
  Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed from caudal vein by syringes with needle.
(6) Evaluation items: Blood was collected serially and concentration of a compound of the present invention in plasma was measured by LC/MS/MS.
(7) Statistical analysis: About transition of concentration of a compound of the present invention in plasma, the area under the plasma concentration versus time curve (AUC) was calculated by non-linear least-squares method program, WinNonlin (a registered trademark), and bioavailability (BA) of a compound of the present invention was calculated from AUCs of the oral administration group and the intravenous administration group.
(Result)
Compound II-6: 14.9%
Compound III-2: 4.2%

Based on the above results, the prodrug had improved bioavailability other than the parent compound.

Therefore, the compound of the present invention has excellent oral absorbability and can be a useful agent for treatment and/or prevention of symptom and/or disease induced by infection with influenza virus.

FIG. 1 shows a result of measuring the plasma concentration of Compound III-1 after oral administration of prodrug Compound II-4, the parent compound of which is Compound III-1 in (A), to rat under non-fasting conditions.

FIG. 2 shows a result of measuring the plasma concentration of Compound II-4 after oral administration of prodrug Compound II-4, the parent compound of which is Compound III-1 in (A), to rat under non-fasting conditions.

The concentration of Compound II-4 in all plasma samples was a determination limit or less. Therefore, prodrug Compound II-4, the parent compound of which is Compound III-1, is found to have changed promptly to Compound III-1 in vivo after administration (see FIG. 2).

Similarly, the plasma concentration of each Compound II-2, II-260 and II-139 in all plasma samples was a determination limit or less after oral administration of each prodrug compound, the parent compound of which is Compound III-1, to monkey under non-fasting conditions.

Based on the above test results, it was revealed that the prodrug compound of the compound represented by the formula (I) in (A) was absorbed into the body after oral administration, and rapidly converted into a parent compound in the blood. Therefore, the prodrug compound of the compound represented by the formula (I) in (A) can be a useful agent for treatment and/or prevention of symptom and/or disease induced by infection with influenza virus.

Based on the above test results, the medicament of the present invention can be a useful agent for treatment and/or prevention of symptom and/or disease induced by infection with influenza virus.

FORMULATION EXAMPLE

The following Formulation Examples are only exemplified and not intended to limit the scope of the invention.

Formulation Example 1: Tablets

The compound represented by the formula (I), a compound having an anti-influenza activity and/or an antibody with anti-influenza activity, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compound represented by the formula (I), a compound having an anti-influenza activity and/or an antibody with anti-influenza activity, lactose and calcium stearate are mixed uniformly to obtain powder medicines in the form of powders or fine granules. The powder medicines are filled into capsule containers to give capsules.

Formulation Example 3: Granules

The compound represented by the formula (I), a compound having an anti-influenza activity and/or an antibody with anti-influenza activity, lactose and calcium stearate are mixed uniformly and the mixture is compressed and molded. Then, it is crushed, granulated and sieved to give suitable sizes of granules.

Formulation Example 4: Orally Disintegrated Tablets

The compound represented by the formula (I), a compound having an anti-influenza activity and/or an antibody with anti-influenza activity and crystalline cellulose are mixed, granulated and tablets are made to give orally disintegrated tablets.

Formulation Example 5: Dry Syrups

The compound represented by the formula (I), a compound having an anti-influenza activity and/or an antibody with anti-influenza activity and lactose are mixed, crushed, granulated and sieved to give suitable sizes of dry syrups.

Formulation Example 6: Injections

The compound represented by the formula (I), a compound having an anti-influenza activity and/or an antibody with anti-influenza activity and phosphate buffer are mixed to give injection.

Formulation Example 7: Infusions

The compound represented by the formula (I), a compound having an anti-influenza activity and/or an antibody with anti-influenza activity and phosphate buffer are mixed to give injection.

Formulation Example 8: Inhalations

The compound represented by the formula (I), a compound having an anti-influenza activity and/or an antibody with anti-influenza activity and lactose are mixed and crushed finely to give inhalations.

Formulation Example 9: Ointments

The compound represented by the formula (I), a compound having an anti-influenza activity and/or an antibody with anti-influenza activity and petrolatum are mixed to give ointments.

Formulation Example 10: Patches

The compound represented by the formula (I), a compound having an anti-influenza activity and/or an antibody with anti-influenza activity and base such as adhesive plaster or the like are mixed to give patches.

INDUSTRIAL APPLICABILITY

The medicament of the present invention can be a medicine useful as a therapeutic and/or prophylactic agent for symptoms and/or diseases induced by infection with influenza virus.

The invention claimed is:
1. A pharmaceutical composition comprising:
(A) a compound represented by the following formula:

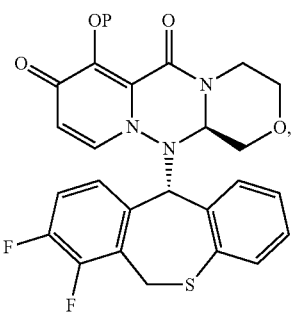

or a pharmaceutically acceptable salt thereof,
wherein:
P is hydrogen or a group selected from the group consisting of:
a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$, k) —C(P^{R3})_2—O-L-O—P^{R4},
l) —C(P^{R3})_2—O—C(=O)—P^{R4},
m) —C(P^{R3})_2—O—C(=O)—O—P^{R4},
n) —C(P^{R3})_2—O—C(=O)—N(—K)—P^{R4},
o) —C(P^{R3})_2—O—C(=O)—O-L-O—P^{R4},
p) —C(P^{R3})_2—O—C(=O)—O-L-N(P^{R4})_2,
q) —C(P^{R3})_2—O—C(=O)—N(—K)-L-O—P^{R4},
r) —C(P^{R3})_2—O—C(=O)—N(—K)-L-N(P^{R4})_2,
s) —C(P^{R3})_2—O—C(=O)—O-L-O-L-O—P^{R4},
t) —C(P^{R3})_2—O—C(=O)—O-L-N(—K)—C(=O)—P^{R4},
u) —C(P^{R3})_2—O—P(=O)(—P^{R5})_2,
v) —(C(P^{R3})_2)_p—P^{R6},
w) —C(=N^+(P^{R7})_2)(—N(P^{R7})_2),
x) —(C(P^{R3})_2)_q—C(=O)—O—P^{R2},
x') —(C(P^{R3})_2)_q—C(=O)—N(—K)—P^{R4},
x") —(C(P^{R3})_2)_q—C(=O)—P^{R1},
y) —C(P^{R3})_2—N(—K)—C(=O)—O—P^{R2},
z) —P(=O)(—P^{R8})(—P^{R9}),
aa) —S(=O)_2P^{R10},
ab) —P^{R11},
ac) —(C(P^{R3})_2)_r—O—P^{R12}, and
ad) —(C(P^{R3})_2)_t—N(—K)—P^{R13}, wherein L is straight or branched alkylene optionally substituted by substituent group B, or straight or branched alkenylene optionally substituted by substituent group B;

K is hydrogen, or alkyl optionally substituted by substituent group A;

P^{R0} is alkyl optionally substituted by substituent group A, or alkenyl optionally substituted by substituent group A;

P^{R1} is carbocyclyl group optionally substituted by substituent group A, heterocyclyl group optionally substituted by substituent group A, alkylamino optionally substituted by substituent group A, or alkylsulfanyl optionally substituted by substituent group A;

P^{R2} is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;

P^{R3} is each independently hydrogen, alkyl or hydroxy;
two P^{R3} on adjacent carbon atom may be taken together to form alkenylene or alkylene;

P^{R4} is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;

P^{R5} is each independently hydroxy or OBn;

P^{R6} is carbocyclyl group optionally substituted by substituent group A, or heterocyclyl group optionally substituted by substituent group A;

P^{R7} is each independently alkyl optionally substituted by substituent group A;

P^{R8} is alkyloxy optionally substituted by substituent group A;

P^{R9} is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or P^{R8} and P^{R9} may be taken together with an adjacent phosphorus atom to form heterocycle optionally substituted by substituent group A;

P^{R10} is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;

P^{R11} is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;

P^{R12} is each independently hydrogen or alkyl optionally substituted by substituent group A;

P^{R13} is alkylsulfonyl optionally substituted by substituent group A;

p is any integer of 2 to 3;
q is any integer of 1 to 2;
r is any integer of 2 to 4; and
t is any integer of 2 to 4;

wherein substituent group A is selected from the group consisting of oxo, alkyl, alkenyl, haloalkyl, hydroxyalkyl, amino, alkylamino, carbocyclyl group, heterocyclyl group, carbocyclylalkyl, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho; and substituent group B is selected from the group consisting of spiro ring and halogen, and (B) at least one compound selected from the group consisting of Oseltamivir, Zanamivir, Peramivir, Laninamivir, and VX-787, or a pharmaceutically acceptable salt thereof.

2. The pharmaceutical composition according to claim 1, wherein P is hydrogen or a group of the following formula:
m) —C(P^{R3})_2—O—C(=O)—O—P^{R4},
wherein
P^{R3} is each independently hydrogen, or alkyl;
P^{R4} is alkyl optionally substituted by substituent group A, carbocyclyl group optionally substituted by substituent group A, or heterocyclyl group optionally substituted by substituent group A;
wherein substituent group A is selected from the group consisting of oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

3. The pharmaceutical composition according to claim 1, wherein P is hydrogen or a group selected from the group consisting of:
a) —C(=O)—P^{R0},
b) —C(=O)—P^{R1},
g) —C(=O)—O—P^{R2},
h) —C(=O)—N(—K)(P^{R2}),
i) —C(=O)—O-L-O—P^{R2}, i') —C(=O)—O-L-N(—K)(P$^{R2}$),
l) —C(P$^{R3}$)$_2$—O—C(=O)—P$^{R4}$,
m) —C(P$^{R3}$)$_2$—O—C(=O)—O—P$^{R4}$,
o) —C(P$^{R3}$)$_2$—O—C(=O)—O-L-O—P$^{R4}$,
t) —C(P$^{R2}$—O—C(=O)—O-L-N(—K)—C(=O)—P$^{R4}$,
v) —(C(P$^{R3}$)$_2$)$_p$—P$^{R6}$,
x) —(C(P$^{R3}$)$_2$)$_q$—C(=O)—O—P$^{R2}$,
x') —(C(P$^{R3}$)$_2$)$_q$—C(=O)—N(—K)—P$^{R4}$,
x") —(C(P$^{R3}$)$_2$)$_q$—C(=O)—P$^{R1}$,
y) —C(P$^{R3}$)$_2$—N(—K)—C(=O)—O—P$^{R2}$,
z) —P(=O)(—P$^{R8}$)(—P$^{R9}$),
aa) —S(=O)$_2$P$^{R10}$,
ab) —P$^{R11}$,
ac) —(C(P$^{R3}$)$_2$)$_r$—O—P$^{R12}$, and
ad) —(C(P$^{R3}$)$_2$)$_t$—N(—K)—P$^{R13}$, wherein L is straight or branched alkylene optionally substituted by substituent group B;
K is hydrogen, or alkyl optionally substituted by substituent group A;
P$^{R0}$ is alkyl optionally substituted by substituent group A;
P$^{R1}$ is carbocyclyl group optionally substituted by substituent group A or heterocyclyl group optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
P$^{R3}$ is each independently hydrogen, alkyl or hydroxy; two P$^{R3}$ on adjacent carbon atom may be taken together to form alkenylene or alkylene;
P$^{R4}$ is alkyl optionally substituted by substituent group A, carbocyclyl group optionally substituted by substituent group A or heterocyclyl group optionally substituted by substituent group A;
P$^{R6}$ is carbocyclyl group optionally substituted by substituent group A or heterocyclyl group optionally substituted by substituent group A;
P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and
P$^{R8}$ and P$^{R9}$ may be taken together with an adjacent phosphorus atom to form heterocycle optionally substituted by substituent group A;
P$^{R10}$ is alkyl optionally substituted by substituent group A, carbocyclyl group optionally substituted by substituent group A or carbocyclylalkyl optionally substituted by substituent group A;
P$^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;
P$^{R12}$ is each independently hydrogen or alkyl optionally substituted by substituent group A;
P$^{R13}$ is alkylsulfonyl optionally substituted by substituent group A;
p is any integer of 2 to 3;
q is any integer of 1 to 2;
r is any integer of 2 to 4; and
t is any integer of 2 to 4;
wherein substituent group A is selected from the group consisting of oxo, alkyl, alkenyl, haloalkyl, alkylamino, carbocyclyl group, heterocyclyl group, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho; and
substituent group B is spiro ring.

4. The pharmaceutical composition according to claim 1, wherein (A) is a compound represented by the formula:

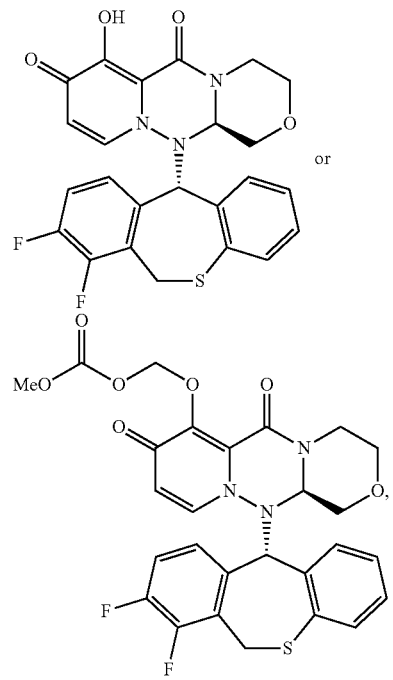

or a pharmaceutically acceptable salt thereof.

5. The pharmaceutical composition according to claim 4, wherein (A) is a compound represented by the formula:

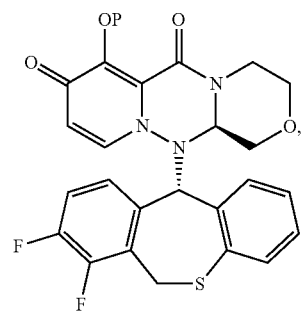

or a pharmaceutically acceptable salt thereof.

6. The pharmaceutical composition according to claim 4, wherein (A) is a compound represented by the formula:

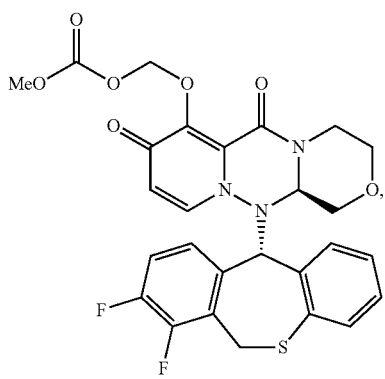 [SMILES: COC(=O)OCOc1c2n(ccc1=O)N([C@@H]1c3ccccc3SCc3c1ccc(F)c3F)[C@@H]1COCCN1C2=O]

or a pharmaceutically acceptable salt thereof.

7. A method of treating influenza comprising administering a combination of
(A) a compound represented by the following formula:

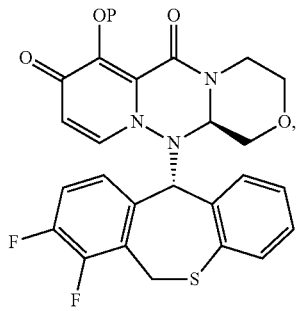

wherein
P is hydrogen or a group selected from the group consisting of:
a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
i') —C(=O)—O-L-N(—K)($P^{R2}$),
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —(C($P^{R3}$)$_2$)$_p$—$P^{R6}$,
w) —C(=N$^+$($P^{R7}$)$_2$)(—N($P^{R7}$)$_2$),
x) —(C($P^{R3}$)$_2$)$_q$—C(=O)—O—$P^{R2}$,
x') —(C($P^{R3}$)$_2$)$_q$—C(=O)—N(—K)—$P^{R4}$,
x'') —(C($P^{R3}$)$_2$)$_q$—C(=O)—$P^{R1}$,
y) —C($P^{R3}$)$_2$—N(—K)—C(=O)—O—$P^{R2}$,
z) —P(=O)(—$P^{R8}$)(—$P^{R9}$),
aa) —S(=O)$_2P^{R10}$,
ab) —$P^{R11}$,
ac) —(C($P^{R3}$)$_2$)$_r$—O—$P^{R12}$, and
ad) —(C($P^{R3}$)$_2$)$_t$—N(—K)—$P^{R13}$, wherein L is straight or branched alkylene optionally substituted by substituent group B, or straight or branched alkenylene optionally substituted by substituent group B;

K is hydrogen, or alkyl optionally substituted by substituent group A;

$P^{R0}$ is alkyl optionally substituted by substituent group A, or alkenyl optionally substituted by substituent group A;

$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;

$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;

$P^{R3}$ is each independently hydrogen, alkyl or hydroxy;
two $P^{R3}$ on adjacent carbon atom may be taken together to form alkenylene or alkylene;

$P^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;

$P^{R5}$ is each independently hydroxy or OBn;

$P^{R6}$ is carbocyclyl group optionally substituted by substituent group A, or heterocyclyl group optionally substituted by substituent group A;

$P^{R7}$ is each independently alkyl optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; or $P^{R8}$ and $P^{R9}$ may be taken together with an adjacent phosphorus atom to form heterocycle optionally substituted by substituent group A;

$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;

$P^{R11}$ is alkyl optionally substituted by substituent group A, alkenyl optionally substituted by substituent group A, alkynyl optionally substituted by substituent group A, carbocyclyl group optionally substituted by substituent group A, or heterocyclyl group optionally substituted by substituent group A;

$P^{R12}$ is each independently hydrogen or alkyl optionally substituted by substituent group A;

$P^{R13}$ is alkylsulfonyl optionally substituted by substituent group A;

p is any integer of 2 to 3;

q is any integer of 1 to 2;

r is any integer of 2 to 4; and t is any integer of 2 to 4;

wherein substituent group A is selected from the group consisting of oxo, alkyl, alkenyl, haloalkyl, hydroxyalkyl, amino, alkylamino, carbocyclyl group, heterocyclyl group, carbocyclylalkyl, spiro ring, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phosphor and substituent group B is selected from the group consisting of spiro ring and halogen, or a pharmaceutically acceptable salt thereof, and (B) at least one compound selected from the group consisting of Oseltamivir, Zanamivir, Peramivir, Laninamivir, and VX-787, or a pharmaceutically acceptable salt thereof, in a therapeutically effective amount thereof to an individual in need of treatment for influenza.

8. The method according to claim 7, wherein

P is hydrogen or a group of the formula —C($P^{R3}$)$_2$—O—C(=O)—O—$P^{R4}$;

$P^{R3}$ is each independently hydrogen or alkyl;

$P^{R4}$ is alkyl optionally substituted by substituent group A, carbocyclyl group optionally substituted by substituent group A, or heterocyclyl group optionally substituted by substituent group A; and substituent group A is selected from the group consisting of oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

9. The method according to claim 7, wherein (A) is a compound represented by the formula:

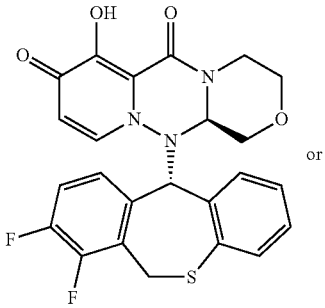

or

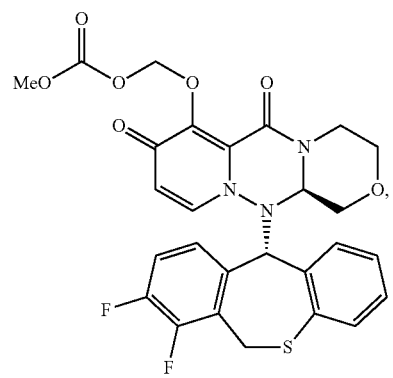 [SMILES: COC(=O)OCOc1c2n(ccc1=O)N([C@@H]1c3ccccc3SCc3c1ccc(F)c3F)[C@@H]1COCCN1C2=O]

or a pharmaceutically acceptable salt thereof.

10. The method according to claim 7, wherein the combination of (A) and (B) is administered simultaneously or sequentially to the individual.

11. The method according to claim 9, wherein the combination of (A) and (B) is administered simultaneously or sequentially to the individual.

12. The method according to claim 9, wherein (A) is a compound represented by the formula:

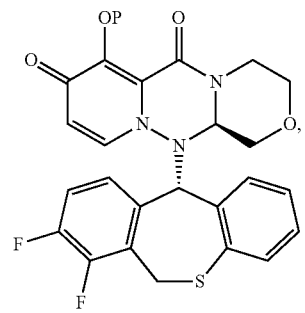

or a pharmaceutically acceptable salt thereof.

13. The method according to claim 9, wherein (A) is a compound represented by the formula:

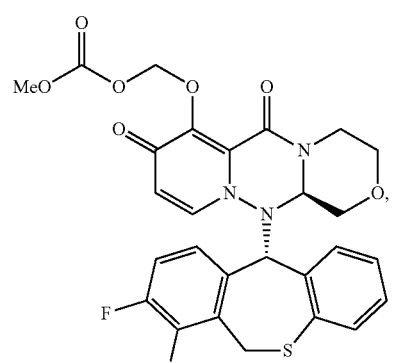

or a pharmaceutically acceptable salt thereof.

14. The method according to claim 11, wherein (A) is a compound represented by the formula:
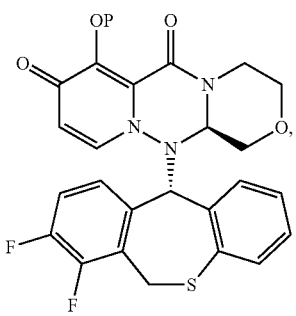
or a pharmaceutically acceptable salt thereof.
15. The method according to claim 11, wherein (A) is a compound represented by the formula:
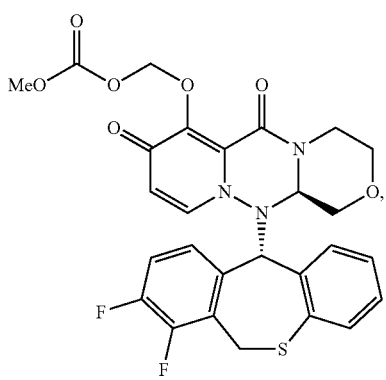 [SMILES: COC(=O)OCOc1c2n(ccc1=O)N([C@@H]1c3ccccc3SCc3c1ccc(F)c3F)[C@@H]1COCCN1C2=O]
or a pharmaceutically acceptable salt thereof.
* * * * *

UNITED STATES PATENT AND TRADEMARK OFFICE
CERTIFICATE OF CORRECTION

PATENT NO.       : 11,040,048 B2  
APPLICATION NO.  : 16/061495  
DATED            : June 22, 2021  
INVENTOR(S)      : Takao Shishido Page 1 of 2

It is certified that error appears in the above-identified patent and that said Letters Patent is hereby corrected as shown below:

In the Claims

Claim 5, in Column 150, Lines 50-64:

" 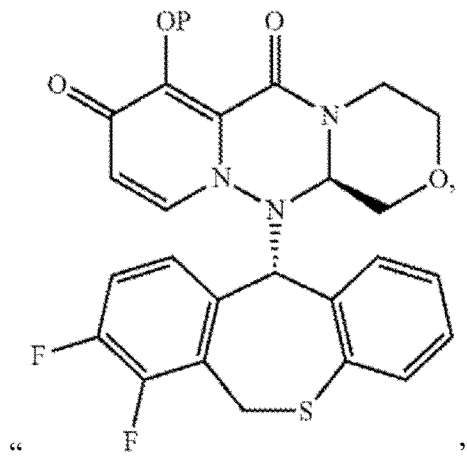 ", should read -- 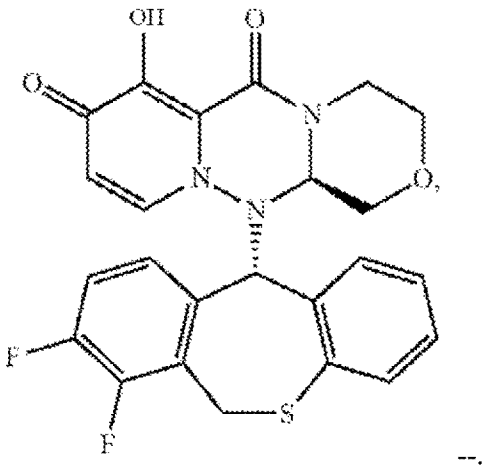 --.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,040,048 B2

Claim 12, in Column 154, Lines 30-44:

" 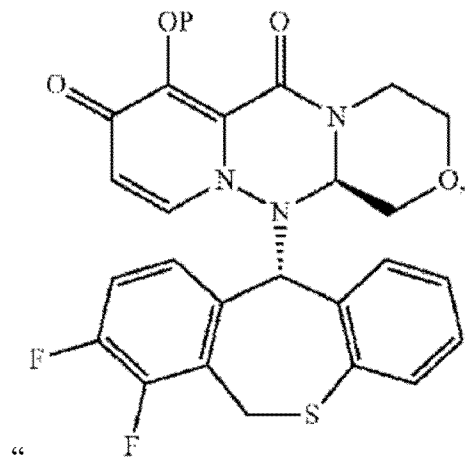 ", should read -- 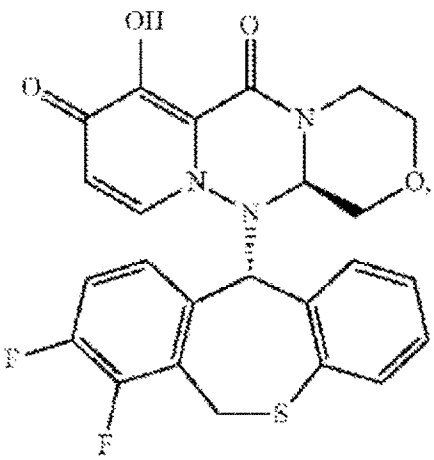 --.

Claim 14, in Column 155, Lines 5-19:

" 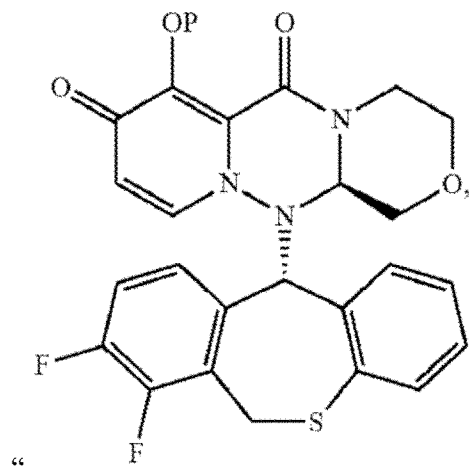 ", should read -- 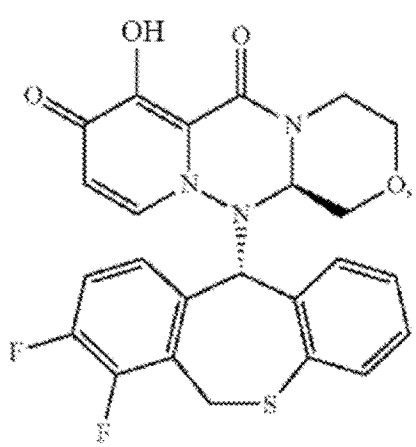 --.